(12) United States Patent
Jaeschke et al.

(10) Patent No.: US 11,345,708 B2
(45) Date of Patent: May 31, 2022

(54) SUBSTITUTED IMIDAZO[1,2-A]IMIDAZOLES AS MODULATORS OF METABOTROPIC GLUTAMATE RECEPTOR 4 ACTIVITY

(71) Applicant: Hoffmann-La Roche Inc., Little Falls, NJ (US)

(72) Inventors: Georg Jaeschke, Basel (CH); Fionn O'Hara, Basel (CH); Eric Vieira, Frenkendorf (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 17 days.

(21) Appl. No.: 16/790,290

(22) Filed: Feb. 13, 2020

(65) Prior Publication Data

US 2020/0291033 A1    Sep. 17, 2020

Related U.S. Application Data

(63) Continuation of application No. PCT/EP2018/072160, filed on Aug. 16, 2018.

(30) Foreign Application Priority Data

Aug. 17, 2017  (EP) .................................. 17186573

(51) Int. Cl.
  *A61K 31/4188*  (2006.01)
  *C07D 403/02*  (2006.01)
  *C07D 487/04*  (2006.01)

(52) U.S. Cl.
  CPC .................................. *C07D 487/04* (2013.01)

(58) Field of Classification Search
  CPC .......................... A61K 31/4188; C07D 403/02
  USPC ........................................ 514/393; 548/303.1
  See application file for complete search history.

(56) References Cited

FOREIGN PATENT DOCUMENTS

WO      2013/050454 A1    4/2013
WO      2015/104271 A1    7/2015
WO      WO-2019034713 A1 * 2/2019   ........... C07D 487/04

OTHER PUBLICATIONS

Jordan, V. C. Nature Reviews: Drug Discovery, 2, 2003, 205-213.*
Hackam, et al. JAMA, 296(14), 2006, 1731-1732.*
Battaglia et al., "Pharmacological Activation of mGlu4 Metabotropic Glutamate Receptors Reduces Nigrostriatal Degeneration in Mice Treated with 1-Methyl-4-Phenyl-1,2,3,6-Tetrahydropyridine" Journal of Neuroscience 26(27):7222-7229 (2006).
Célanire et al., "Recent advances in the drug discovery of metabotropic glutamate receptor 4 (mGluR4) activators for the treatment of CNS and non-CNS disorders" Expert Opinion in Drug Discovery 7(3):261-280 (2012).
Chang et al., "Metabotropic Glutamate Receptor 4 Expression in Colorectal Carcinoma and Its Prognostic Significance" Clinical Cancer Research 11(9):3288-3295 (2005).
International Preliminary Report on Patentability for PCT/EP2018/072160 dated Feb. 18, 2020, 7 pages.
International Search Report for PCT/EP2018/072160 dated Sep. 19, 2018, 6 pages.
Marino et al., "Allosteric modulation of group III metabotropic glutamate receptor 4: A potential approach to Parkinson's disease treatment" Proceedings of National Academy of Sciences of the United States of America / PNAS 100(23):13668-16673 (2003).
Niswender et al., "Discovery, Characterization, and Antiparkinsonian Effect of Novel Positive Allosteric Modulators of Metabotropic Glutamate Receptor 4" Molecular Pharmacology 74(5):1345-1358 (2008).
Palucha et al., "Group III mGlu receptor agonists produce anxiolytic- and antidepressant-like effects after central administration in rats" Neuropharmacology 46:151-159 (2004).

(Continued)

*Primary Examiner* — Douglas M Willis
(74) *Attorney, Agent, or Firm* — Andre T. Krammer

(57) ABSTRACT

The present invention relates to compounds of formula I

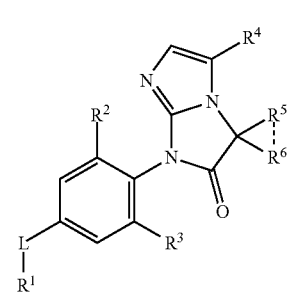

wherein
L is a bond, a triple bond, —C(O)NH— or —NHC(O)—;
$R^1$ is phenyl or a five or six-membered heteroaryl group, optionally substituted by lower alkyl, lower alkyl substituted by halogen or lower alkoxy substituted by halogen;
$R^2$ is fluoro;
$R^3$ is fluoro or chloro;
$R^4$ is hydrogen, lower alkyl, halogen, lower alkyl substituted by hydroxy, $S(O)_2CH_3$, or is a five or six-membered heteroaryl group or a heterocycloalkyl group, which are optionally substituted by lower alkyl, hydroxy or =O;
$R^5$ and $R^6$ are both methyl and the dotted line is a bond, or $R^5$ and $R^6$ are both methyl and the dotted line is nothing, or
one of $R^5$ and $R^6$ is hydrogen and the other is methyl, and the dotted line is nothing; or to a pharmaceutically acceptable salt or acid addition salt, to all possible tautomeric forms, to a racemic mixture, or to its corresponding enantiomer and/or optical isomer and/or stereoisomer thereof. The compounds may be used for the treatment of Parkinson's disease, anxiety, emesis, obsessive compulsive disorder, autism, neuroprotection, cancer, depression and diabetes type 2.

13 Claims, No Drawings

(56) References Cited

OTHER PUBLICATIONS

Pissimissis et al., "The Glutamatergic System Expression in Human PC-3 and LNCaP Prostate Cancer Cells" Anticancer Research 29(1):371-378 (2009).
Prediger et al., "Anxiety in Parkinson's disease: A critical review of experimental and clinical studies" Neuropharmacology 62:115-124 (2012).
Stachowicz et al., "Anxiolytic-like effects of PHCCC, an allosteric modulator of mGlu4 receptors, in rats" European Journal of Pharmacology 498(1-3):153-156 (2004).
Uehara et al., "Metabotropic Glutamate Receptor Type 4 is Involved in Autoinhibitory Cascade for Glucagon Secretion by α-Cells of Islet of Langerhans" Diabetes 53(4):998-1006 ( 2004).
Vernon et al., "Additive neuroprotection by metabotropic glutamate receptor subtype-selective ligands in a rat Parkinson's model" Neuroreport 19(4):475-480 (2008).

\* cited by examiner

SUBSTITUTED IMIDAZO[1,2-A]IMIDAZOLES AS MODULATORS OF METABOTROPIC GLUTAMATE RECEPTOR 4 ACTIVITY

CROSS-REFERENCE TO RELATED APPLICATIONS

This application is a continuation of International Application No. PCT/EP2018/072160, filed on Aug. 16, 2018, which claims priority from European Patent Application No. 17186573.6, filed on Aug. 17, 2017, the contents of which are incorporated herein by reference in their entireties.

BACKGROUND

Together with GRM6, GRM7 and GRM8 it belongs to group III of the Metabotropic glutamate receptor family, and is negatively coupled to adenylate cyclase via activation of the Gαi/o protein. It is expressed primarily on presynaptic terminals, functioning as an autoreceptor or heteroceptor and its activation leads to decreases in transmitter release from presynaptic terminals. mGluR4 is currently receiving much attention based primarily upon its unique distribution and the recent evidence that activation of this receptor plays key modulatory role in many CNS and non-CNS pathways (Celanire S, Campo B, *Expert Opinion in Drug Discovery*, 2012)

The similarity in the ligand binding domains of group III mGluRs creates a challenge for identifying selective orthosteric agonists of this receptor, although some progress has been made in this area. However, targeting positive allosteric modulators (PAMs) rather than orthosteric agonists provides a broader opportunity to identify molecules that are exclusively selective between mGluRs.

mGluR4 PAMs are emerging as promising therapeutic agents for the treatment of motor (and non-motor) symptoms as well as a disease-modifying agent in Parkinson's disease through a non-dopaminergic approach.

Parkinson's disease is a progressive neurodegenerative disease that results in the loss of dopaminergic neurons in the substantia nigra (SN). One consequence of the depletion of dopamine in this disease is a series of movement disorders, including bradykinesia, akinesia, tremor, gait disorders and problems with balance. These motor disturbances form the hallmark of PD, although there are many other non-motor symptoms that are associated with the disease. Early in the course of the disease, PD symptoms are effectively treated by dopamine replacement or augmentation, with the use of dopamine D2 receptor agonists, levodopa or monoamine oxidase B inhibitors. However, as the disease progresses these agents become less effective in controlling motor symptoms. Additionally, their use is limited by the emergence of adverse effects including dopamine agonist-induced dyskinesias. Consequently, there remains a need for new approaches to the treatment of PD that improve the effectiveness of the control of motor symptoms.

Activation of metabotropic glutamate receptor 4 (mGluR4) has been proposed as a potential therapeutic approach to Parkinson's disease. A member of the group III mGluRs, mGluR4 is predominantly a presynaptic glutamate receptor that is expressed in several key locations in the basal ganglia circuits that control movement. Activation of mGluR4 with group III-preferring agonists decreases inhibitory and excitatory post synaptic potentials, presumably by decreasing the release of GABA and glutamate respectively.

The search for novel drugs that relieve motor symptoms of Parkinsonism whilst attenuating the ongoing degeneration of nigrostriatal neurons is of particular interest. Orthosteric mGluR4 agonist L-AP4 has demonstrated neuroprotective effects in a 6-OHDA rodent model of PD and first positive allosteric modulator (−)-PHCCC reduced nigrostriatal degeneration in mice treated with 1-Methyl-4-Phenyl-1,2,3,6-Tetrahydropyridine (MPTP). These studies provide convincing preclinical evidence suggesting that mGluR4 activators constitute a valid approach not only for symptomatic treatments of PD, but also potentially as disease modifiers for this indication.

The neuroprotective effects of selective mGluR4 modulators was also described in *Neuroreport*, 19(4), 475-8, 2008, *Proc. Natl. Acad. Sci, USA*, 100(23), 13668-73, 2003 and *J. Neurosci.* 26(27), 7222-9, 2006 and *Mol. Pharmacol.* 74(5), 1345-58, 2008.

Anxiety disorders are among the most prevalent psychiatric disorders in the world, and are co-morbid with Parkinson's disease (Prediger R, et al. *Neuropharmacology* 2012; 62:115-24). Excessive glutamatergic neurotransmission is one important feature of anxiety pathophysiology. Based on presynaptic localization of mGluR4 in brain areas involved in anxiety and mood disorders, and dampening excessive brain excitability, the mGluR4 activators may represent a new generation of anxiolytic therapeutics (*Eur. J. Pharmacol.*, 498(1-3), 153-6, 2004).

Addex has reported in 2010 that ADX88178 was active in two preclinical rodent models of anxiety: the marble burying test in mice and EPM in mice and rats. ADX88178 also displayed an anxiolytic-like profile in the rat EPM test after oral dosing.

mGluR4 modulators were also shown to exert anti-depressive actions (*Neuropharmacology*, 46(2), 151-9, 2004).

In addition, mGluR4 modulators were also shown to be involved in glucagon secretion inhibition (*Diabetes*, 53(4), 998-1006, 2004). Therefore, orthosteric or positive allosteric modulators of mGluR4 have potential for the treatment of type 2 diabetes through its hypoglycemic effect.

Moreover, mGluR4 was shown to be expressed in prostate cancer cell-line (*Anticancer Res.* 29(1), 371-7, 2009) or colorectal carcinoma (*Cli. Cancer Research*, 11(9)3288-95, 2005). mGluR4 modulators may therefore have also potential role for the treatment of cancers.

Other proposed effects of mGluR4 PAMs can be expected for the treatment of emesis, obsessive compulsive disorder, anorexia and autism.

SUMMARY OF THE DISCLOSURE

The present invention relates to compounds of formula I

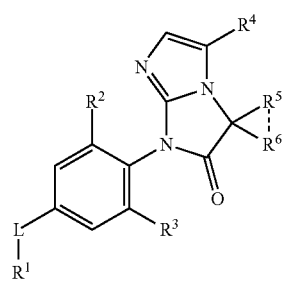

I wherein
L is a bond, a triple bond, —C(O)NH— or —NHC(O)—;
$R^1$ is phenyl or a five or six-membered heteroaryl group, optionally substituted by lower alkyl, lower alkyl substituted by halogen or lower alkoxy substituted by halogen;
$R^2$ is fluoro;
$R^3$ is fluoro or chloro;
$R^4$ is hydrogen, lower alkyl, halogen, lower alkyl substituted by hydroxy, $S(O)_2CH_3$, or is a five or six-membered heteroaryl group or a heterocycloalkyl group, which are optionally substituted by lower alkyl, hydroxy or =O;
$R^5$ and $R^6$ are both methyl and the dotted line is a bond, or
$R^5$ and $R^6$ are both methyl and the dotted line is nothing, or
one of $R^5$ and $R^6$ is hydrogen and the other is methyl, and the dotted line is nothing;
or to a pharmaceutically acceptable salt or acid addition salt, to all possible tautomeric forms, to a racemic mixture, or to its corresponding enantiomer and/or optical isomer and/or stereoisomer thereof.

It has surprisingly been found that the compounds of general formula I are positive allosteric modulators (PAMs) of metabotropic glutamate receptor 4 (mGluR4).

Metabotropic glutamate receptor 4 is a protein that in humans is encoded by the GRM4 gene.

DETAILED DESCRIPTION OF THE DISCLOSURE

Compounds of formula I are distinguished by having valuable therapeutic properties. They can be used in the treatment or prevention of disorders, relating to allosteric modulators for the mGluR4 receptor.

The most preferred indications for compounds which are allosteric modulators for the mGluR4 receptor are Parkinson's disease, anxiety, emesis, obsessive compulsive disorder, anorexia, autism, neuroprotection, cancer, depression and type 2 diabetes.

The present invention relates to compounds of formula I and to their pharmaceutically acceptable salts, to these compounds as pharmaceutically active substances, to the processes for their production as well as to their use in the treatment or prevention of disorders, relating to allosteric modulators for the mGluR4 receptor, such as Parkinson's disease, anxiety, emesis, obsessive compulsive disorder, autism, neuroprotection, cancer, depression and diabetes type 2 and to pharmaceutical compositions containing the compounds of formula I.

A further object of the present invention is a method for the treatment or prophylaxis of Parkinson's disease, anxiety, emesis, obsessive compulsive disorder, anorexia, autism, neuroprotection, cancer, depression and type 2 diabetes, which method comprises administering an effective amount of a compound of formula I to a mammal in need.

Furthermore, the invention includes all racemic mixtures, all their corresponding enantiomers and/or optical isomers, or analogues containing isotopes of hydrogen, fluorine, carbon, oxygen or nitrogen.

The following definitions of the general terms used in the present description apply irrespective of whether the terms in question appear alone or in combination.

As used herein, the term "lower alkyl" denotes a saturated straight- or branched-chain group containing from 1 to 7 carbon atoms, for example, methyl, ethyl, propyl, isopropyl, n-butyl, i-butyl, 2-butyl, t-butyl and the like. Preferred alkyl groups are groups with 1-4 carbon atoms.

As used herein, the term "lower alkoxy" denotes a lower alkyl group as defined above, which is linked with an O atom.

As used herein, the term "lower alkyl substituted by halogen" denotes a lower alkyl group as defined above, wherein at least one hydrogen atom is replaced by halogen.

As used herein, the term "lower alkoxy substituted by halogen" denotes a lower alkoxy group as defined above, wherein at least one hydrogen atom is replaced by halogen.

A five or six-membered heteroaryl group is selected from the group:

A heterocycloalkyl group is selected from the group:

$R^5$ and $R^6$ are both methyl and the dotted line is a bond corresponds to compounds of formula:

IE $R^5$ and $R^6$ are both methyl and the dotted line is nothing corresponds to compounds of formula:

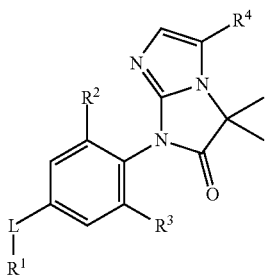

One of $R^5$ and $R^6$ is hydrogen and the other is methyl, and the dotted line is nothing corresponds to compounds of formula

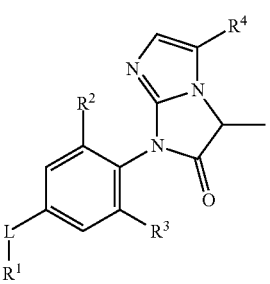

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

Preferred are compounds of formula I, wherein $R^2$ and R are both fluoro.

One embodiment of the invention are compounds of formula IA

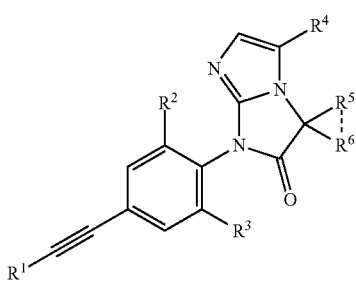

wherein
$R^1$ is phenyl or a five or six-membered heteroaryl group, optionally substituted by lower alkyl, lower alkyl substituted by halogen or lower alkoxy substituted by halogen;
$R^2$ is fluoro;
$R^3$ is fluoro or chloro;
$R^4$ is hydrogen, lower alkyl, halogen, lower alkyl substituted by hydroxy, $S(O)_2CH_3$, or is a five or six-membered heteroaryl group or a heterocycloalkyl group, which are optionally substituted by lower alkyl, hydroxy or =O;
$R^5$ and $R^6$ are both methyl and the dotted line is a bond, or $R^5$ and $R^6$ are both methyl and the dotted line is nothing, or one of $R^5$ and $R^6$ is hydrogen and the other is methyl, and the dotted line is nothing; or a pharmaceutically acceptable salt or acid addition salt, all possible tautomeric forms, a racemic mixture, or its corresponding enantiomer and/or optical isomer and/or stereoisomer thereof, for example the following compounds 3-[2,6-Difluoro-4-(2-phenylethynyl)phenyl]-2,3-dihydrospiro[[1,3]diazolo[1,2-a]imidazole-1,1'-cyclopropane]-2-one 1-(2-chloro-6-fluoro-4-(phenylethynyl)phenyl)-3,3-dimethyl-1H-imidazo[1,2-a]imidazol-2(3H)-one 1-(2,6-difluoro-4-(phenylethynyl)phenyl)-3-methyl-1H-imidazo[1,2-a]imidazol-2(3H)-one (enantiomer 1)

1-(2,6-difluoro-4-(phenylethynyl)phenyl)-3-methyl-1H-imidazo[1,2-a]imidazol-2(3H)-one (enantiomer 2)

1-(2,6-difluoro-4-(phenylethynyl)phenyl)-3,3-dimethyl-1H-imidazo[1,2-a]imidazol-2(3H)-one 7'-[2,6-difluoro-4-[2-(3-pyridyl)ethynyl]phenyl]spiro[cyclopropane-1,5'-imidazo[1,2-a]imidazole]-6'-one 1-(2,6-difluoro-4-(phenylethynyl)phenyl)-5-iodo-3,3-dimethyl-1H-imidazo[1,2-a]imidazol-2(3H)-one 3-[2,6-difluoro-4-(2-phenylethynyl)phenyl]-6-iodo-2,3-dihydrospiro[[1,3]diazolo[1,2-a]imidazole-1,1'-cyclopropane]-2-one 1-(2-chloro-6-fluoro-4-(phenylethynyl)phenyl)-5-iodo-3,3-dimethyl-1H-imidazo[1,2-a]imidazol-2(3H)-one 3-[2,6-Difluoro-4-(2-phenylethynyl)phenyl]-6-(pyridin-2-yl)-2,3-dihydrospiro[[1,3]diazolo[1,2-a]imidazole-1,1'-cyclopropane]-2-one 7'-[2,6-difluoro-4-(2-phenylethynyl)phenyl]-3'-(1-methylimidazol-4-yl)spiro[cyclopropane-1,5'-imidazo[1,2-a]imidazole]-6'-one 7'-[2,6-difluoro-4-[2-(3-pyridyl)ethynyl]phenyl]-3'-pyrimidin-4-yl-spiro[cyclopropane-1,5'-imidazo[1,2-a]imidazole]-6'-one 7'-[2,6-difluoro-4-[2-(3-pyridyl)ethynyl]phenyl]-3'-(2-pyridyl)spiro[cyclopropane-1,5'-imidazo[1,2-a]imidazole]-6'-one 3'-[2,6-Difluoro-4-(2-phenylethynyl)phenyl]-6'-(pyrimidin-4-yl)-2',3'-dihydrospiro[cyclopropane-1,1'-imidazo-[1,2-a][1,3]diazole]-2'-one 7'-[2,6-difluoro-4-[2-(3-pyridyl)ethynyl]phenyl]-3'-(1-methylimidazol-4-yl)spiro[cyclopropane-1,5'-imidazo[1,2-a]imidazole]-6'-one 3-[2,6-Difluoro-4-(2-phenylethynyl)phenyl]-6-phenyl-2,3-dihydrospiro[[1,3]diazolo[1,2-a]imidazole-1,1'-cyclopropane]-2-one 1'-(2,6-difluoro-4-(phenylethynyl)phenyl)-5'-(1-methyl-1H-pyrazol-3-yl)spiro[cyclopropane-1,3'-imidazo[1,2-a]imidazol]-2'(1'H)-one 3-[2,6-Difluoro-4-(2-phenylethynyl)phenyl]-6-(1H-pyrazol-3-yl)-2,3-dihydrospiro[[1,3]diazolo[1,2-a]-imidazole-1,1'-cyclopropane]-2-one 7'-[2,6-difluoro-4-[2-(3-pyridyl)ethynyl]phenyl]-3'-(1H-pyrazol-3-yl)spiro[cyclopropane-1,5'-imidazo[1,2-a]imidazole]-6'-one 3-[2,6-Difluoro-4-(2-phenylethynyl)phenyl]-6-(1-methyl-1H-pyrazol-4-yl)-2,3-dihydrospiro[[1,3]diazolo[1,2-a]imidazole-1,1'-cyclopropane]-2-one 7'-[2,6-difluoro-4-[2-(3-pyridyl)ethynyl]phenyl]-3'-(2-methylpyrazol-3-yl)spiro[cyclopropane-1,5'-imidazo[1,2-a]imidazole]-6'-one 1-(2,6-difluoro-4-(phenylethynyl)phenyl)-3,3-dimethyl-5-phenyl-1H-imidazo[1,2-a]imidazol-2(3H)-one 3-[2,6-Difluoro-4-(2-phenylethynyl)phenyl]-6-(pyridin-4-yl)-2,3-dihydrospiro[[1,3]diazolo[1,2-a]imidazole-1,1'-cyclopropane]-2-one 3-[2,6-Difluoro-4-(2-phenylethynyl)phenyl]-6-(pyridin-3-yl)-2,3-dihydrospiro[[1,3]diazolo[1,2-a]imidazole-1,1'-cyclopropane]-2-one 1-(2-chloro-6-fluoro-4-(phenylethynyl)phenyl)-3,3-dimethyl-5-(1-methyl-1H-pyrazol-4-yl)-1H-imidazo[1,2-a]imidazol-2(3H)-one 1-(2-chloro-6-fluoro-4-(phenylethynyl)phenyl)-3,3-dimethyl-5-(1-methyl-1H-pyrazol-3-yl)-1H-imidazo[1,2-a]imidazol-2(3H)-one 1'-(2,6-difluoro-4-(pyridin-3-ylethynyl)phenyl)-5'-(1-methyl-1H-pyrazol-4-yl)spiro[cyclopropane-1,3'-imidazo[1,2-a]imidazol]-2'(1'H)-one 3-[2,6-Difluoro-4-(2-phenylethynyl)phenyl]-6-(pyrimidin-5-yl)-2,3-dihydrospiro[[1,3]diazolo[1,2-a]imidazole-1,1'-cyclopropane]-2-one 1'-(2,6-difluoro-4-(pyridin-3-ylethynyl)phenyl)-5'-(pyridin-3-yl)spiro[cyclopropane-1,3'-imidazo[1,2-a]imidazol]-2'(1'H)-one 3-[2,6-Difluoro-4-(2-phenylethynyl)phenyl]-6-(1H-pyrazol-4-yl)-2,3-dihydrospiro[[1,3]diazolo[1,2-a]imidazole-1,1'-cyclopropane]-2-one 7'-[2,6-difluoro-4-(2-phenylethynyl)phenyl]-3'-(2-methylpyrazol-3-yl)spiro[cyclopropane-1,5'-imidazo[1,2-a]imidazole]-6'-one 7'-[2,6-difluoro-4-[2-(3-pyridyl)ethynyl]phenyl]-3'-(2-methylpyrazol-3-yl)spiro[cyclopropane-1,5'-imidazo[1,2-a]imidazole]-6'-one 3-[2,6-Difluoro-4-(2-phenylethynyl)phenyl]-6-methyl-2,3-dihydrospiro[[1,3]diazolo[1,2-a]imidazole-1,1'-cyclopropane]-2-one 7'-[2,6-difluoro-4-[2-(3-pyridyl)ethynyl]phenyl]-3'-methyl-spiro[cyclopropane-1,5'-imidazo[1,2-a]imidazole]-6'-one 7'-[2,6-difluoro-4-(2-phenylethynyl)phenyl]-3'-(3-hydroxyoxetan-3-yl)spiro[cyclopropane-1,5'-imidazo[1,2-a]imidazole]-6'-one 3'-[2,6-Difluoro-4-(2-phenylethynyl)phenyl]-6'-methanesulfonyl-2',3'-dihydrospiro[cyclopropane-1,1'-imidazo[1,2-a][1,3]diazole]-2'-one 7'-[2,6-difluoro-4-[2-(3-pyridyl)ethynyl]phenyl]-3'-(2-oxoazetidin-1-yl)spiro[cyclopropane-1,5'-imidazo[1,2-a]imidazole]-6'-one 7'-[2,6-difluoro-4-(2-phenylethynyl)phenyl]-3'-(hydroxymethyl)spiro[cyclopropane-1,5'-imidazo[1,2-a]imidazole]-6'-one or 7'-[2,6-difluoro-4-(2-phenylethynyl)phenyl]-3'-(1-hydroxyethyl)spiro[cyclopropane-1,5'-imidazo[1,2-a]imidazole]-6'-one.

One further object of the present invention are compounds of formulas IA-E, IA-F and IA-G.

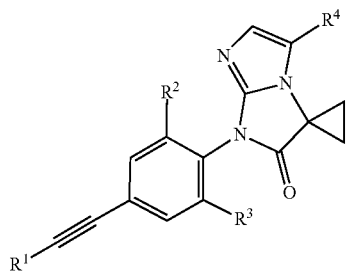

IA-E

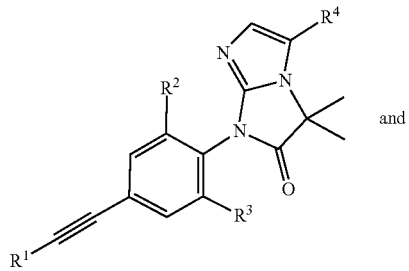

IA-F and

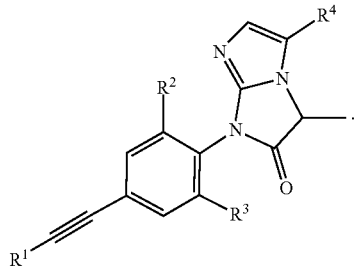

IA-G

One further object of the present invention are compounds of formula IB

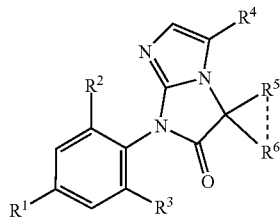

wherein
R¹ is phenyl or a five or six-membered heteroaryl group, optionally substituted by lower alkyl, lower alkyl substituted by halogen or lower alkoxy substituted by halogen;
R² is fluoro;
R³ is fluoro or chloro;
R⁴ is hydrogen, lower alkyl, halogen, lower alkyl substituted by hydroxy, S(O)₂CH₃, or is a five or six-membered heteroaryl group or a heterocycloalkyl group, which are optionally substituted by lower alkyl, hydroxy or =O;
R⁵ and R⁶ are both methyl and the dotted line is a bond, or
R⁵ and R⁶ are both methyl and the dotted line is nothing, or
one of R⁵ and R⁶ is hydrogen and the other is methyl, and the dotted line is nothing;

or a pharmaceutically acceptable salt or acid addition salt, all possible tautomeric forms, a racemic mixture, or its corresponding enantiomer and/or optical isomer and/or stereoisomer thereof, for example the following compounds 1'-(4'-(1,1-difluoroethyl)-3,5-difluoro-[1,1'-biphenyl]-4-yl)spiro[cyclopropane-1,3'-imidazo[1,2-a]imidazol]-2'(1'H)-one 7'-[4-(4-tert-butylpyrazol-1-yl)-2,6-difluoro-phenyl]-3'-pyrimidin-4-yl-spiro[cyclopropane-1,5'-imidazo[1,2-a]imidazole]-6'-one 7'-[4-(4-tert-butylpyrazol-1-yl)-2,6-difluoro-phenyl]-3'-(2-pyridyl)spiro[cyclopropane-1,5'-imidazo[1,2-a]imidazole]-6'-one 7'-[2,6-difluoro-4-[4-(trifluoromethyl)pyrazol-1-yl]phenyl]-3'-(2-pyridyl)spiro[cyclopropane-1,5'-imidazo[1,2-a]imidazole]-6'-one 7'-[2,6-difluoro-4-[4-(trifluoromethyl)pyrazol-1-yl]phenyl]-3'-pyrimidin-4-yl-spiro[cyclopropane-1,5'-imidazo[1,2-a]imidazole]-6'-one 1'-(4'-(1,1-difluoroethyl)-3,5-difluoro-[1,1'-biphenyl]-4-yl)-5'-(1-methyl-1H-pyrazol-4-yl)spiro[cyclopropane-1,3'-imidazo[1,2-a]imidazol]-2'(1'H)-one 1'-(4'-(1,1-difluoroethyl)-3,5-difluoro-[1,1'-biphenyl]-4-yl)-5'-(1H-pyrazol-3-yl)spiro[cyclopropane-1,3'-imidazo[1,2-a]imidazol]-2'(1'H)-one 7'-[2,6-difluoro-4-[4-(2,2,2-trifluoroethyl)piperazin-1-yl]phenyl]-3'-(1H-pyrazol-3-yl)spiro[cyclopropane-1,5'-imidazo[1,2-a]imidazole]-6'-one 7'-[4-[4-(difluoromethoxy)phenyl]-2,6-difluoro-phenyl]-3'-(1-methylpyrazol-3-yl)spiro[cyclopropane-1,5'-imidazo[1,2-a]imidazole]-6'-one 7'-[4-(4-tert-butylpyrazol-1-yl)-2,6-difluoro-phenyl]-3'-(3-hydroxyoxetan-3-yl)spiro[cyclopropane-1,5'-imidazo[1,2-a]imidazole]-6'-one 7'-[4-(4-tert-butylpyrazol-1-yl)-2,6-difluoro-phenyl]-3'-(1-hydroxyethyl)spiro[cyclopropane-1,5' imidazo[1,2-a]imidazole]-6'-one One further object of the present invention are compounds of formulas IB-E, IB-F and IB-G.

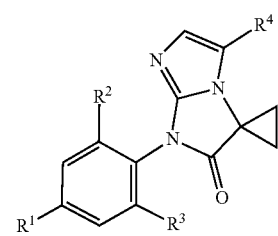

IB-E

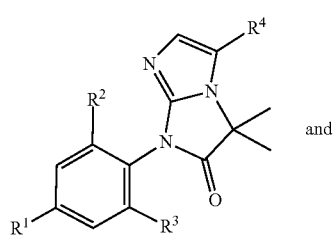

IB-F
and

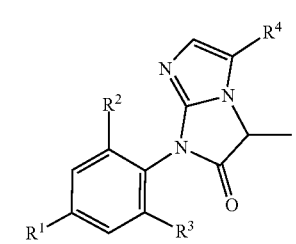

IB-G

One further object of the present invention are compounds of formula IC

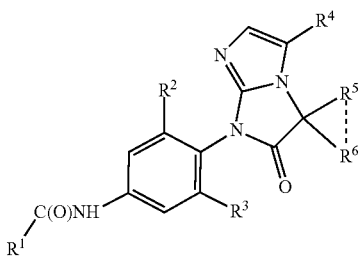

IC wherein

R$^1$ is phenyl or a five or six-membered heteroaryl group, optionally substituted by lower alkyl, lower alkyl substituted by halogen or lower alkoxy substituted by halogen;

R$^2$ is fluoro;

R$^3$ is fluoro or chloro;

R$^4$ is hydrogen, lower alkyl, halogen, lower alkyl substituted by hydroxy, $S(O)_2CH_3$, or is a five or six-membered heteroaryl group or a heterocycloalkyl group, which are optionally substituted by lower alkyl, hydroxy or =O;

R$^5$ and R$^6$ are both methyl and the dotted line is a bond, or

R$^5$ and R$^6$ are both methyl and the dotted line is nothing, or one of R$^5$ and R$^6$ is hydrogen and the other is methyl, and the dotted line is nothing;

or a pharmaceutically acceptable salt or acid addition salt, all possible tautomeric forms, a racemic mixture, or its corresponding enantiomer and/or optical isomer and/or stereoisomer thereof, for example the following compounds N-[3,5-difluoro-4-(6'-oxospiro[cyclopropane-1,5'-imidazo[1,2-a]imidazole]-7'-yl)phenyl]pyridine-2-carboxamide N-[3,5-difluoro-4-[6'-oxo-3'-(2-pyridyl)spiro[cyclopropane-1,5'-imidazo[1,2-a]imidazole]-7'-yl]phenyl]pyridine-2-carboxamide N-[3,5-difluoro-4-(6'-oxo-3'-pyrimidin-4-yl-spiro[cyclopropane-1,5'-imidazo[1,2-a]imidazole]-7'-yl)phenyl]pyridine-2-carboxamide N-[3,5-difluoro-4-[6'-oxo-3'-(1H-pyrazol-3-yl)spiro[cyclopropane-1,5'-imidazo[1,2-a]imidazole]-7'-yl]phenyl]pyridine-2-carboxamide N-[3,5-difluoro-4-(3'-methyl-6'-oxo-spiro[cyclopropane-1,5'-imidazo[1,2-a]imidazole]-7'-yl)phenyl]pyridine-2-carboxamide N-[3,5-difluoro-4-[3'-(3-hydroxyoxetan-3-yl)-6'-oxo-spiro[cyclopropane-1,5'-imidazo[1,2-a]imidazole]-7'-yl]phenyl]pyridine-2-carboxamide N-[3,5-difluoro-4-[3'-(hydroxymethyl)-6'-oxo-spiro[cyclopropane-1,5'-imidazo[1,2-a]imidazole]-7'-yl]phenyl]pyridine-2-carboxamide or N-[3,5-difluoro-4-[3'-(1-hydroxyethyl)-6'-oxo-spiro[cyclopropane-1,5'-imidazo[1,2-a]imidazole]-7'-yl]phenyl]pyridine-2-carboxamide.

One further object of the present invention are compounds of formulas IC-E, IC-F and IC-G.

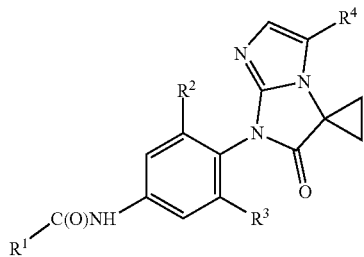

IC-E

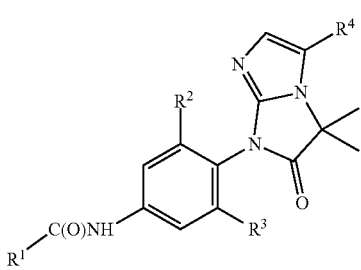

IC-F and

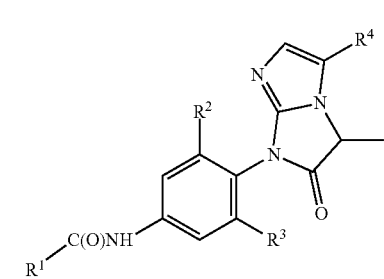

IC-G

One further object of the present invention are compounds of formula

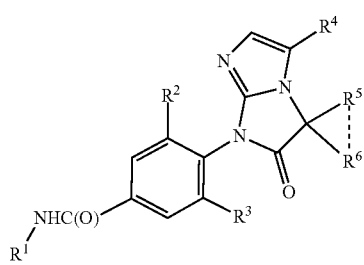

ID wherein
R¹ is phenyl or a five or six-membered heteroaryl group, optionally substituted by lower alkyl, lower alkyl substituted by halogen or lower alkoxy substituted by halogen;
R² is fluoro;
R³ is fluoro or chloro;
R⁴ is hydrogen, lower alkyl, halogen, lower alkyl substituted by hydroxy, S(O)₂CH₃, or is a five or six-membered heteroaryl group or a heterocycloalkyl group, which are optionally substituted by lower alkyl, hydroxy or =O;
R⁵ and R⁶ are both methyl and the dotted line is a bond, or R⁵ and R⁶ are both methyl and the dotted line is nothing, or
one of R⁵ and R⁶ is hydrogen and the other is methyl, and the dotted line is nothing;

or a pharmaceutically acceptable salt or acid addition salt, all possible tautomeric forms, a racemic mixture, or its corresponding enantiomer and/or optical isomer and/or stereoisomer thereof, for example the following compound
3,5-difluoro-4-[6'-oxo-3'-(2-pyridyl)spiro[cyclopropane-1, 5'-imidazo[1,2-a]imidazole]-7'-yl]-N-(2-pyridyl)benzamide.

One further object of the present invention are compounds of formulas ID-E, ID-F and ID-G.

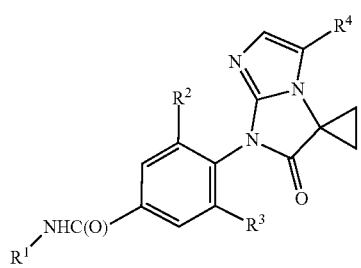

ID-E

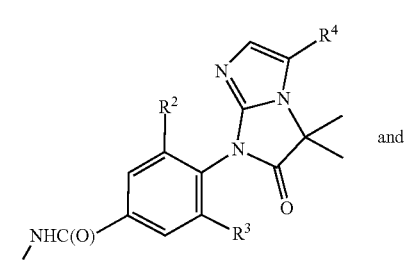

ID-F and

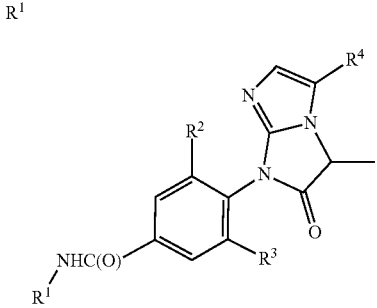

ID-G

The preparation of compounds of formula I of the present invention may be carried out in sequential or convergent synthetic routes. Syntheses of the compounds of the invention are shown in the following schemes 1 to 8. The skills required for carrying out the reaction and purification of the resulting products are known to those skilled in the art. The substituents and indices used in the following description of the processes have the significance given herein before.

The compounds of formula I can be manufactured by the methods given below, by the methods given in the examples or by analogous methods. Appropriate reaction conditions for the individual reaction steps are known to a person skilled in the art. The reaction sequence is not limited to the one displayed in the schemes, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

The present compounds of formula I and their pharmaceutically acceptable salts may be prepared by methods, known in the art, for example by the process variant described below, which process comprises a) reacting a compound of formula

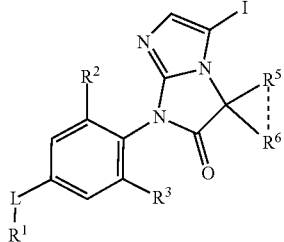

Ib with a suitable organometallic reagent of formula

R⁴-M for M being a boronic acid derivative (Suzuki reaction) or for M being stannane (Stille reaction). If necessary a protected organometallic derivative (e.g. N-Boc) may be used, followed by a suitable deprotection procedure, to a compound of formula

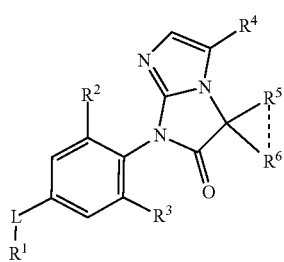

Ic wherein the substituents $R^1$, $R^2$, $R^3$, $R^5$ and $R^6$ are as defined in claim 1, and $R^4$ is methyl or a five or six membered heteroaryl group, and if desired, converting the compounds obtained into pharmaceutically acceptable acid addition salts, or b) reacting a compound of formula

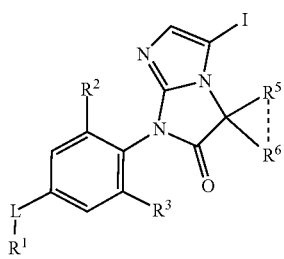

Ib with an alkyl magnesium bromide and then with

or methane sulfonyl chloride to a compound of formula

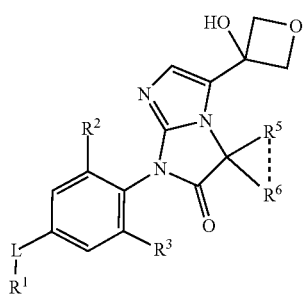

Ie wherein the substituents $R^1$, $R^2$, $R^3$, $R^5$ and $R^6$ are as defined in claim 1, and if desired, converting the compounds obtained into pharmaceutically acceptable acid addition salts, or c) reacting a compound of formula

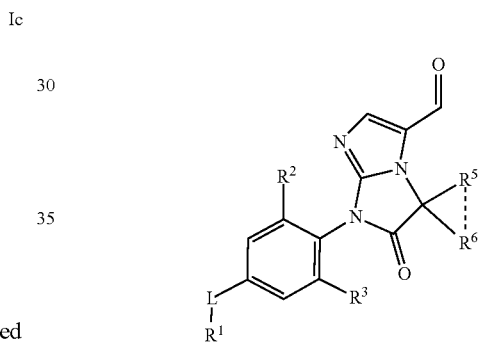

XIV with sodium borohydride (NaBH₄) or alkyl magnesium bromide (RMgBr for R=alkyl) to a compound of formula

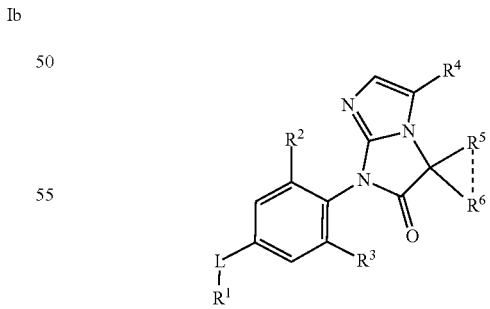

Id wherein the substituents $R^1$, $R^2$, $R^3$, $R^5$ and $R^6$ are as defined in claim 1, and $R^4$ is lower alkyl substituted by hydroxyl, and if desired, converting the compounds obtained into pharmaceutically acceptable acid addition salts, or d) reacting a compound of formula

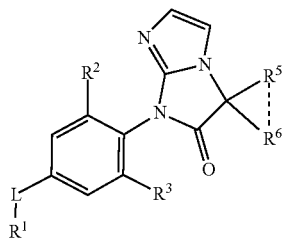

Ia with N-iodosuccinimide to a compound of formula

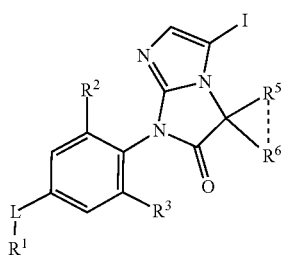

Ib wherein the substituents $R^1$, $R^2$, $R^3$, $R^5$ and $R^6$ are as defined in claim 1, and if desired, converting the compounds obtained into pharmaceutically acceptable acid addition salts, or e) reacting a compound of formula

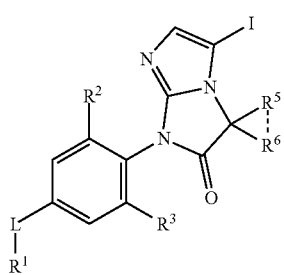

Ib with an amide of formula

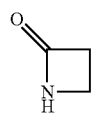

to a compound of formula

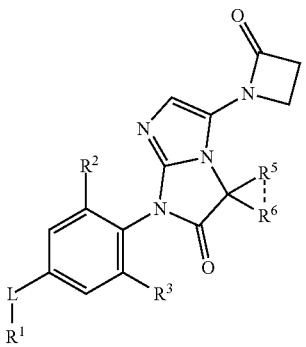

Ig wherein the substituents $R^1$, $R^2$, $R^3$, $R^5$ and $R^6$ are as defined in claim 1, and if desired, converting the compounds obtained into pharmaceutically acceptable acid addition salts, or f) reacting a compound of formula

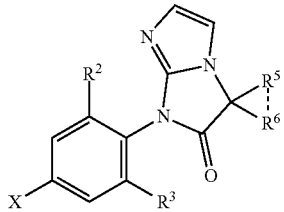

II where X is iodine or bromine, with $R^1$-L-H to give a compound of formula

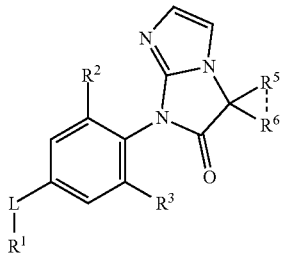

Ia wherein the substituents $R^1$, $R^2$, $R^3$, $R^5$ and $R^6$ are as defined in claim 1, and if desired, converting the compounds obtained into pharmaceutically acceptable acid addition salts, or g) reacting a compound of formula

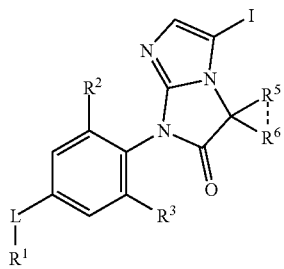

Ib with iPrMgCl and followed by addition of methane sulfonyl chloride to a compound of formula

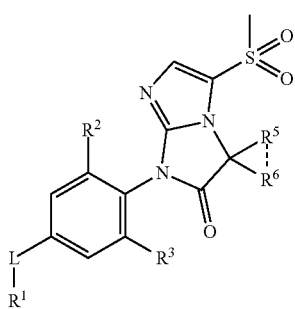

If wherein the substituents $R^1$, $R^2$, $R^3$, $R^5$ and $R^6$ are as defined in claim 1, and if desired, converting the compounds obtained into pharmaceutically acceptable acid addition salts.

The preparation of compounds of formula I is further described in more detail in schemes 1 to 8 and in examples 1-59.

Scheme 1

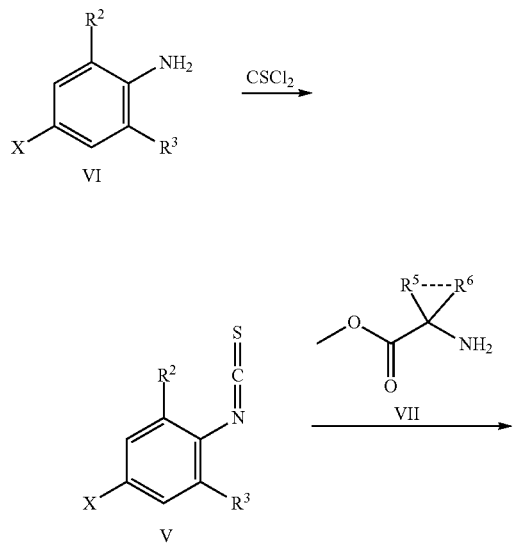

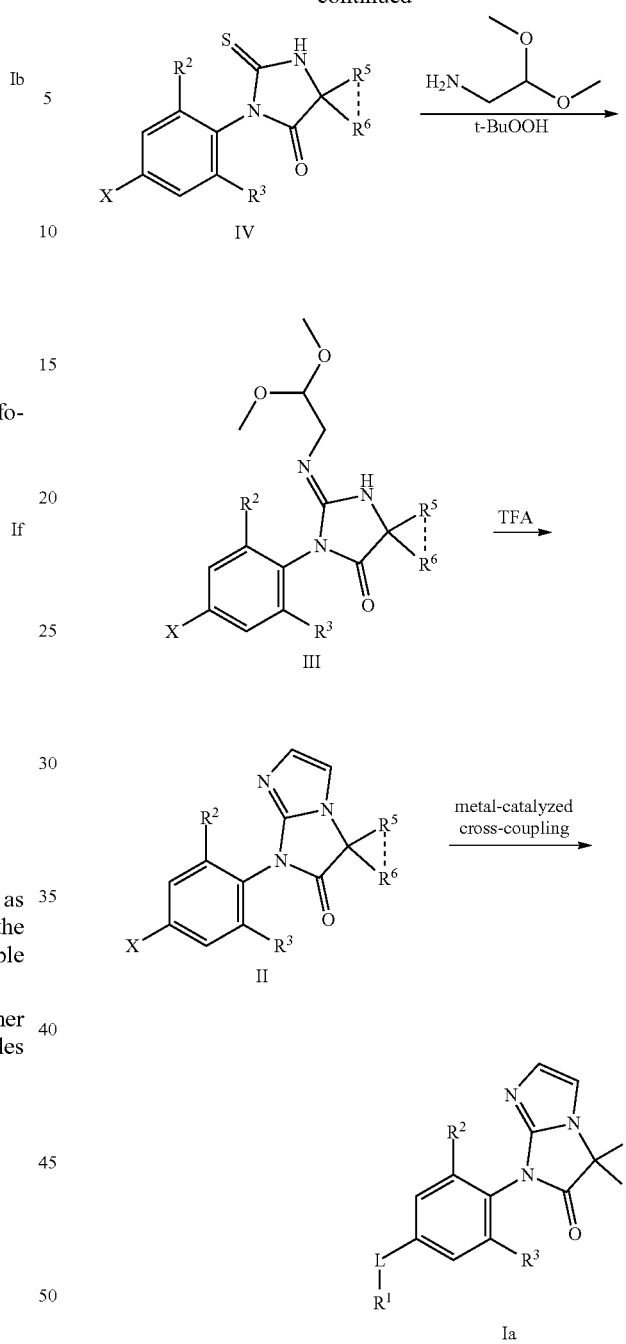

Compounds of formula I, where $R^4$=H, can be prepared from aryl halides (X=Br or I) of formula II with a suitable coupling partner in a transition metal catalysed cross coupling reaction like a Sonogashira reaction (with an alkyne), a Suzuki reaction (with a boronic acid derivative), a Buchwald reaction (with an amine), a carbonylative amination (with an amine) or a copper catalysed reaction (with an amide or a heteroarene). Aryl halides of formula II can be generated by reacting an aniline of formula VI with thiophosgene, followed by reaction with an aminoacid methyl ester of formula VII to give a thiourea of formula IV, condensation with 2,2-dimethoxy-ethylamine to give a compound of formula III, and treatment with TFA to give II.

Scheme 2

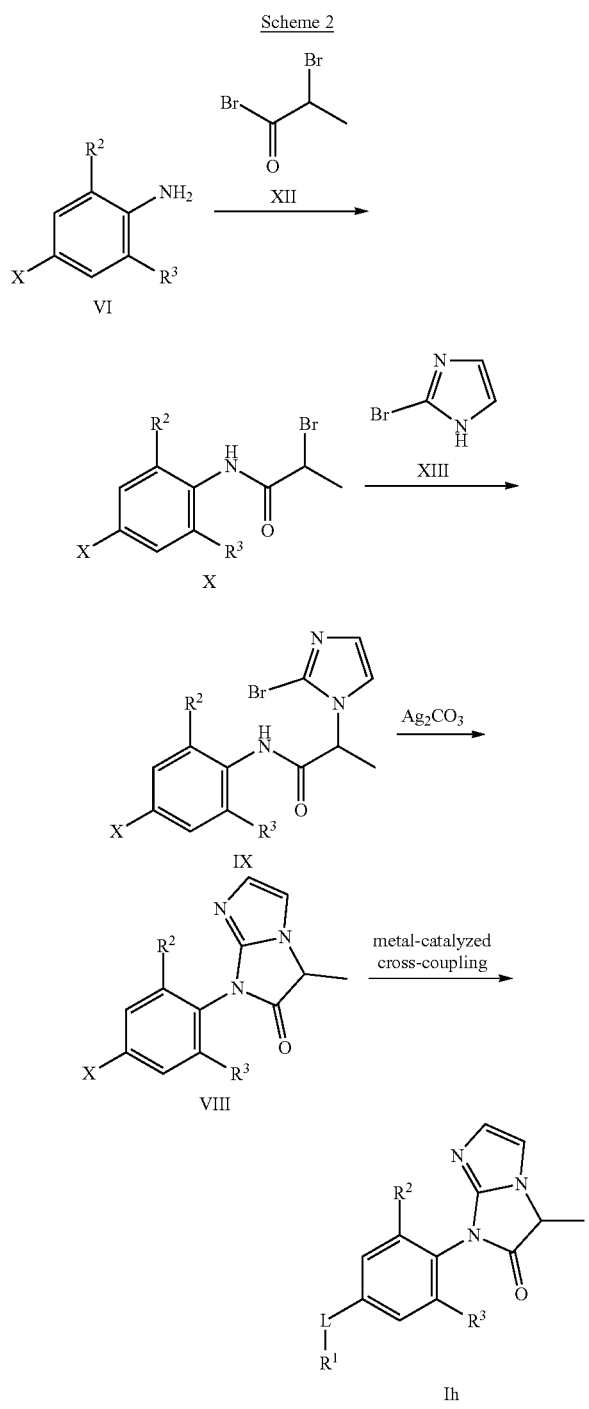

Scheme 3

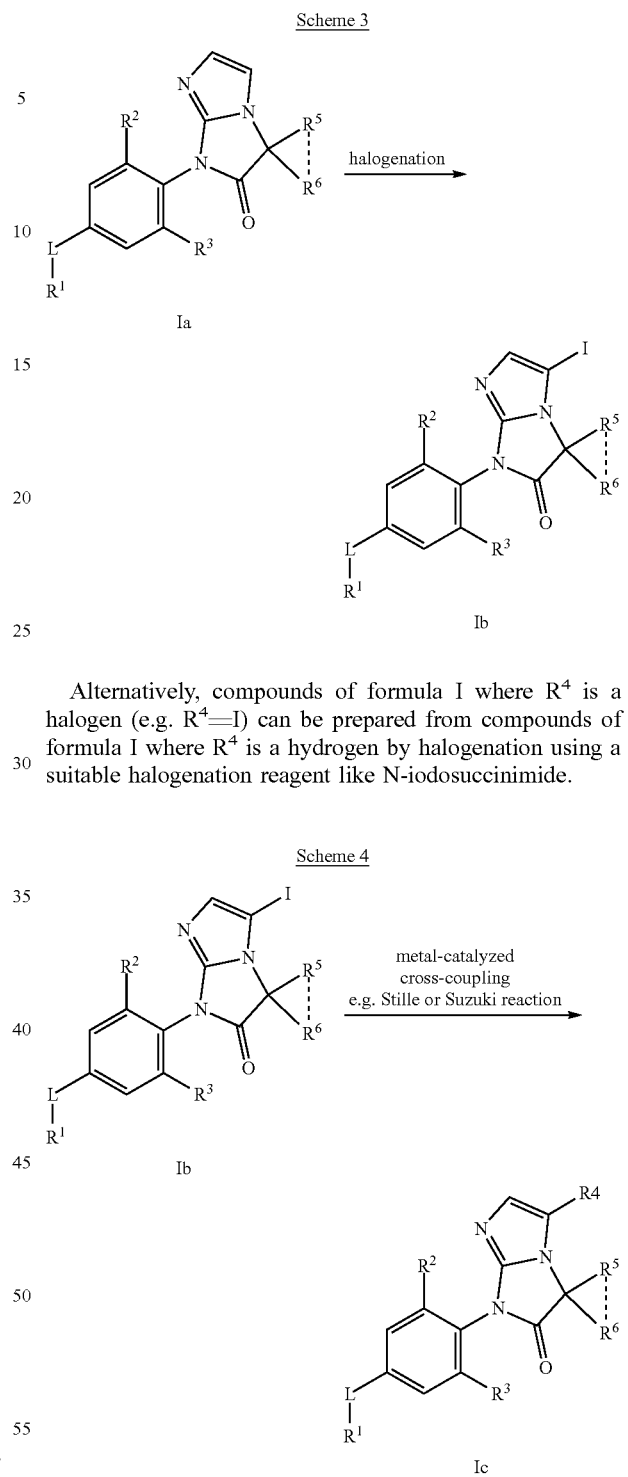

Alternatively, compounds of formula I where $R^4$ is a halogen (e.g. $R^4$=I) can be prepared from compounds of formula I where $R^4$ is a hydrogen by halogenation using a suitable halogenation reagent like N-iodosuccinimide.

Scheme 4

Alternatively, compounds of formula I where $R^4$ is methyl, an arene or a heteroarene can be prepared from compounds of formula I where $R^4$ is halogen (X=Br, I) using a transition metal catalysed cross coupling reaction such as a Suzuki reaction (with a (hetero)aryl boronic acid derivative or methyl boronic acid derivative) or a Stille reaction (with a (hetero)aryl stannane). If N-Boc protected heteroaryl derivatives are used these can be subsequently deprotected, for example using trifluoroacetic acid.

Alternatively, in analogy to Scheme 1, compounds of formula I where either $R^5$ or $R^6$ is hydrogen and the other is methyl, and the dotted line is nothing can be prepared from aryl halides (X=Br or I) of formula VIII. Aryl halides of formula VIII can be prepared by reacting an aniline of formula VI with 2-bromo-propionyl bromide to give an amide of formula X, followed by reaction with 2-bromo-imidazole to give an imidazole derivative of formula IX, followed by a Ag$_2$CO$_3$ mediated reaction to give VIII. Racemic mixtures of chiral compound VIII can be separated using chiral HPLC.

Scheme 5

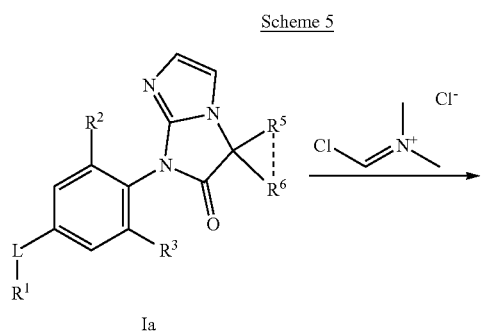

Ia

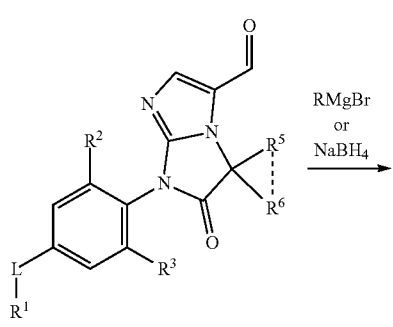

XIV

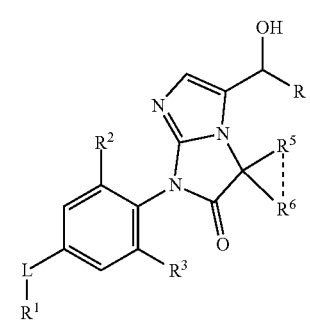

Id

Alternatively, compounds of formula I where R⁴ is an alcohol of formula —CH(OH)R, where R=H or alkyl can be prepared from compounds of formula I where R⁴ is a hydrogen by reaction with (chloromethylene)dimethyliminium chloride followed by aqueous workup to give an aldehyde of formula XIV, which can be reduced using a reducing agent like NaBH₄ or reacted with an organometallic reagent like an alkyl magnesiumbromide.

Scheme 6

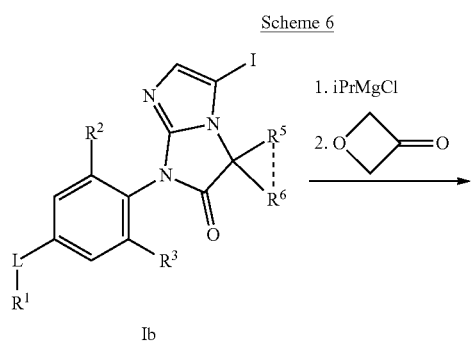

Ib

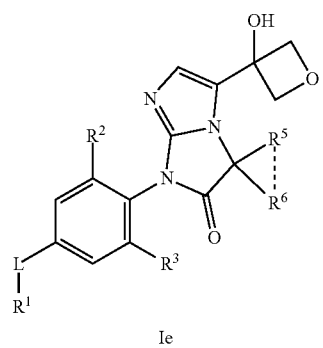

Ie

Alternatively, compounds of formula I where R⁴ is 3-hydroxyoxetan-3-yl can be prepared from compounds of formula I where R⁴ is iodine by reacting with a halogen exchange reagent like iPrMgCl to generate an anion equivalent followed by addition of 3-oxetanone.

Scheme 7

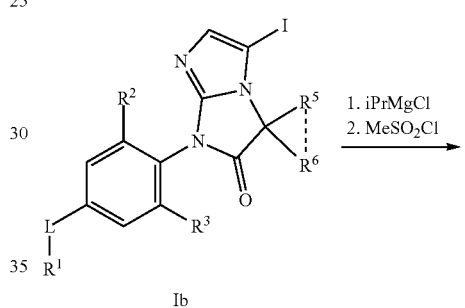

Ib

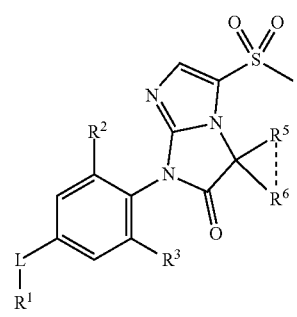

If

Alternatively, compounds of formula I where R⁴ is methanesulfonyl can be prepared from compounds of formula I where R⁴ is iodine by reacting with a halogen exchange reagent like iPrMgCl to generate an anion equivalent followed by addition of methanesulfonyl chloride.

Scheme 8

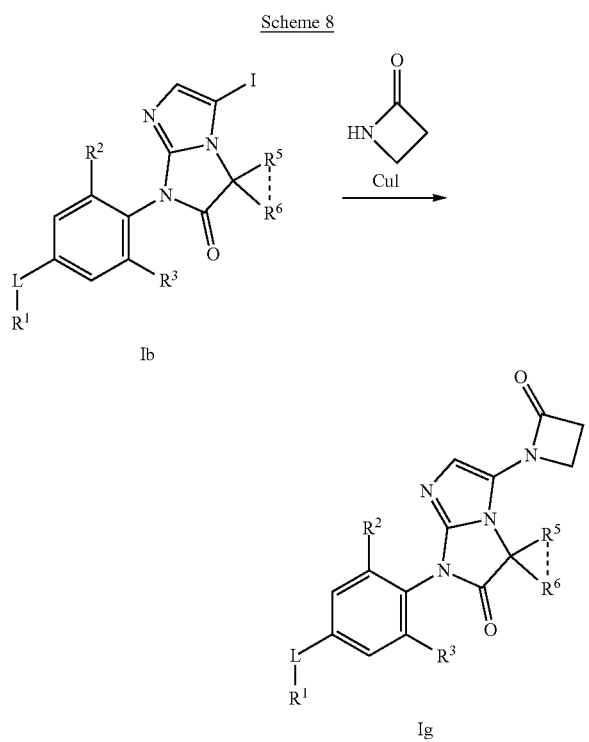

Alternatively, compounds of formula I where R⁴ is 2-oxoazetidin-1-yl can be prepared from compounds of formula I where R⁴ is iodine by reacting with azetidinone in a copper-catalyzed amination reaction.

Biological Assay and Data

Determination of $EC_{50}$ Values Using a Ca2+ Mobilization In Vitro Assay on Recombinant Human mGlu4 Expressed in HEK293 Cells:

A monoclonal HEK-293 cell line stably transfected with a cDNA encoding for the human mGlu4 receptor was generated; for the work with mGlu4 Positive Allosteric Modulators (PAMs), a cell line with low receptor expression levels and low constitutive receptor activity was selected to allow the differentiation of agonistic versus PAM activity. Cells were cultured according to standard protocols (Freshney, 2000) in Dulbecco's Modified Eagle Medium with high glucose supplemented with 1 mM glutamine, 10% (vol/vol) heat-inactivated bovine calf serum, Penicillin/Streptomycin, 50 µg/ml hygromycin and 15 µg/ml blasticidin (all cell culture reagents and antibiotics from Invitrogen, Basel, Switzerland).

About 24 hrs before an experiment, $5 \times 10^4$ cells/well were seeded in poly-D-lysine coated, black/clear-bottomed 96-well plates. The cells were loaded with 2.5 µM Fluo-4 AM in loading buffer (1×HBSS, 20 mM HEPES) for 1 hr at 37° C. and washed five times with loading buffer. The cells were transferred into a Functional Drug Screening System 7000 (Hamamatsu, Paris, France), and 11 half logarithmic serial dilutions of test compound at 37° C. were added and the cells were incubated for 10-30 min. with on-line recording of fluorescence. Following this pre-incubation step, the agonist (2S)-2-amino-4-phosphonobutanoic acid (L-AP4) was added to the cells at a concentration corresponding to $EC_{20}$ with on-line recording of fluorescence; in order to account for day-to-day variations in the responsiveness of cells, the $EC_{20}$ of L-AP4 was determined immediately ahead of each experiment by recording of a full dose-response curve of L-AP4.

Responses were measured as peak increase in fluorescence minus basal (i.e. fluorescence without addition of L-AP4), normalized to the maximal stimulatory effect obtained with saturating concentrations of L-AP4. Graphs were plotted with the % maximal stimulatory using XLfit, a curve fitting program that iteratively plots the data using Levenburg Marquardt algorithm. The single site competition analysis equation used was $y=A+((B-A)/(1+((x/C)D)))$, where y is the % maximal stimulatory effect, A is the minimum y, B is the maximum y, C is the $EC_{50}$, x is the log 10 of the concentration of the competing compound and D is the slope of the curve (the Hill Coefficient). From these curves the $EC_{50}$ (drug concentration at which 50% of the maximal receptor activation was achieved), the Hill coefficient as well as the maximal response in % of the maximal stimulatory effect obtained with saturating concentrations of L-AP4 were calculated (see Fig. 1).

Positive signals obtained during the pre-incubation with the PAM test compounds (i.e. before application of an $EC_{20}$ concentration of L-AP4) were indicative of an agonistic activity, the absence of such signals were demonstrating the lack of agonistic activities. A depression of the signal observed after addition of the $EC_{20}$ concentration of L-AP4 was indicative of an inhibitory activity of the test compound.

List of Examples and Data

| Expl. | Structure | Name | $EC_{50}$ (uM) mGlu4 PAM |
|---|---|---|---|
| 1 | 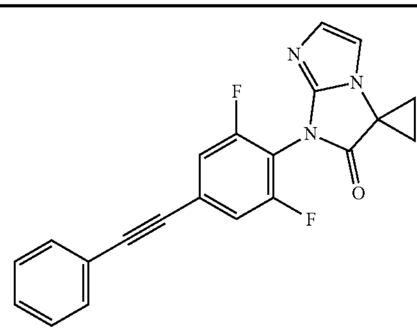 | 3-[2,6-Difluoro-4-(2-phenylethynyl)phenyl]-2,3-dihydrospiro[[1,3]diazolo[1,2-a]imidazole-1,1'-cyclopropane]-2-one | 0.178 |

-continued

| Expl. | Structure | Name | EC$_{50}$ (uM) mGlu4 PAM |
|---|---|---|---|
| 2 | 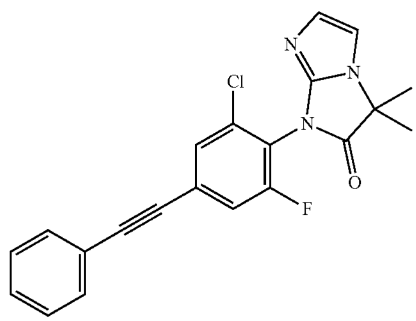 [SMILES: CC1(C)C(=O)N(c2c(F)cc(C#Cc3ccccc3)cc2F)c2nccn21] | 1-(2-chloro-6-fluoro-4-(phenylethynyl)phenyl)-3,3-dimethyl-1H-imidazo[1,2-a]imidazol-2(3H)-one | 0.359 |
| 3 | enantiomer 1 | 1-(2,6-difluoro-4-(phenylethynyl)phenyl)-3-methyl-1H-imidazo[1,2-a]imidazol-2(3H)-one (enantiomer 1) | 0.453 |
| 4 | enantiomer 2 | 1-(2,6-difluoro-4-(phenylethynyl)phenyl)-3-methyl-1H-imidazo[1,2-a]imidazol-2(3H)-one (enantiomer 2) | 0.758 |
| 5 | 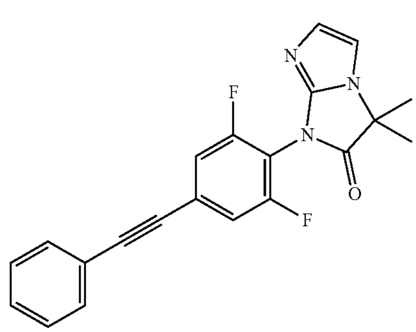 | 1-(2,6-difluoro-4-(phenylethynyl)phenyl)-3,3-dimethyl-1H-imidazo[1,2-a]imidazol-2(3H)-one | 0.468 |

-continued

| Expl. | Structure | Name | EC$_{50}$ (uM) mGlu4 PAM |
|---|---|---|---|
| 6 | 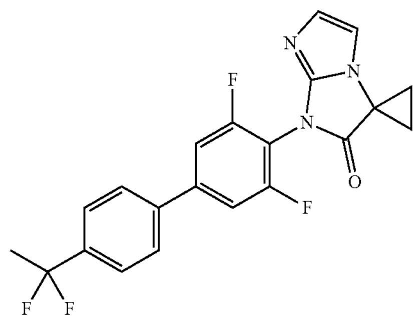 [SMILES: CC(F)(F)c1ccc(-c2cc(F)c(N3C(=O)C4(CC4)n4ccnc43)c(F)c2)cc1] | 1'-(4'-(1,1-difluoroethyl)-3,5-difluoro-[1,1'-biphenyl]-4-yl)spiro[cyclopropane-1,3'-imidazo[1,2-a]imidazol]-2'(1'H)-one | 0.383 |
| 7 | 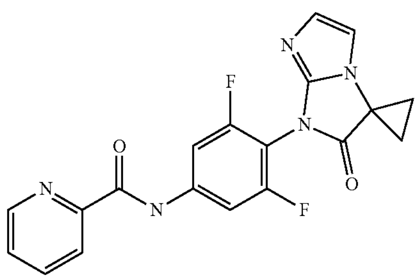 [SMILES: O=C(Nc1cc(F)c(N2C(=O)C3(CC3)n3ccnc32)c(F)c1)c1ccccn1] | N-[3,5-difluoro-4-(6'-oxospiro[cyclopropane-1,5'-imidazo[1,2-a]imidazole]-7'-yl)phenyl]pyridine-2-carboxamide | 0.541 |
| 8 | 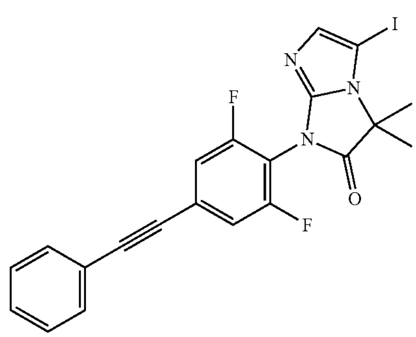 [SMILES: CC1(C)C(=O)N(c2c(F)cc(C#Cc3ccccc3)cc2F)c2ncc(I)n21] | 1-(2,6-difluoro-4-(phenylethynyl)phenyl)-5-iodo-3,3-dimethyl-1H-imidazo[1,2-a]imidazol-2(3H)-one | 0.418 |
| 9 | 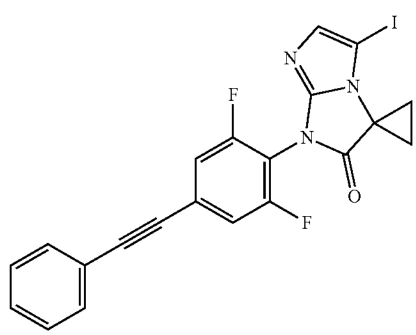 [SMILES: O=C1N(c2c(F)cc(C#Cc3ccccc3)cc2F)c2ncc(I)n2C12CC2] | 3-[2,6-difluoro-4-(2-phenylethynyl)phenyl]-6-iodo-2,3-dihydrospiro[[1,3]diazolo[1,2-a]imidazole-1,1'-cyclopropane]-2-one | 0.245 |

-continued

| Expl. | Structure | Name | EC$_{50}$ (uM) mGlu4 PAM |
|---|---|---|---|
| 10 | 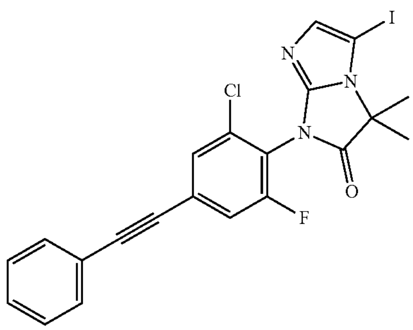 [SMILES: CC1(C)C(=O)N(c2c(F)cc(C#Cc3ccccc3)cc2Cl)c2ncc(I)n21] | 1-(2-chloro-6-fluoro-4-(phenylethynyl)phenyl)-5-iodo-3,3-dimethyl-1H-imidazo[1,2-a]imidazol-2(3H)-one | 0.371 |
| 11 | 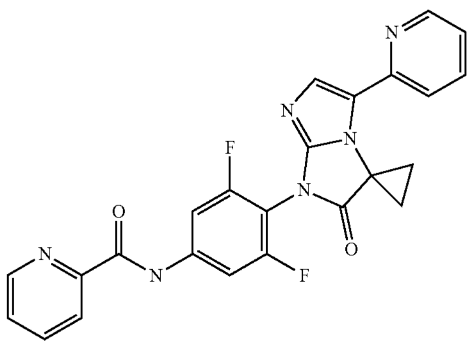 [SMILES: O=C(Nc1cc(F)c(N2C(=O)C3(CC3)n3c(-c4ccccn4)cnc32)c(F)c1)c1ccccn1] | N-[3,5-difluoro-4-[6'-oxo-3'-(2-pyridyl)spiro[cyclopropane-1,5'-imidazo[1,2-a]imidazole]-7'-yl]phenyl]pyridine-2-carboxamide | 0.059 |
| 12 | 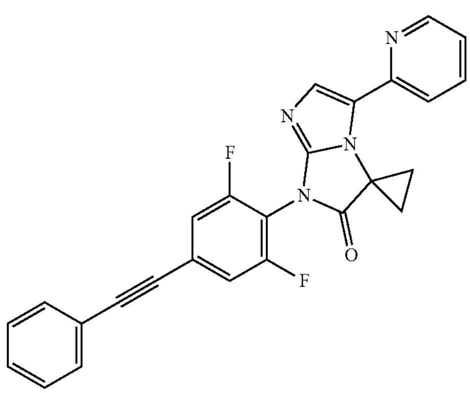 [SMILES: O=C1N(c2c(F)cc(C#Cc3ccccc3)cc2F)c2ncc(-c3ccccn3)n2C12CC2] | 3-[2,6-Difluoro-4-(2-phenylethynyl)phenyl]-6-(pyridin-2-yl)-2,3-dihydrospiro[[1,3]diazolo[1,2-a]imidazole-1,1'-cyclopropane]-2-one | 0.076 |
| 13 | 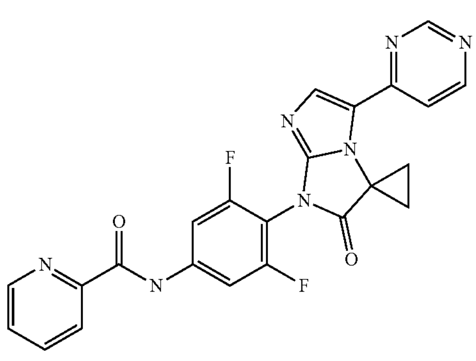 [SMILES: O=C(Nc1cc(F)c(N2C(=O)C3(CC3)n3c(-c4ccncn4)cnc32)c(F)c1)c1ccccn1] | N-[3,5-difluoro-4-(6'-oxo-3'-pyrimidin-4-yl-spiro[cyclopropane-1,5'-imidazo[1,2-a]imidazole]-7'-yl)phenyl]pyridine-2-carboxamide | 0.077 |

-continued

| Expl. | Structure | Name | EC$_{50}$ (uM) mGlu4 PAM |
|---|---|---|---|
| 14 | 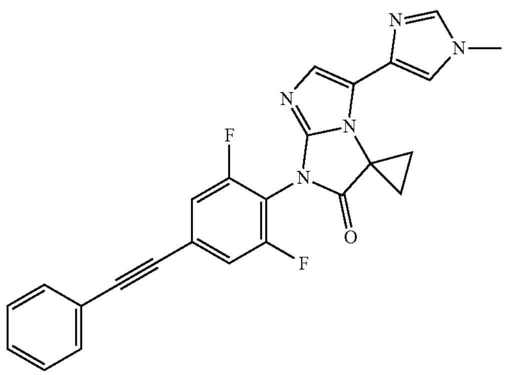 [SMILES: Cn1cnc(-c2cnc3n2C2(CC2)C(=O)N3c2c(F)cc(C#Cc3ccccc3)cc2F)c1] | 7'-[2,6-difluoro-4-(2-phenylethynyl)phenyl]-3'-(1-methylimidazol-4-yl)spiro[cyclopropane-1,5'-imidazo[1,2-a]imidazole]-6'-one | 0.120 |
| 15 | 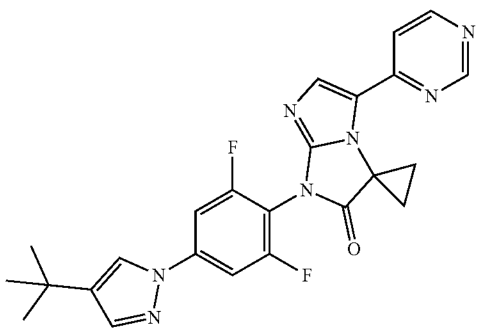 [SMILES: CC(C)(C)c1cnn(-c2cc(F)c(N3C(=O)C4(CC4)n4c(-c5ccncn5)cnc43)c(F)c2)c1] | 7'-[4-(4-tert-butylpyrazol-1-yl)-2,6-difluoro-phenyl]-3'-pyrimidin-4-yl-spiro[cyclopropane-1,5'-imidazo[1,2-a]imidazole]-6'-one | 0.232 |
| 16 | 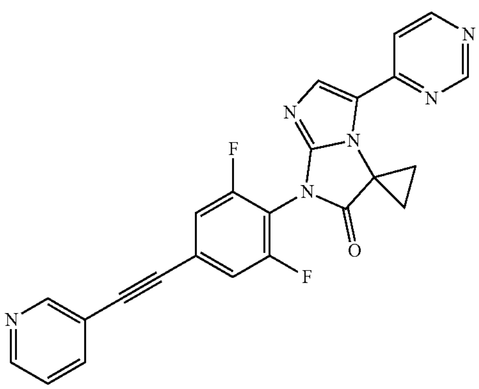 [SMILES: O=C1N(c2c(F)cc(C#Cc3cccnc3)cc2F)c2ncc(-c3ccncn3)n2C12CC2] | 7'-[2,6-difluoro-4-[2-(3-pyridyl)ethynyl]phenyl]-3'-pyrimidin-4-yl-spiro[cyclopropane-1,5'-imidazo[1,2-a]imidazole]-6'-one | 0.237 |
| 17 | 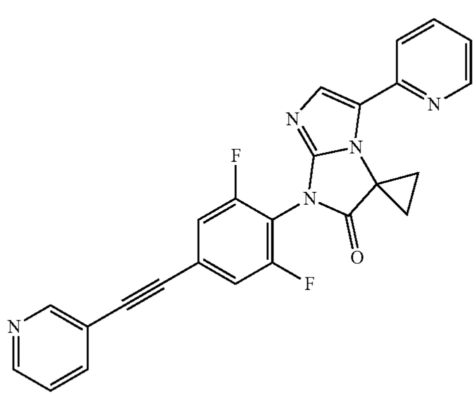 [SMILES: O=C1N(c2c(F)cc(C#Cc3cccnc3)cc2F)c2ncc(-c3ccccn3)n2C12CC2] | 7'-[2,6-difluoro-4-[2-(3-pyridyl)ethynyl]phenyl]-3'-(2-pyridyl)spiro[cyclopropane-1,5'-imidazo[1,2-a]imidazole]-6'-one | 0.283 |

-continued

| Expl. | Structure | Name | EC₅₀ (uM) mGlu4 PAM |
|---|---|---|---|
| 18 | 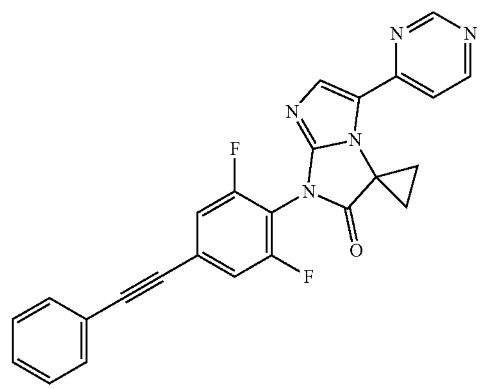 | 3'-[2,6-Difluoro-4-(2-phenylethynyl)phenyl]-6'-(pyrimidin-4-yl)-2',3'-dihydrospiro[cyclopropane-1,1'-imidazo-[1,2-a][1,3]diazole]-2'-one | 0.361 |
| 19 | 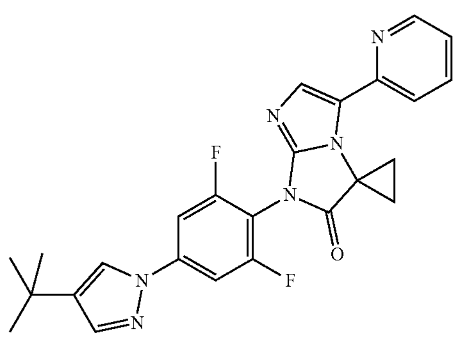 [SMILES: CC(C)(C)c1cnn(-c2cc(F)c(N3C(=O)C4(CC4)n4c(-c5ccccn5)cnc43)c(F)c2)c1] | 7'-[4-(4-tert-butylpyrazol-1-yl)-2,6-difluoro-phenyl]-3'-(2-pyridyl)spiro[cyclopropane-1,5'-imidazo[1,2-a]imidazole]-6'-one | 0.426 |
| 20 | 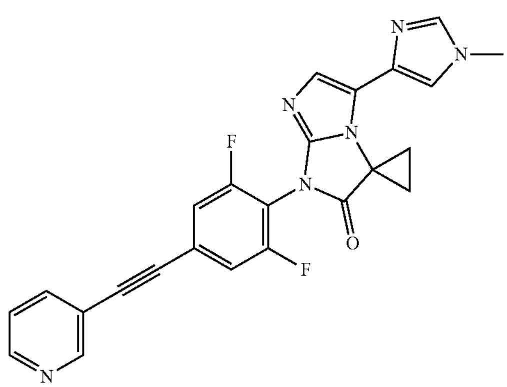 [SMILES: Cn1cnc(-c2cnc3n2C2(CC2)C(=O)N3c2c(F)cc(C#Cc3cccnc3)cc2F)c1] | 7'-[2,6-difluoro-4-[2-(3-pyridyl)ethynyl]phenyl]-3'-(1-methylimidazol-4-yl)spiro[cyclopropane-1,5'-imidazo[1,2-a]imidazole]-6'-one | 0.442 |
| 21 | 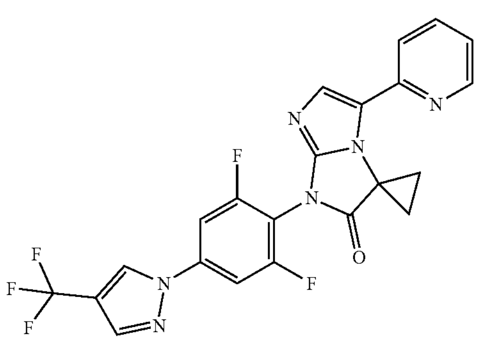 [SMILES: O=C1N(c2c(F)cc(-n3cc(C(F)(F)F)cn3)cc2F)c2ncc(-c3ccccn3)n2C12CC2] | 7'-[2,6-difluoro-4-[4-(trifluoromethyl)pyrazol-1-yl]phenyl]-3'-(2-pyridyl)spiro[cyclopropane-1,5'-imidazo[1,2-a]imidazole]-6'-one | 0.596 |

-continued

| Expl. | Structure | Name | EC$_{50}$ (uM) mGlu4 PAM |
|---|---|---|---|
| 22 | 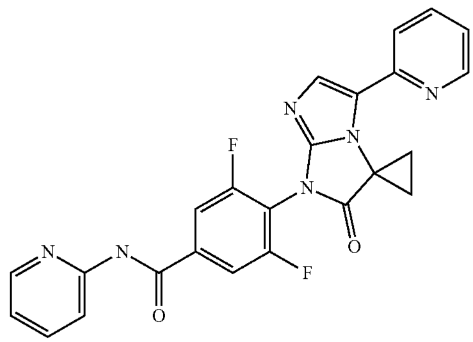 [SMILES: O=C(Nc1ccccn1)c1cc(F)c(N2C(=O)C3(CC3)n3c(-c4ccccn4)cnc32)c(F)c1] | 3,5-difluoro-4-[6'-oxo-3'-(2-pyridyl)spiro[cyclopropane-1,5'-imidazo[1,2-a]imidazole]-7'-yl]-N-(2-pyridyl)benzamide | 0.610 |
| 23 | 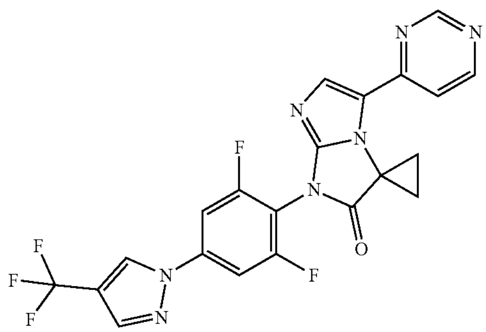 [SMILES: O=C1N(c2c(F)cc(-n3cc(C(F)(F)F)cn3)cc2F)c2ncc(-c3ccncn3)n2C12CC2] | 7'-[2,6-difluoro-4-[4-(trifluoromethyl)pyrazol-1-yl]phenyl]-3'-pyrimidin-4-yl-spiro[cyclopropane-1,5'-imidazo[1,2-a]imidazole]-6'-one | 0.755 |
| 24 | 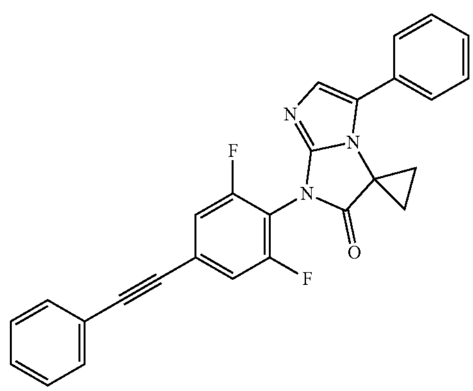 [SMILES: O=C1N(c2c(F)cc(C#Cc3ccccc3)cc2F)c2ncc(-c3ccccc3)n2C12CC2] | 3-[2,6-Difluoro-4-(2-phenylethynyl)phenyl]-6-phenyl-2,3-dihydrospiro[[1,3]diazolo[1,2-a]imidazole-1,1'-cyclopropane]-2-one | 0.073 |
| 25 | 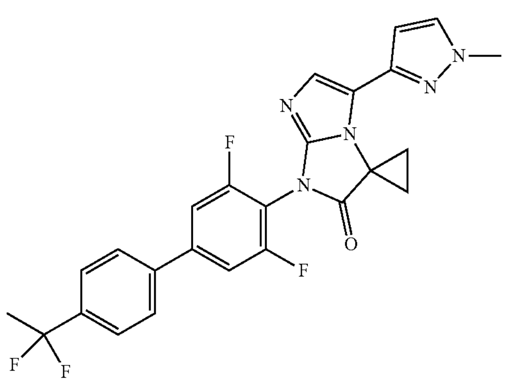 [SMILES: Cn1ccc(-c2cnc3n2C2(CC2)C(=O)N3c2c(F)cc(-c3ccc(C(C)(F)F)cc3)cc2F)n1] | N-[3,5-difluoro-4-(6'-oxo-3'-pyrimidin-4-yl-spiro[cyclopropane-1,5'-imidazo[1,2-a]imidazole]-7'-yl)phenyl]pyridine-2-carboxamide | 0.100 |

-continued

| Expl. | Structure | Name | EC₅₀ (uM) mGlu4 PAM |
|---|---|---|---|
| 26 | 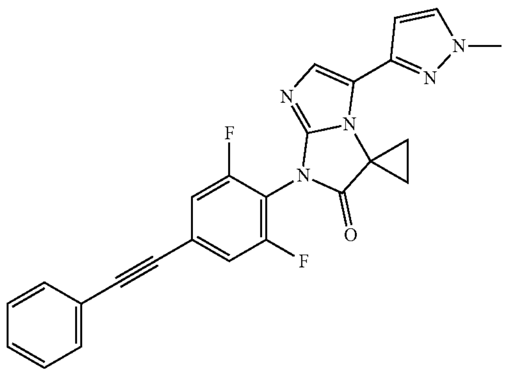 [SMILES: Cn1ccc(-c2cnc3n2C2(CC2)C(=O)N3c2c(F)cc(C#Cc3ccccc3)cc2F)n1] | 1'-(2,6-difluoro-4-(phenylethynyl)phenyl)-5'-(1-methyl-1H-pyrazol-3-yl)spiro[cyclopropane-1,3'-imidazo[1,2-a]imidazol]-2'(1'H)-one | 0.104 |
| 27 | 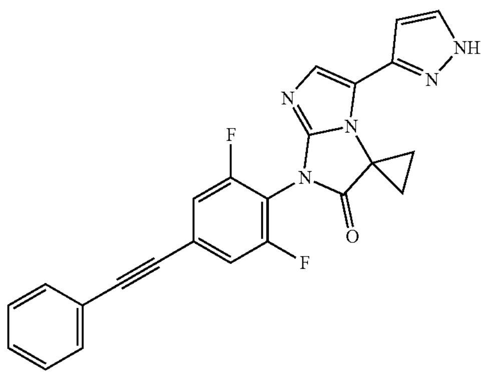 [SMILES: O=C1N(c2c(F)cc(C#Cc3ccccc3)cc2F)c2ncc(-c3cc[nH]n3)n2C12CC2] | 3-[2,6-Difluoro-4-(2-phenylethynyl)phenyl]-6-(1H-pyrazol-3-yl)-2,3-dihydrospiro[[1,3]diazolo[1,2-a]-imidazole-1,1'-cyclopropane]-2-one | 0.121 |
| 28 | 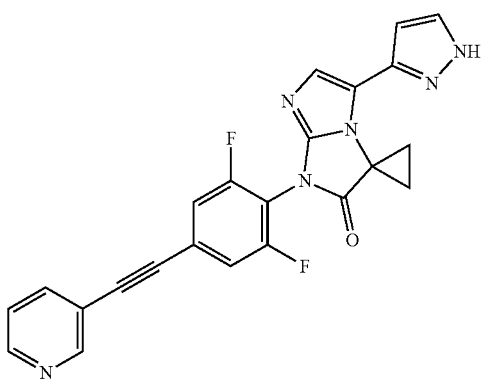 [SMILES: O=C1N(c2c(F)cc(C#Cc3cccnc3)cc2F)c2ncc(-c3cc[nH]n3)n2C12CC2] | 7'-[2,6-difluoro-4-[2-(3-pyridyl)ethynyl]phenyl]-3'-(1H-pyrazol-3-yl)spiro[cyclopropane-1,5'-imidazo[1,2-a]imidazole]-6'-one | 0.135 |
| 29 | 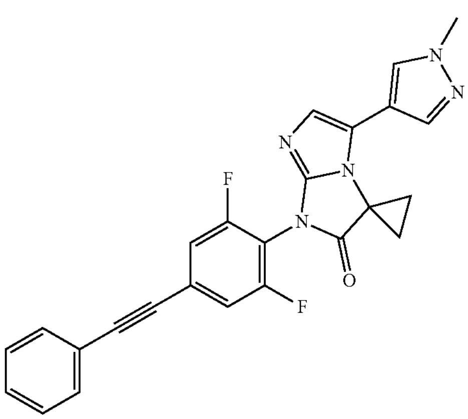 [SMILES: Cn1cc(-c2cnc3n2C2(CC2)C(=O)N3c2c(F)cc(C#Cc3ccccc3)cc2F)cn1] | 3-[2,6-Difluoro-4-(2-phenylethynyl)phenyl]-6-(1-methyl-1H-pyrazol-4-yl)-2,3-dihydrospiro[[1,3]diazolo[1,2-a]imidazole-1,1'-cyclopropane]-2-one | 0.139 |

-continued

| Expl. | Structure | Name | EC$_{50}$ (uM) mGlu4 PAM |
|---|---|---|---|
| 30 | 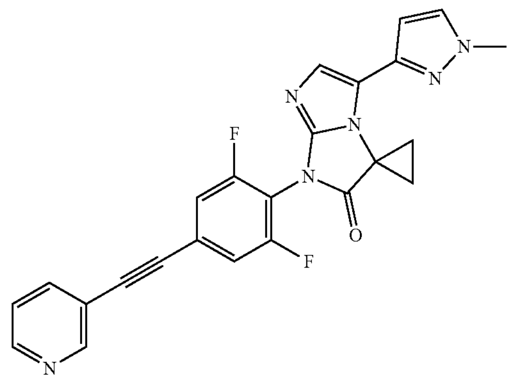 [SMILES: Cn1ccc(-c2cnc3n2C2(CC2)C(=O)N3c2c(F)cc(C#Cc3cccnc3)cc2F)n1] | 7'-[2,6-difluoro-4-[2-(3-pyridyl)ethynyl]phenyl]-3'-(2-methylpyrazol-3-yl)spiro[cyclopropane-1,5'-imidazo[1,2-a]imidazole]-6'-one | 0.143 |
| 31 | 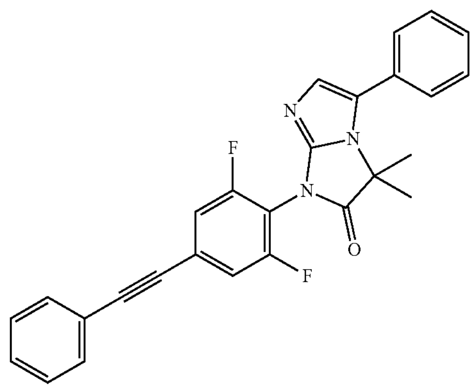 [SMILES: CC1(C)C(=O)N(c2c(F)cc(C#Cc3ccccc3)cc2F)c2ncc(-c3ccccc3)n21] | 1-(2,6-difluoro-4-(phenylethynyl)phenyl)-3,3-dimethyl-5-phenyl-1H-imidazo[1,2-a]imidazol-2(3H)-one | 0.243 |
| 32 | 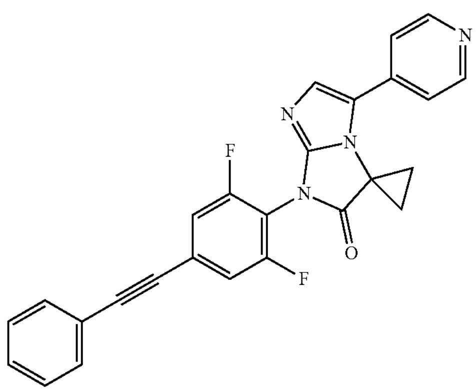 [SMILES: O=C1N(c2c(F)cc(C#Cc3ccccc3)cc2F)c2ncc(-c3ccncc3)n2C12CC2] | 3-[2,6-Difluoro-4-(2-phenylethynyl)phenyl]-6-(pyridin-4-yl)-2,3-dihydrospiro[[1,3]diazolo[1,2-a]imidazole-1,1'-cyclopropane]-2-one | 0.156 |
| 33 | 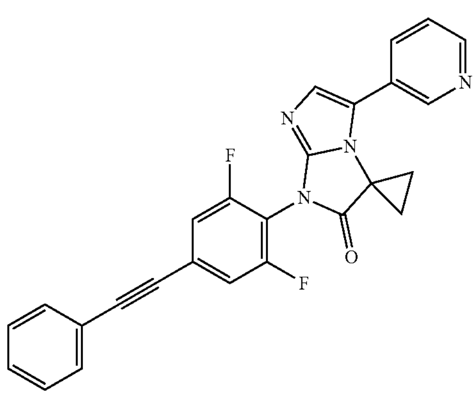 [SMILES: O=C1N(c2c(F)cc(C#Cc3ccccc3)cc2F)c2ncc(-c3cccnc3)n2C12CC2] | 3-[2,6-Difluoro-4-(2-phenylethynyl)phenyl]-6-(pyridin-3-yl)-2,3-dihydrospiro[[1,3]diazolo[1,2-a]imidazole-1,1'-cyclopropane]-2-one | 0.178 |

-continued

| Expl. | Structure | Name | EC$_{50}$ (uM) mGlu4 PAM |
|---|---|---|---|
| 34 | 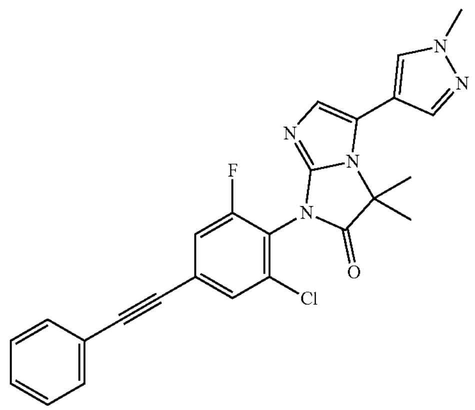 [SMILES: Cn1cc(-c2cnc3n2C(C)(C)C(=O)N3c2c(F)cc(C#Cc3ccccc3)cc2Cl)cn1] | 1-(2-chloro-6-fluoro-4-(phenylethynyl)phenyl)-3,3-dimethyl-5-(1-methyl-1H-pyrazol-4-yl)-1H-imidazo[1,2-a]imidazol-2(3H)-one | 0.195 |
| 35 | 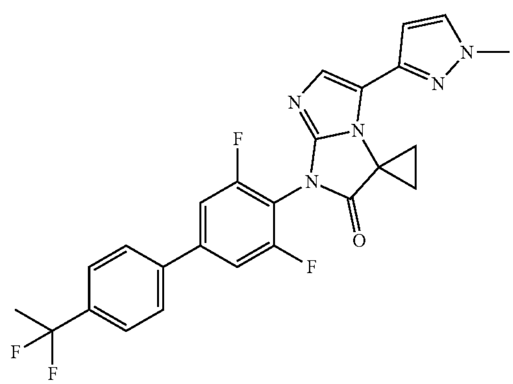 [SMILES: Cn1ccc(-c2cnc3n2C2(CC2)C(=O)N3c2c(F)cc(-c3ccc(C(C)(F)F)cc3)cc2F)n1] | 1'-(4'-(1,1-difluoroethyl)-3,5-difluoro-[1,1'-biphenyl]-4-yl)-5'-(1-methyl-1H-pyrazol-4-yl)spiro[cyclopropane-1,3'-imidazo[1,2-a]imidazol]-2'(1'H)-one | 0.227 |
| 36 | 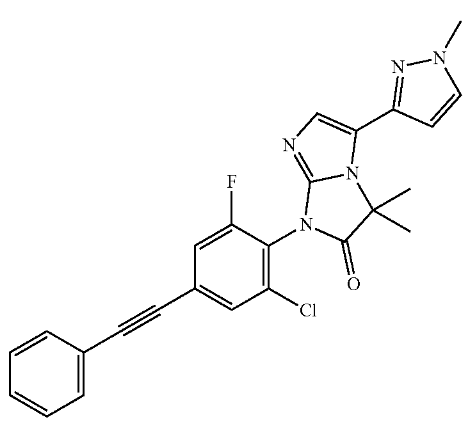 [SMILES: Cn1ccc(-c2cnc3n2C(C)(C)C(=O)N3c2c(F)cc(C#Cc3ccccc3)cc2Cl)n1] | 1-(2-chloro-6-fluoro-4-(phenylethynyl)phenyl)-3,3-dimethyl-5-(1-methyl-1H-pyrazol-3-yl)-1H-imidazo[1,2-a]imidazol-2(3H)-one | 0.252 |

-continued

| Expl. | Structure | Name | EC$_{50}$ (uM) mGlu4 PAM |
|---|---|---|---|
| 37 | 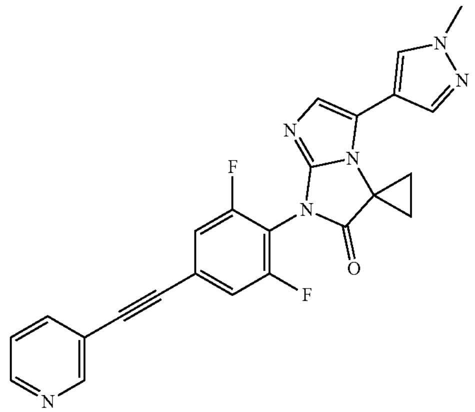 [SMILES: Cn1cc(-c2cnc3n2C2(CC2)C(=O)N3c2c(F)cc(C#Cc3cccnc3)cc2F)cn1] | 1'-(2,6-difluoro-4-(pyridin-3-ylethynyl)phenyl)-5'-(1-methyl-1H-pyrazol-4-yl)spiro[cyclopropane-1,3'-imidazo[1,2-a]imidazol]-2'(1'H)-one | 0.229 |
| 38 | 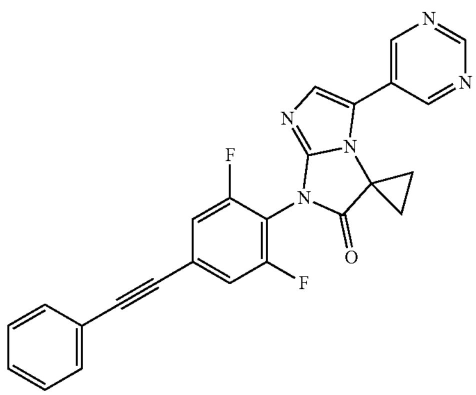 [SMILES: O=C1N(c2c(F)cc(C#Cc3ccccc3)cc2F)c2ncc(-c3cncnc3)n2C12CC2] | 3-[2,6-Difluoro-4-(2-phenylethynyl)phenyl]-6-(pyrimidin-5-yl)-2,3-dihydrospiro[[1,3]diazolo[1,2-a]imidazole-1,1'-cyclopropane]-2-one | 0.331 |
| 39 | 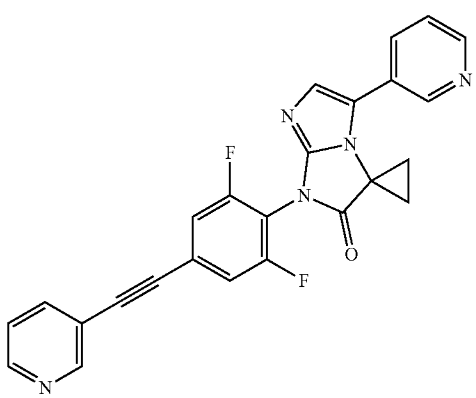 | 1'-(2,6-difluoro-4-(pyridin-3-ylethynyl)phenyl)-5'-(pyridin-3-yl)spiro[cyclopropane-1,3'-imidazo[1,2-a]imidazol]-2'(1'H)-one | 0.566 |
| 40 | 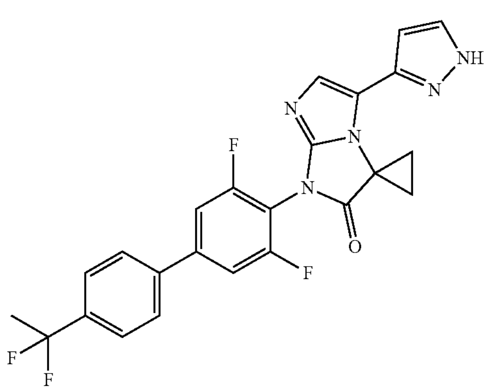 [SMILES: CC(F)(F)c1ccc(-c2cc(F)c(N3C(=O)C4(CC4)n4c(-c5cc[nH]n5)cnc43)c(F)c2)cc1] | 1'-(4'-(1,1-difluoroethyl)-3,5-difluoro-[1,1'-biphenyl]-4-yl)-5'-(1H-pyrazol-3-yl)spiro[cyclopropane-1,3'-imidazo[1,2-a]imidazol]-2'(1'H)-one | 0.206 |

-continued

| Expl. | Structure | Name | EC$_{50}$ (uM) mGlu4 PAM |
|---|---|---|---|
| 41 | 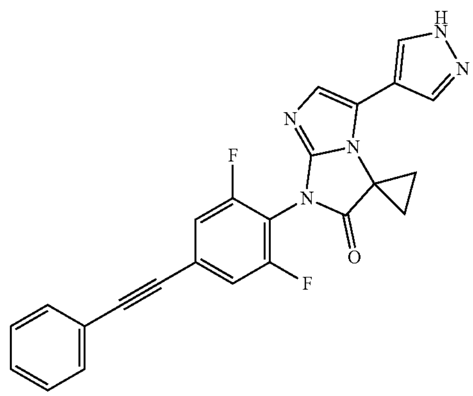 [SMILES: O=C1N(c2c(F)cc(C#Cc3ccccc3)cc2F)c2ncc(-c3cn[nH]c3)n2C12CC2] | 3-[2,6-Difluoro-4-(2-phenylethynyl)phenyl]-6-(1H-pyrazol-4-yl)-2,3-dihydrospiro[[1,3]diazolo[1,2-a]imidazole-1,1'-cyclopropane]-2-one | 0.238 |
| 42 | 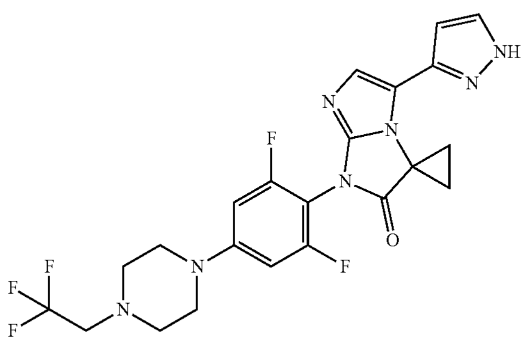 [SMILES: O=C1N(c2c(F)cc(N3CCN(CC(F)(F)F)CC3)cc2F)c2ncc(-c3cc[nH]n3)n2C12CC2] | 7'-[2,6-difluoro-4-[4-(2,2,2-trifluoroethyl)piperazin-1-yl]phenyl]-3'-(1H-pyrazol-3-yl)spiro[cyclopropane-1,5'-imidazo[1,2-a]imidazole]-6'-one | 0.417 |
| 43 | 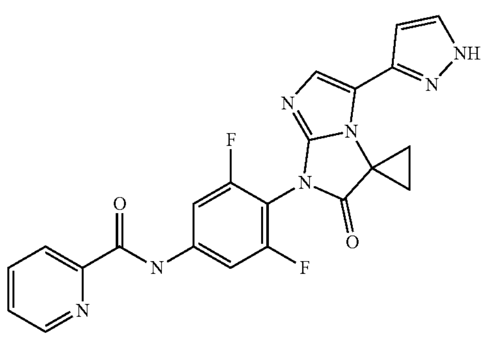 [SMILES: O=C(Nc1cc(F)c(N2C(=O)C3(CC3)n3c(-c4cc[nH]n4)cnc32)c(F)c1)c1ccccn1] | N-[3,5-difluoro-4-[6'-oxo-3'-(1H-pyrazol-3-yl)spiro[cyclopropane-1,5'-imidazo[1,2-a]imidazole]-7'-yl]phenyl]pyridine-2-carboxamide | 0.015 |
| 44 | 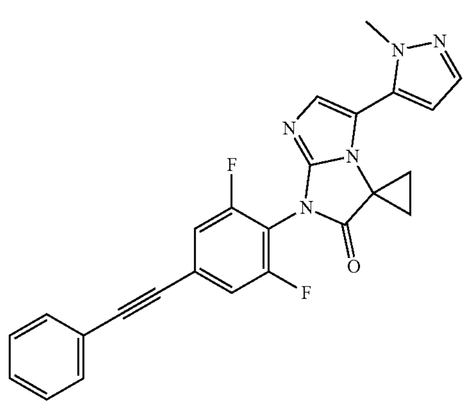 [SMILES: Cn1nccc1-c1cnc2n1C1(CC1)C(=O)N2c1c(F)cc(C#Cc2ccccc2)cc1F] | 7'-[2,6-difluoro-4-(2-phenylethynyl)phenyl]-3'-(2-methylpyrazol-3-yl)spiro[cyclopropane-1,5'-imidazo[1,2-a]imidazole]-6'-one | 0.422 |

-continued

| Expl. | Structure | Name | EC$_{50}$ (uM) mGlu4 PAM |
|---|---|---|---|
| 45 | 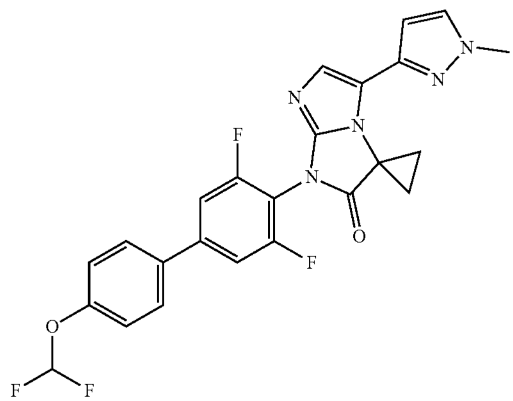 [SMILES: Cn1ccc(-c2cnc3n2C2(CC2)C(=O)N3c2c(F)cc(-c3ccc(OC(F)F)cc3)cc2F)n1] | 7'-[4-[4-(difluoromethoxy)phenyl]-2,6-difluoro-phenyl]-3'-(1-methylpyrazol-3-yl)spiro[cyclopropane-1,5'-imidazo[1,2-a]imidazole]-6'-one | 0.621 |
| 46 | 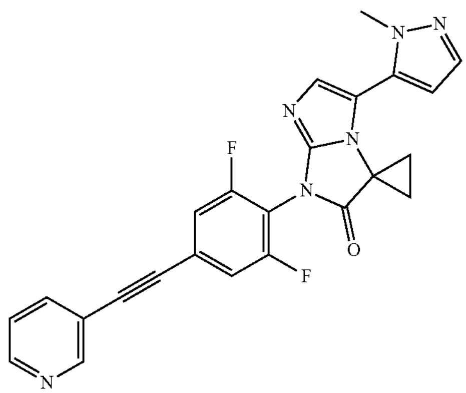 [SMILES: Cn1nccc1-c1cnc2n1C1(CC1)C(=O)N2c1c(F)cc(C#Cc2cccnc2)cc1F] | 7'-[2,6-difluoro-4-[2-(3-pyridyl)ethynyl]phenyl]-3'-(2-methylpyrazol-3-yl)spiro[cyclopropane-1,5'-imidazo[1,2-a]imidazole]-6'-one | 0.673 |
| 47 | 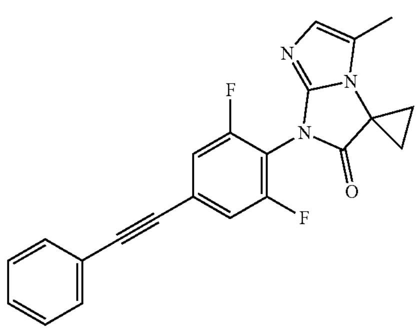 [SMILES: Cc1cnc2n1C1(CC1)C(=O)N2c1c(F)cc(C#Cc2ccccc2)cc1F] | 3-[2,6-Difluoro-4-(2-phenylethynyl)phenyl]-6-methyl-2,3-dihydrospiro[[1,3]diazolo[1,2-a]imidazole-1,1'-cyclopropane]-2-one | 0.181 |
| 48 | 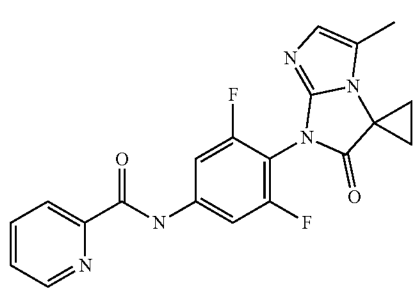 [SMILES: Cc1cnc2n1C1(CC1)C(=O)N2c1c(F)cc(NC(=O)c2ccccn2)cc1F] | N-[3,5-difluoro-4-(3'-methyl-6'-oxo-spiro[cyclopropane-1,5'-imidazo[1,2-a]imidazole]-7'-yl)phenyl]pyridine-2-carboxamide | 0.377 |

-continued

| Expl. | Structure | Name | EC₅₀ (uM) mGlu4 PAM |
|---|---|---|---|
| 49 | 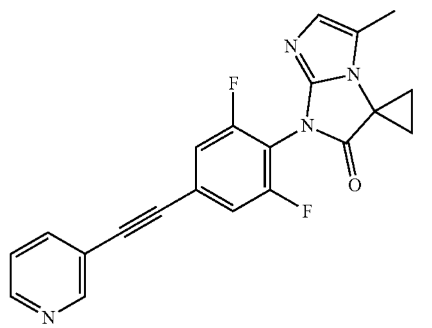 [SMILES: Cc1cnc2n1C1(CC1)C(=O)N2c1c(F)cc(C#Cc2cccnc2)cc1F] | 7'-[2,6-difluoro-4-[2-(3-pyridyl)ethynyl]phenyl]-3'-methyl-spiro[cyclopropane-1,5'-imidazo[1,2-a]imidazole]-6'-one | 0.829 |
| 50 | 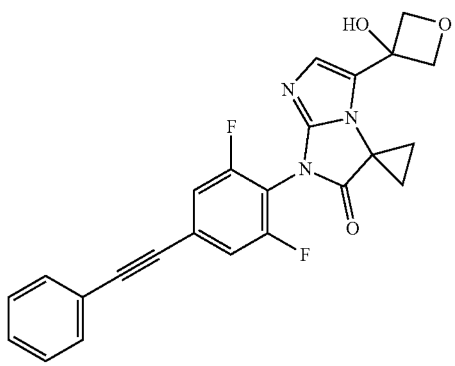 [SMILES: O=C1N(c2c(F)cc(C#Cc3ccccc3)cc2F)c2ncc(C3(O)COC3)n2C12CC2] | 7'-[2,6-difluoro-4-(2-phenyl ethynyl)phenyl]-3'-(3-hydroxyoxetan-3-yl)spiro[cyclopropane-1,5'-imidazo[1,2-a]imidazole]-6'-one | 0.322 |
| 51 | 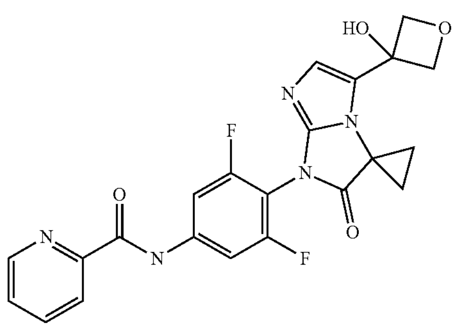 [SMILES: O=C(Nc1cc(F)c(N2C(=O)C3(CC3)n3c(C4(O)COC4)cnc32)c(F)c1)c1ccccn1] | N-[3,5-difluoro-4-[3'-(3-hydroxyoxetan-3-yl)-6'-oxo-spiro[cyclopropane-1,5'-imidazo[1,2-a]imidazole]-7'-yl]phenyl]pyridine-2-carboxamide | 0.363 |
| 52 | 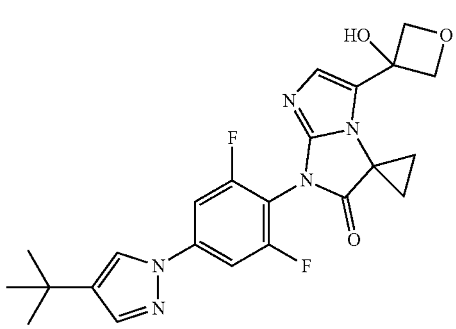 [SMILES: CC(C)(C)c1cnn(-c2cc(F)c(N3C(=O)C4(CC4)n4c(C5(O)COC5)cnc43)c(F)c2)c1] | 7'-[4-(4-tert-butylpyrazol-1-yl)-2,6-difluoro-phenyl]-3'-(3-hydroxyoxetan-3-yl)spiro[cyclopropane-1,5'-imidazo[1,2-a]imidazole]-6'-one | 0.905 |

-continued

| Expl. | Structure | Name | EC$_{50}$ (uM) mGlu4 PAM |
|---|---|---|---|
| 53 | 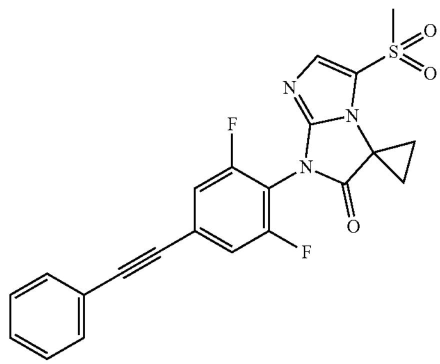 [SMILES: CS(=O)(=O)c1cnc2n1C1(CC1)C(=O)N2c1c(F)cc(C#Cc2ccccc2)cc1F] | 3'-[2,6-Difluoro-4-(2-phenylethynyl)phenyl]-6'-methanesulfonyl-2',3'-dihydrospiro[cyclopropane-1,1'-imidazo[1,2-a][1,3]diazole]-2'-one | 0.690 |
| 54 | 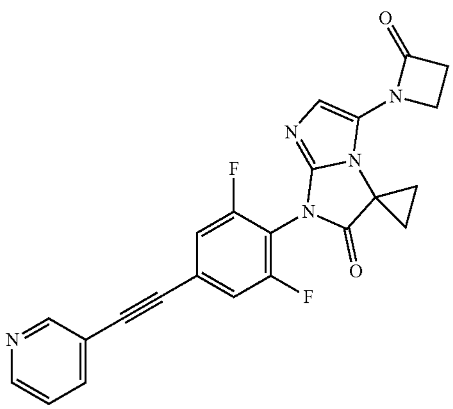 [SMILES: O=C1CCN1c1cnc2n1C1(CC1)C(=O)N2c1c(F)cc(C#Cc2cccnc2)cc1F] | 7'-[2,6-difluoro-4-[2-(3-pyridyl)ethynyl]phenyl]-3'-(2-oxoazetidin-1-yl)spiro[cyclopropane-1,5'-imidazo[1,2-a]imidazole]-6'-one | 0.808 |
| 55 | 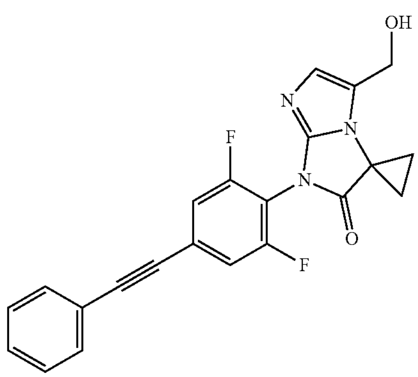 [SMILES: O=C1N(c2c(F)cc(C#Cc3ccccc3)cc2F)c2ncc(CO)n2C12CC2] | 7'-[2,6-difluoro-4-(2-phenylethynyl)phenyl]-3'-(hydroxymethyl)spiro[cyclopropane-1,5'-imidazo[1,2-a]imidazole]-6'-one | 0.294 |
| 56 | 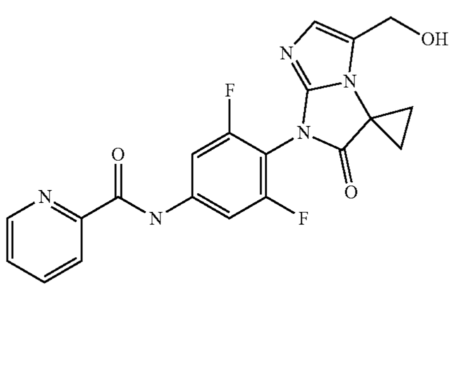 [SMILES: O=C(Nc1cc(F)c(N2C(=O)C3(CC3)n3c(CO)cnc32)c(F)c1)c1ccccn1] | N-[3,5-difluoro-4-[3'-(hydroxymethyl)-6'-oxo-spiro[cyclopropane-1,5'-imidazo[1,2-a]imidazole]-7'-yl]phenyl]pyridine-2-carboxamide | 0.834 |

| Expl. | Structure | Name | EC$_{50}$ (uM) mGlu4 PAM |
|---|---|---|---|
| 57 | 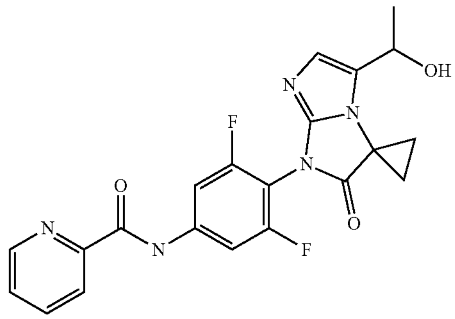 [SMILES: CC(O)c1cnc2n1C1(CC1)C(=O)N2c1c(F)cc(NC(=O)c2ccccn2)cc1F] | N-[3,5-difluoro-4-[3'-(1-hydroxyethyl)-6'-oxo-spiro[cyclopropane-1,5'-imidazo[1,2-a]imidazole]-7'-yl]phenyl]pyridine-2-carboxamide | 0.572 |
| 58 | 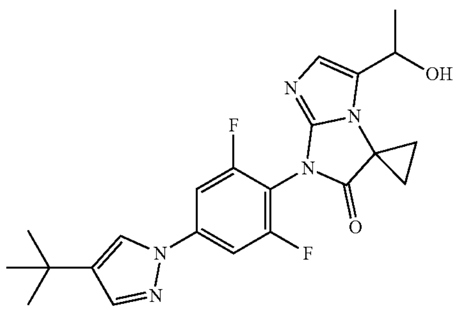 [SMILES: CC(O)c1cnc2n1C1(CC1)C(=O)N2c1c(F)cc(-n2cc(C(C)(C)C)cn2)cc1F] | 7'-[4-(4-tert-butylpyrazol-1-yl)-2,6-difluoro-phenyl]-3'-(1-hydroxyethyl)spiro[cyclopropane-1,5'-imidazo[1,2-a]imidazole]-6'-one | 0.842 |
| 59 | 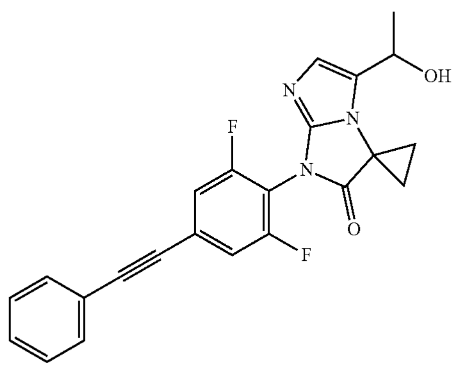 [SMILES: CC(O)c1cnc2n1C1(CC1)C(=O)N2c1c(F)cc(C#Cc2ccccc2)cc1F] | 7'-[2,6-difluoro-4-(2-phenylethynyl)phenyl]-3'-(1-hydroxyethyl)spiro[cyclopropane-1,5'-imidazo[1,2-a]imidazole]-6'-one | 0.824 |

The compounds of formula (I) and pharmaceutically acceptable salts thereof can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. However, the administration can also be effected rectally, e.g. in the form of suppositories, or parenterally, e.g. in the form of injection solutions.

The compounds of formula (I) and pharmaceutically acceptable salts thereof can be processed with pharmaceutically inert, inorganic or organic carriers for the production of pharmaceutical preparations. Lactose, corn starch or derivatives thereof, talc, stearic acid or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like; depending on the nature of the active substance no carriers are, however, usually required in the case of soft gelatin capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula (I), but as a rule are not necessary. Suitable carriers for suppositories are, for example, natural or hardened oils, waxes, fats, semi-liquid or liquid polyols and the like.

In addition, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

As mentioned earlier, medicaments containing a compound of formula (I) or pharmaceutically acceptable salts thereof and a therapeutically inert excipient are also an object of the present invention, as is a process for the production of such medicaments which comprises bringing one or more compounds of formula I or pharmaceutically acceptable salts thereof and, if desired, one or more other therapeutically valuable substances into a galenical dosage form together with one or more therapeutically inert carriers.

As further mentioned earlier, the use of the compounds of formula (I) for the preparation of medicaments useful in the prevention and/or the treatment of the above recited diseases is also an object of the present invention.

The dosage can vary within wide limits and will, of course, be fitted to the individual requirements in each particular case. In general, the effective dosage for oral or parenteral administration is between 0.01-20 mg/kg/day, with a dosage of 0.1-10 mg/kg/day being preferred for all of the indications described. The daily dosage for an adult human being weighing 70 kg accordingly lies between 0.7-1400 mg per day, preferably between 7 and 700 mg per day.

Preparation of Pharmaceutical Compositions Comprising Compounds of the Invention Tablets of the following composition are manufactured in the usual manner:

| ingredient | mg/tablet | | | |
|---|---|---|---|---|
| | 5 | 25 | 100 | 500 |
| Compound of formula I | 5 | 25 | 100 | 500 |
| Lactose Anhydrous DTG | 125 | 105 | 30 | 150 |
| Sta-Rx 1500 | 6 | 6 | 6 | 60 |
| Microcrystalline Cellulose | 30 | 30 | 30 | 450 |
| Magnesium Stearate | 1 | 1 | 1 | 1 |
| Total | 167 | 167 | 167 | 831 |

Manufacturing Procedure
1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

Capsules of the following composition are manufactured:

| ingredient | mg/capsule | | | |
|---|---|---|---|---|
| | 5 | 25 | 100 | 500 |
| Compound of formula I | 5 | 25 | 100 | 500 |
| Hydrous Lactose | 159 | 123 | 148 | — |
| Corn Starch | 25 | 35 | 40 | 70 |
| Talk | 10 | 15 | 10 | 25 |
| Magnesium Stearate | 1 | 2 | 2 | 5 |
| Total | 200 | 200 | 300 | 600 |

Manufacturing Procedure
1. Mix ingredients 1, 2 and 3 in a suitable mixer for 30 minutes.
2. Add ingredients 4 and 5 and mix for 3 minutes.
3. Fill into a suitable capsule.

A compound of formula I lactose and corn starch are firstly mixed in a mixer and then in a comminuting machine. The mixture is returned to the mixer; the talc is added thereto and mixed thoroughly. The mixture is filled by machine into suitable capsules, e.g. hard gelatin capsules.

Injection solutions of the following composition are manufactured:

| ingredient | mg/injection solution. |
|---|---|
| Compound of formula I | 3 |
| Polyethylene Glycol 400 | 150 |
| acetic acid | q.s. ad pH 5.0 |
| water for injection solutions | ad 1.0 ml |

Manufacturing Procedure

A compound of formula I is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

EXPERIMENTAL SECTION

Experimental Part

Abbreviations

NIS N-iodosuccinimide
PPTS pyridinium p-toluenesulfonate
DCE 1,2-dichloroethane
DCM dichloromethane
TFA trifluoroacetic acid
THF tetrahydrofuran
NMP N-Methyl-2-pyrrolidone
DME 1,2-dimethoxyethane
dba dibenzylideneacetone
TLC thin layer chromatography
DMSO dimethylsulfoxide
TMEDA tetramethylethylenediamine Description of Examples and Preparation of Required Intermediates Example A.1

Preparation of 1-(4-Bromo-2-chloro-6-fluoro-phenyl)-3,3-dimethyl-1H-imidazo[1,2-a]imidazol-2-one

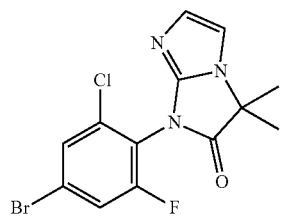 [SMILES: CC1(C)C(=O)N(c2c(F)cc(Br)cc2Cl)c2nccn21]

a) Step 1:
5-bromo-1-chloro-3-fluoro-2-isothiocyanato-benzene

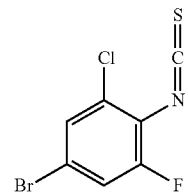 [SMILES: Fc1cc(Br)cc(Cl)c1N=C=S]

To a solution of 4-bromo-2-chloro-6-fluoro-phenylamine (1 g, 4.46 mmol) in THF (20 ml) at 0° C. were added drop wise saturated aqueous NaHCO$_3$ solution (5 ml) and thiophosgene (0.407 ml, 5.35 mmol) and the reaction mixture was stirred at 25° C. for 16 h. Reaction mixture was extracted with ethyl acetate. The organic layer was washed with brine solution, dried over Na₂SO₄ and evaporated under reduced pressure. The crude product was purified by column chromatography over silica gel (2-3% EtOAc in hexane) to get 5-bromo-1-chloro-3-fluoro-2-isothiocyanato-benzene (620 mg, 52%) as a colorless liquid.

b) Step 2: 3-(4-bromo-2-chloro-6-fluoro-phenyl)-5,5-dimethyl-2-thioxo-imidazolidin-4-one

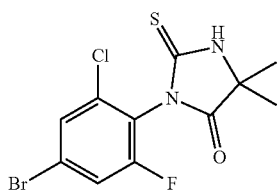 [SMILES: CC1(C)NC(=S)N(c2c(F)cc(Br)cc2Cl)C1=O]

To a solution of 2-amino-2-methyl-propionic acid methyl ester hydrochloride (600 mg, 3.92 mmol) and 5-bromo-1-chloro-3-fluoro-2-isothiocyanato-benzene (1064 mg, 4 mmol) in dioxane (20 ml) at 25° C. was added Et₃N (0.825 ml, 5.88 mmol) and the reaction mixture was stirred at 90° C. for 16 h. Solvent was evaporated under reduced pressure and the crude product was purified by flash chromatography (30-40% EtOAc in hexane) to get 3-(4-bromo-2-chloro-6-fluoro-phenyl)-5,5-dimethyl-2-thioxo-imidazolidin-4-one (1 g, 73%) as a light brown solid.

d) Step 3: 3-(4-Bromo-2-chloro-6-fluoro-phenyl)-2-[-2,2-dimethoxy-ethylimino]-5,5-dimethyl-imidazolidin-4-one

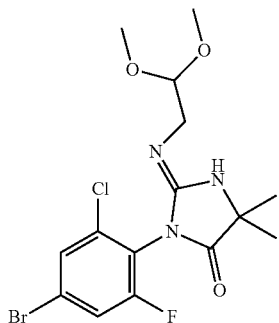 [SMILES: COC(C/N=C1\NC(C)(C)C(=O)N1c1c(F)cc(Br)cc1Cl)OC]

To a solution of 3-(4-bromo-2-chloro-6-fluoro-phenyl)-5,5-dimethyl-2-thioxo-imidazolidin-4-one (1 g, 2.85 mmol) in MeOH (30 ml) at 25° C. was added 2,2-dimethoxy-ethyl-amine (1.87 ml, 17.1 mmol). The reaction mixture was cooled to 0° C. and tBuOOH (70% solution in H₂O) (2.5 ml, 17.1 mmol) was added dropwise. The reaction mixture was stirred at 25° C. for 16 h. Reaction mixture was quenched with saturated aqueous NaHSO₃ solution and MeOH was evaporated. The resulting residue was extracted with EtOAc. The organic layer was washed with brine, dried over Na₂SO₄ and concentrated under reduced pressure. The crude product was purified by flash chromatrography (40-70% EtOAc/hexane) to get 3-(4-bromo-2-chloro-6-fluoro-1-phenyl)-2-[-2,2-dimethoxy ethylimino]-5,5-dimethyl-imidazolidin-4-one along with some impurities (450 mg, 37%) as yellow sticky solid. M+H+=421.8.

d) Step 4: 1-(4-Bromo-2-chloro-6-fluoro-phenyl)-3,3-dimethyl-1H-imidazo[1,2-a]imidazol-2-one To a solution of 3-(4-bromo-2-chloro-6-fluoro-phenyl)-2-[-2,2-dimethoxy-ethylimino]-5,5-dimethylimidazolidin-4-one (450 mg, 1.07 mmol) in DCE (10 ml) at 0° C. was added TFA (0.493 ml, 6.40 mmol) and the reaction mixture was stirred at 90° C. for 1 h. Solvent was evaporated under reduced pressure; resulting crude was diluted with CH₂Cl₂ (30 ml) and washed with sat. aqueous NaHCO₃ solution and brine. The organic layer was dried over Na₂SO₄ and evaporated under reduced pressure. The resulting residue was purified by flash chromatography (20-50% EtOAc/hexane) to get 1-(4-bromo-2-chloro-6-fluoro-phenyl)-3,3-dimethyl-1H imidazo[1,2-a]imidazol-2-one (275 mg, 72%) as off white solid. M+H+=358.1.

In analogy to Example A.1, Examples A.2 to A.4 of the following table were prepared from the commercially available anilines:

| Example No. | Structure | Systematic Name | Starting materials | MW found (M + H) |
|---|---|---|---|---|
| A.2 | ![structure] | 1-(4-Bromo-2,6-difluoro-phenyl)-3,3-dimethyl-1H-imidazo[1,2-a]imidazol-2-one | 4-bromo-2,6-difluoro-phenylamine (commercial) | 342.1 |

| Example No. | Structure | Systematic Name | Starting materials | MW found (M + H) |
|---|---|---|---|---|
| A.3 | 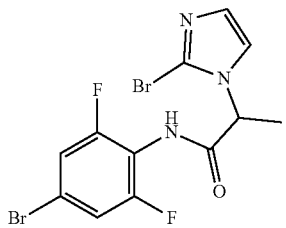 | 7'-(2,6-difluoro-4-iodo-phenyl)spiro[cyclopropane-1,5'-imidazo[1,2-a]imidazole]-6'-one | 4-iodo-2,6-difluoro-phenylamine (commercial) | 387.8 |
| A.4 | 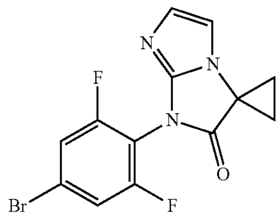 [SMILES: O=C1N(c2c(F)cc(Br)cc2F)c2nccn2C12CC2] | 7'-(2,6-difluoro-4-bromo-phenyl)spiro[cyclopropane-1,5'-imidazo[1,2-a]imidazole]-6'-one | 4-bromo-2,6-difluoro-phenylamine (commercial) | 342.0 |

Example A.5

Preparation of 1-(4-Bromo-2,6-difluoro-phenyl)-3-methyl-1H-imidazo[1,2-a]imidazol-2-one

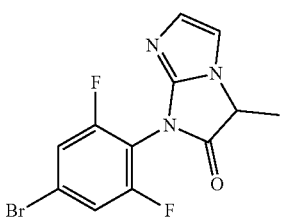 [SMILES: CC1C(=O)N(c2c(F)cc(Br)cc2F)c2nccn21]

a) Step 1: 2-bromo-N-(4-bromo-2,6-difluoro-phenyl)-propionamide

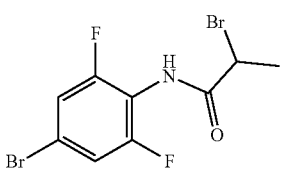

To a solution of 4-bromo-2,6-difluoro-phenylamine (4 g, 19.2 mmol) in DMF (40 ml) at 0° C. were added Et₃N (4.04 ml, 28.9 mmol) and 2-bromo-propionyl bromide (3.01 ml, 28.8 mmol) and reaction mixture was stirred at 25° C. for 16 h. The solvent was evaporated under reduced pressure and resulting crude was purified by flash chromatography (20-30% EtOAc in hexane) to get 2-bromo-N-(4-bromo-2,6-difluoro-phenyl)-propionamide (2.8 g, 42%) as an off-white solid. M+H+=343.8.

b) Step 2: N-(4-bromo-2,6-difluoro-phenyl)-2-(2-bromo-imidazol-1-yl)-propionamide To a suspension of NaH (60% in oil) (209 mg, 5.25 mmol) in THF (10 ml) at 0° C. was added drop wise a solution of 2-bromo-imidazole (447 mg, 3.06 mmol) in THF (10 ml) and the reaction mixture was stirred at 25° C. for 30 min. The reaction mixture was cooled to 0° C. and a solution of 2-bromo-N-(4-bromo-2,6-difluoro-phenyl)-propionamide (1.5 g, 4.37 mmol) in THF (10 ml) was added. The reaction mixture was stirred at 60° C. for 16 h. Reaction mixture was quenched with water and extracted with EtOAc. Organic layer was washed with brine, dried over Na₂SO₄ and evaporated under reduced pressure. Resulting crude was purified by flash chromatography (40-50% EtOAc in hexane) to get N-(4-bromo-2,6-difluoro-phenyl)-2-(2-bromoimidazol-1-yl)-propionamide (260 mg, 15%) as an off-white solid. M+H+=409.9.

c) Step 3: 1-(4-Bromo-2,6-difluoro-phenyl)-3-methyl-1H-imidazo[1,2-a]imidazol-2-one To a solution of N-(4-bromo-2,6-difluoro-phenyl)-2-(2-bromo-imidazol-1-yl)-propionamide (260 mg, 0.636 mmol) in NMP (2 ml) at 25° C. was added Ag₂CO₃ (174.82 mg, 0.636 mmol) and the reaction mixture was stirred at 150° C. for 1 h. Reaction mixture was cooled to 25° C., diluted with EtOAc, filtered through celite and filtrate was washed with water and brine solution. Organic layer was dried over Na₂SO₄ and evaporated under reduced pressure. Resulting crude was purified by flash chromatography (20-30% EtOAc in hexane) to get 1-(4-bromo-2,6-difluoro-phenyl)-3-methyl-1H-imidazo[1,2-a]imidazol-2-one (65 mg, 35%) as off white solid. M+H+=327.8.

The enantiomers of 1-(4-bromo-2,6-difluoro-phenyl)-3-methyl-1H-imidazo[1,2-a]imidazol-2-one (Example A.5) were separated by chiral HPLC and the two enantiomers were arbitrarily assigned as "enantiomer 1" and "enantiomer 2".

Example 1

Preparation of 3-[2,6-Difluoro-4-(2-phenylethynyl)phenyl]-2,3-dihydrospiro[[1,3]diazolo[1,2-a]imidazole-1,1'-cyclopropane]-2-one

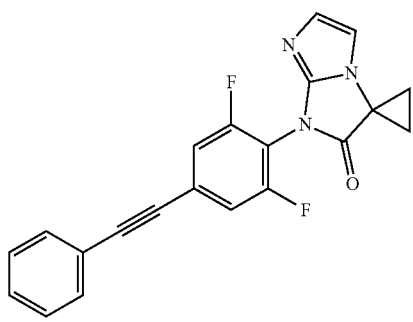 [SMILES: O=C1N(c2c(F)cc(C#Cc3ccccc3)cc2F)c2nccn2C12CC2]

To a solution of 3-(4-bromo-2,6-difluorophenyl)-2,3-dihydrospiro[[1,3]diazolo[1,2-a]imidazole-1,1'-cyclopropane]-2-one (Example A.4) (350 mg, 1.03 mmol) in THF (20 ml) were added phenyl acetylene (0.22 ml, 2.06 mmol) and Et$_3$N (0.722 ml, 5.15 mmol) and reaction mixture was purged with nitrogen for 10 min. Then PdCl$_2$(PPh$_3$)$_2$ (43.3 mg, 0.062 mmol) and CuI (5.88 mg, 0.031 mmol) were added and the reaction mixture was again purged with nitrogen for 10 min. The reaction mixture was stirred at 70° C. for 2 h. The reaction mixture was cooled to 25° C. and concentrated under reduced pressure. The resulting crude was purified by flash chromatography (30-50% EtOAc in hexane) to get 3-[2,6-difluoro-4-(2-phenylethynyl)phenyl]-2,3-dihydrospiro[[1,3]diazolo[1,2-a]-imidazole-1,1'-cyclopropane]-2-one (320 mg, 86%) as light brown solid. M+H+=361.6.

In analogy to Example 1, Examples 2-5, and intermediates B.1 of the following table were prepared from the bromo- or iodo-intermediates A.1-A.5 and the commercially available acetylenes using a Sonogashira cross-coupling:

| Example No. | Structure | Systematic Name | Starting materials | MW found (M + H) |
|---|---|---|---|---|
| 2 | 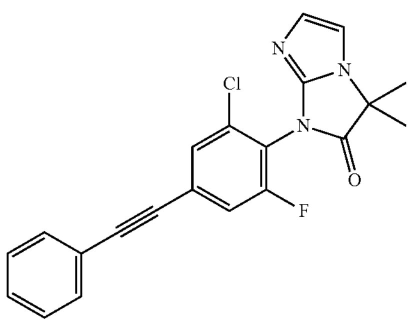 [SMILES: CC1(C)C(=O)N(c2c(F)cc(C#Cc3ccccc3)cc2Cl)c2nccn21] | 1-(2-chloro-6-fluoro-4-(phenylethynyl)phenyl)-3,3-dimethyl-1H-imidazo[1,2-a]imidazol-2(3H)-one | 1-(4-Bromo-2-chloro-6-fluoro-phenyl)-3,3-dimethyl-1H-imidazo[1,2-a]imidazol-2-one (Example A.1) and phenylacetylene (commercial) | 380.2 |
| 3 | enantiomer 1 | 1-(2,6-difluoro-4-(phenylethynyl)phenyl)-3-methyl-1H-imidazo[1,2-a]imidazol-2(3H)-one (enantiomer 1) | 1-(4-Bromo-2,6-difluoro-phenyl)-3-methyl-1H-imidazo[1,2-a]imidazol-2-one (Example A.5, enantiomer 1) and phenylacetylene (commercial) | 350.2 |

-continued

| Example No. | Structure | Systematic Name | Starting materials | MW found (M + H) |
|---|---|---|---|---|
| 4 | 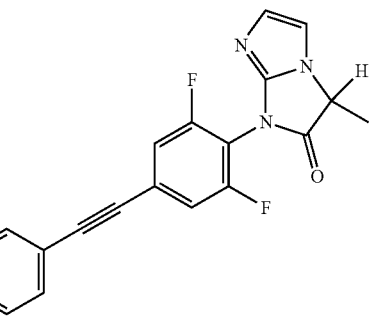 enantiomer 2 | 1-(2,6-difluoro-4-(phenylethynyl)phenyl)-3-methyl-1H-imidazo[1,2-a]imidazol-2(3H)-one (enantiomer 2) | 1-(4-Bromo-2,6-difluorophenyl)-3-methyl-1H-imidazo[1,2-a]imidazol-2-one (Example A.5, enantiomer 2) and phenylacetylene (commercial) | 350.2 |
| 5 | 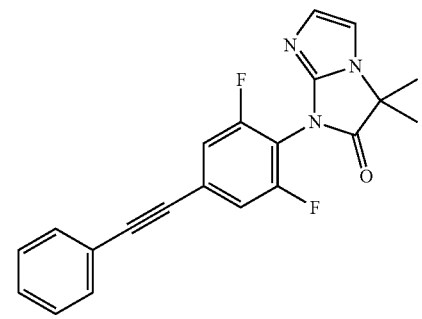 [SMILES: CC1(C)C(=O)N(c2c(F)cc(C#Cc3ccccc3)cc2F)c2nccn21] | 1-(2,6-difluoro-4-(phenylethynyl)phenyl)-3,3-dimethyl-1H-imidazo[1,2-a]imidazol-2(3H)-one | 1-(4-Bromo-2,6-difluorophenyl)-3,3-dimethyl-1H-imidazo[1,2-a]imidazol-2-one (Example A.2) and phenylacetylene (commercial) | 364.2 |
| B.1 | 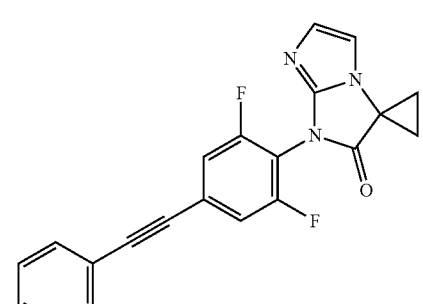 | 7'-[2,6-difluoro-4-[2-(3-pyridyl)ethynyl]phenyl]spiro[cyclopropane-1,5'-imidazo[1,2-a]imidazole]-6'-one | 3-(4-bromo-2,6-difluorophenyl)-2,3-dihydrospiro[[1,3]diazolo[1,2-a]imidazole-1,1'-cyclopropane]-2-one (Example A.4) and 3-ethynylpyridine (commercial) | 363.2 |

Example 6

Preparation of 1'-(4'-(1,1-difluoroethyl)-3,5-difluoro-[1,1'-biphenyl]-4-yl)spiro[cyclopropane-1,3'-imidazo[1,2-a]imidazol]-2'(1'H)-one

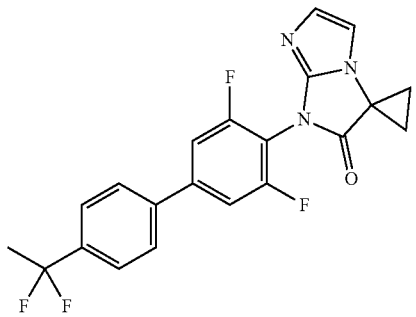 [SMILES: CC(F)(F)c1ccc(-c2cc(F)c(N3C(=O)C4(CC4)n4ccnc43)c(F)c2)cc1]

To a solution of 1'-(4-bromo-2,6-difluorophenyl)spiro[cyclopropane-1,3'-imidazo[1,2-a]imidazol]-2'(1'H)-one (Example A.4) (20 mg, 58.8 µmol, 1 eq.) in DME (200 µl) and water (50 µl) was added 2-(4-(1,1-difluoroethyl)phenyl)-4,4,5,5-tetramethyl-1,3,2-dioxaborolane (23.6 mg, 88.2 µmol, 1.5 eq.), triphenylphosphine (6.17 mg, 23.5 µmol, 0.4 eq.), Na$_2$CO$_3$ (31.2 mg, 294 µmol, 5 eq.) and Pd(OAc)$_2$ (2.64 mg, 11.8 µmol, 0.2 eq.) under argon at room temperature. The mixture was stirred for 1 hr at 70° C. The reaction mixture was diluted with saturated aqueous NaHCO$_3$-solution and extracted twice with EtOAc. The combined organic layers were washed with brine, dried over Na$_2$SO$_4$ and concentrated in vacuo. The crude material was purified by flash chromatography on silica gel (0% to 100% EtOAc in heptane). The desired 1'-(4'-(1,1-difluoroethyl)-3,5-difluoro-[1,1'-biphenyl]-4-yl)spiro[cyclopropane-1,3'-imidazo[1,2-a]imidazol]-2'(1'H)-one (17 mg, 38.1 µmol, 64.8% yield) was obtained as a off-white semi-solid. M+H+=402.2.

Example 7

Preparation of N-[3,5-difluoro-4-(6'-oxospiro[cyclopropane-1,5'-imidazo[1,2-a]imidazole]-7'-yl)phenyl]pyridine-2-carboxamide

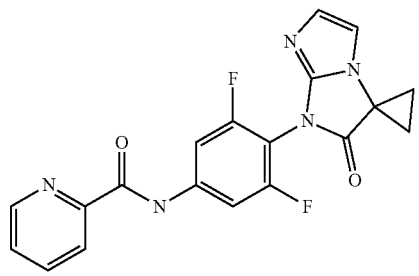

To a solution of 7'-(2,6-difluoro-4-iodo-phenyl)spiro[cyclopropane-1,5'-imidazo[1,2-a]imidazole]-6'-one (Example A.3) (500 mg, 1.29 mmol, 1 eq.) and picolinamide (237 mg, 1.94 mmol, 1.5 eq.) in toluene (15 ml) were added phosphoric acid potassium salt (548 mg, 2.58 mmol, 2 eq.), CuI (37 mg, 0.19 mmol, 0.15 eq.) and trans-1,2 diaminocyclohexane (29.5 mg, 0.260 mmol, 0.2 eq.) and reaction mixture was heated at 100° C. under argon for 20 h. The reaction mixture was diluted with EtOAc and washed with water. The organics were dried over Na$_2$SO$_4$ and concentrated in vacuo. The crude material was purified by flash chromatography on silica gel (40-60% EtOAc/hexane) to yield N-[3,5-difluoro-4-(6'-oxospiro[cyclopropane-1,5'-imidazo[1,2-a]imidazole]-7'-yl)phenyl]pyridine-2-carboxamide (220 mg, 0.580 mmol, 43.3% yield) as yellow solid. M+H+=381.8.

Example B.2

Preparation of 7'-[4-[4-(difluoromethoxy)phenyl]-2,6-difluoro-phenyl]spiro[cyclopropane-1,5'-imidazo[1,2-a]imidazole]-6'-one

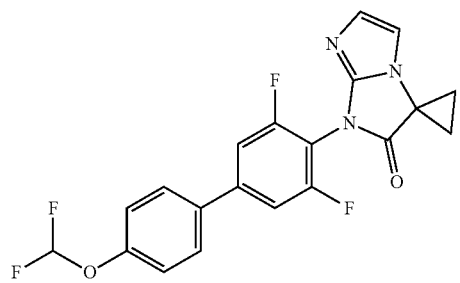 [SMILES: O=C1N(c2c(F)cc(-c3ccc(OC(F)F)cc3)cc2F)c2nccn2C12CC2]

To a solution of compound 1'-(4-bromo-2,6-difluorophenyl)spiro[cyclopropane-1,3'-imidazo[1,2-a]imidazol]-2'(1'H)-one (Example A.4) (150 mg, 0.440 mmol, 1 eq.) and 4-(difluoromethoxy)phenylboronic acid (165 mg, 0.880 mmol, 2 eq.) in DMF (10 ml) and H$_2$O (0.1 ml) was added Na$_2$CO$_3$ (93.5 mg, 0.880 mmol, 2 eq.) at 25° C. and the reaction mixture purged with argon for 10 min. Then Pd(PPh$_3$)$_4$ (51 mg, 0.040 mmol, 0.1 eq.) was added and the reaction mixture again purged with argon for 10 min. The reaction mixture was stirred at 80° C. for 2 h. The reaction was was diluted with EtOAc (100 ml) and the organic layer was washed with water (2×20 ml) water and brine (20 ml), dried over Na$_2$SO$_4$ and concentrated in vacuo. The crude product was then purified by flash chromatography (5% EtOAc in hexane) to give 7'-[4-[4-(difluoromethoxy)phenyl]-2,6-difluoro-phenyl]spiro[cyclopropane-1,5'-imidazo[1,2-a]imidazole]-6'-one (200 mg, 0.500 mmol, 86.58% yield) as a yellow solid. M+H+=404.0 Example B.3

Preparation of 7'-[4-(4-tert-butylpyrazol-1-yl)-2,6-difluoro-phenyl]spiro[cyclopropane-1,5'-imidazo[1,2-a]imidazole]-6'-one

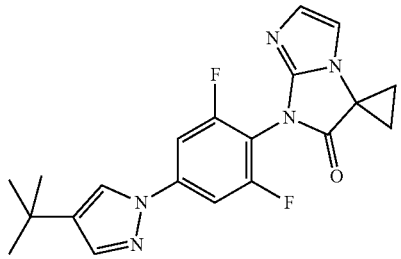 [SMILES: CC(C)(C)c1cnn(-c2cc(F)c(N3C(=O)C4(CC4)n4ccnc43)c(F)c2)c1]

To a solution of 7'-(2,6-difluoro-4-iodo-phenyl)spiro[cyclopropane-1,5'-imidazo[1,2-a]imidazole]-6'-one (Example A.3) (300 mg, 0.770 mmol, 1 eq.) and 4-tert-butyl-1H-pyrazole (192 mg, 1.55 mmol, 2 eq.) in toluene (40 ml) were added $K_3PO_4$ (494 mg, 2.32 mmol, 3 eq) and N,N'-Dimethyl-1,2-cyclohexanediamine (23 mg, 0.160 mmol, 0.21 eq.) and the reaction mixture was purged with nitrogen for 10 min. CuI (15 mg, 0.08 mmol, 0.1 eq.) was added and the reaction mixture was heated at 110° C. for 16 h. The reaction mixture was diluted with water and extracted with EtOAc. The organic layer was dried over $Na_2SO_4$, concentrated in vacuo and purified by flash chromatography over silica gel (50-70% EtOAc in hexane) to yield 7'-[4-(4-tert-butylpyrazol-1-yl)-2,6-difluoro-phenyl]spiro[cyclopropane-1,5'-imidazo[1,2-a]imidazole]-6'-one (200 mg, 0.520 mmol, 61.3% yield) as yellow solid. M+H+=384.0.

Example B.4

Preparation of 3,5-difluoro-4-(6'-oxospiro[cyclopropane-1,5'-imidazo[1,2-a]imidazole]-7'-yl)-N-(2-pyridyl)benzamide

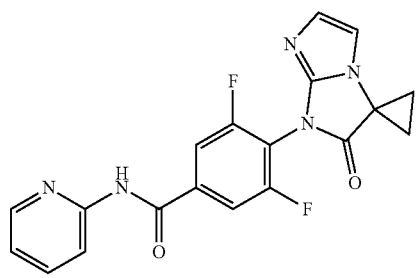 [SMILES: O=C(Nc1ccccn1)c1cc(F)c(N2C(=O)C3(CC3)n3ccnc32)c(F)c1]

A solution of compound 7'-(2,6-difluoro-4-iodo-phenyl) spiro[cyclopropane-1,5'-imidazo[1,2-a]imidazole]-6'-one (Example A.3) (250 mg, 0.650 mmol, 1 eq.), 2-aminopyridine (122 mg, 1.29 mmol, 2 eq.) and triethylamine (0.27 ml, 1.94 mmol, 3 eq.) in DMF (5 ml) was purged with argon for 10 min, then 1,1'-bis(diphenylphosphino)ferrocene-palladium(II)dichloride dichloromethane complex (52.7 mg, 0.060 mmol, 0.1 eq) was added at 25° C. The reaction mixture was purged with argon for 10 min, then was stirred at 80° C. under CO gas (1 atm) for 2 h. The reaction mixture was cooled to room temperature and the solvent was evaporated to dryness. The residue was taken up in EtOAc (250 ml) washed with water (2×100 ml) and brine (100 ml), dried over $Na_2SO_4$, concentrated in vacuo and purified by flash chromatography over silica gel (30-60% EtOAc in hexane) to yield 3,5-difluoro-4-(6'-oxospiro[cyclopropane1,5'-imidazo[1,2-a]imidazole]-7'-yl)-N-(2-pyridyl)benzamide (150 mg, 0.390 mmol, 91.4% yield) as light brown solid. M+H+=381.7.

Example B.5

Preparation of 7'-[2,6-difluoro-4-[4-(2,2,2-trifluoroethyl)piperazin-1-yl]phenyl]spiro[cyclopropane-1,5'-imidazo[1,2-a]imidazole]-6'-one

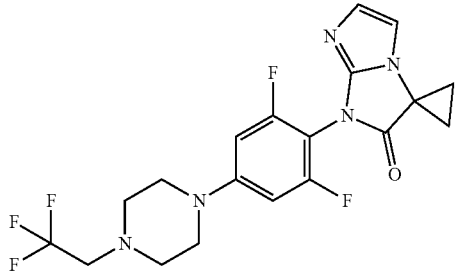 [SMILES: O=C1N(c2c(F)cc(N3CCN(CC(F)(F)F)CC3)cc2F)c2nccn2C12CC2]

To a solution of 7'-(4-bromo-2,6-difluoro-phenyl)spiro [cyclopropane-1,5'-imidazo[1,2-a]imidazole]-6'-one (Example A.4) (150 mg, 0.440 mmol, 1 eq.) in toluene (20 ml) were added 1-(2,2,2-trifluoroethyl)piperazine (111 mg, 0.660 mmol, 1.5 eq.), (±)-2,2'-bis(diphenylphosphino)-1, 1'binaphthyl (27.5 mg, 0.040 mmol, 0.1 eq.) and $Cs_2CO_3$ (431 mg, 1.32 mmol, 3 eq.) and the reaction mixture was purged with nitrogen for 10 min. $Pd_2dba_3$ (16.6 mg, 0.020 mmol, 0.04 eq.) was added and the reaction mixture was again degassed for 10 min. The reaction mixture stirred for 16 h at 110° C., cooled to 25° C., and diluted with EtOAc (150 ml). The organics were washed with water (2×50 ml) and brine (50 ml), dried over $Na_2SO_4$ and concentrated in vacuo. The crude product was purified by flash chromatography (40% EtOAc in hexane), the desired fractions concentrated to dryness in vacuo, and the residue triturated with pentane to afford 7'-[2,6-difluoro-4-[4-(2,2,2-trifluoroethyl) piperazin-1-yl]phenyl]spiro[cyclopropane-1,5'-imidazo[1,2-a]imidazole]-6'-one (170 mg, 0.400 mmol, 81.2% yield) as yellow solid. M+H+=427.9.

Example B.6

Preparation of 7'-[2,6-difluoro-4-[4-(trifluoromethyl)pyrazol-1-yl]phenyl]spiro[cyclopropane-1,5'-imidazo[1,2-a]imidazole]-6'-one

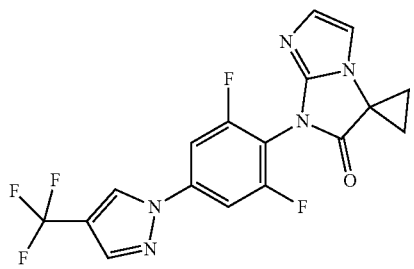 [SMILES: O=C1N(c2c(F)cc(-n3cc(C(F)(F)F)cn3)cc2F)c2nccn2C12CC2]

To a solution of 7'-(2,6-difluoro-4-iodo-phenyl)spiro[cyclopropane-1,5'-imidazo[1,2-a]imidazole]-6'-one (Example A.3) (300 mg, 0.770 mmol, 1 eq.) and 4-(trifluoromethyl)-1H-pyrazole (158 mg, 1.16 mmol, 1.5 eq.) in toluene (1.5 mL) was added K$_3$PO$_4$ (494 mg, 2.32 mmol, 3 eq.) and 1,2-N,N'dimethyl-1,2-cyclohexanediamine (23 mg, 0.160 mmol, 0.21 eq.) and degassed with nitrogen for 10 min. CuI (15 mg, 0.080 mmol, 0.1 eq.) was added, the reaction mixture again degassed with nitrogen for 10 mins, and stirred at 130° C. in the microwave for 1 h. The reaction mixture was diluted with EtOAc (50 ml), the organics washed with water (2×20 mL) and brine (20 mL), dried over Na$_2$SO$_4$, concentrated in vacuo and purified by flash chromatography over silica gel (50% EtOAc in hexane) to yield 7'-[2,6-difluoro-4-[4-(trifluoromethyl)pyrazol-1-yl]phenyl]spiro[cyclopropane-1,5'-imidazo[1,2-a]imidazole]-6'-one (40 mg, 0.1 mmol, 13% yield) as a sticky gel. M+H+=396.0.

Example 8

Preparation of 1-(2,6-difluoro-4-(phenylethynyl)phenyl)-5-iodo-3,3-dimethyl-1H-imidazo[1,2-a]imidazol-2(3H)-one

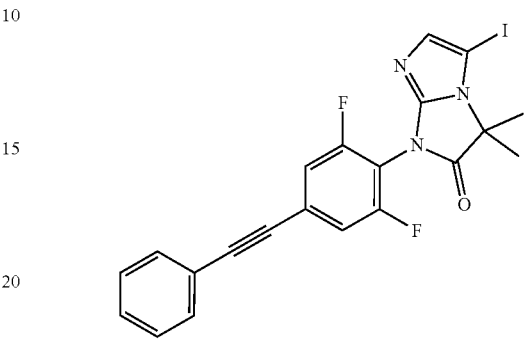

1-(2,6-difluoro-4-(phenylethynyl)phenyl)-3,3-dimethyl-1H-imidazo[1,2-a]imidazol-2(3H)-one (Example 5) (20 mg, 55 µmol, Eq: 1) was dissolved in CH$_2$Cl$_2$ (1 ml) and NIS (18.6 mg, 82.6 µmol, Eq: 1.5) and PPTS (1.38 mg, 5.5 µmol, Eq: 0.1) were added at 0° C. The mixture was stirred for 30 min at 0° C. The reaction mixture was diluted with sat. aq. NaHCO$_3$ solution and extracted twice with CH$_2$Cl$_2$. The organic layers were extracted with brine, dried over MgSO$_4$ and concentrated in vacuo. The crude material was purified by flash chromatography on silica gel (0% to 100% EtOAc in heptane). The desired 1-(2,6-difluoro-4-(phenylethynyl)phenyl)-5-iodo-3,3-dimethyl-1H-imidazo[1,2-a]imidazol-2(3H)-one (9 mg, 17.5 µmol, 31.7% yield) was obtained as a off-white solid. M+H+=490.1

In analogy to Example 8, Examples 9-10 and C1 to C.8 of the following table were prepared from the unfunctionalized intermediates and NIS:

| Example No. | Structure | Systematic Name | Starting materials | MW found (M + H) |
|---|---|---|---|---|
| 9 | 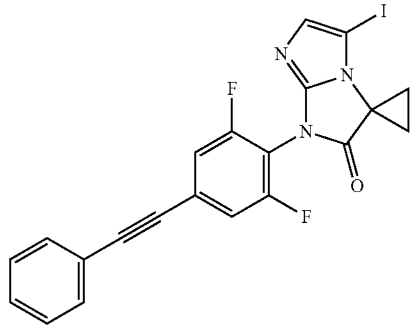 [SMILES: O=C1N(c2c(F)cc(C#Cc3ccccc3)cc2F)c2ncc(I)n2C12CC2] | 3-[2,6-difluoro-4-(2-phenylethynyl)phenyl]-6-iodo-2,3-dihydrospiro[[1,3]diazolo[1,2-a]imidazole-1,1'-cyclopropane]-2-one | 3-[2,6-difluoro-4-(2-phenylethynyl)phenyl]-2,3-dihydrospiro[[1,3]diazolo[1,2-a]imidazole-1,1'-cyclopropane]-2-one (Example 1) and NIS (1.5 eq.) | 487.9 |

| Example No. | Structure | Systematic Name | Starting materials | MW found (M + H) |
|---|---|---|---|---|
| 10 | 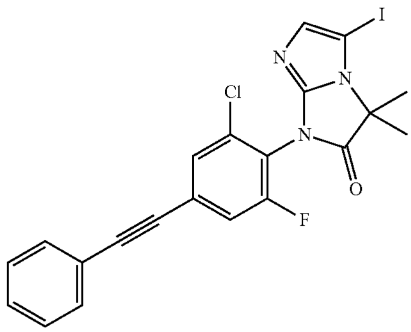 [SMILES: CC1(C)C(=O)N(c2c(F)cc(C#Cc3ccccc3)cc2Cl)c2ncc(I)n21] | 1-(2-chloro-6-fluoro-4-(phenylethynyl)phenyl)-5-iodo-3,3-dimethyl-1H-imidazo[1,2-a]imidazol-2(3H)-one | 1-(2-chloro-6-fluoro-4-(phenylethynyl)phenyl)-3,3-dimethyl-1H-imidazo[1,2-a]imidazol-2(3H)-one (Example 2) and NIS (1.5 eq.) | 506.1 |
| C.1 | 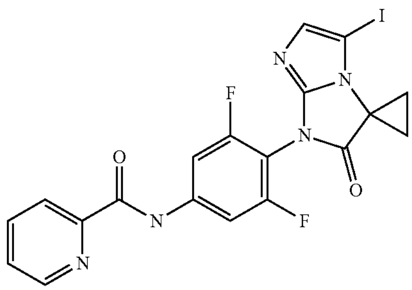 [SMILES: O=C(Nc1cc(F)c(N2C(=O)C3(CC3)n3c(I)cnc32)c(F)c1)c1ccccn1] | N-[3,5-difluoro4-(3'-iodo-6'-oxo-spiro[cyclopropane-1,5'-imidazo[1,2-a]imidazole]-7'-yl)phenyl]pyridine-2-carboxamide | N-[3,5-difluoro-4-(6'-oxospiro[cyclopropane-1,5'-imidazo[1,2-a]imidazole]-7'-yl)phenyl]pyridine-2-carboxamide (Example 7) and NIS (1.1 eq.) | 508.1 |
| C.2 | 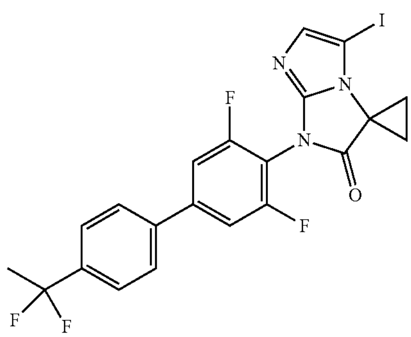 [SMILES: CC(F)(F)c1ccc(-c2cc(F)c(N3C(=O)C4(CC4)n4c(I)cnc43)c(F)c2)cc1] | 7'-[4-[4-(1,1-difluoroethyl)phenyl]-2,6-difluoro-phenyl]-3'-iodo-spiro[cyclopropane-1,5'-imidazo[1,2-a]imidazole]-6'-one | 7'-[4-[4-(1,1-difluoroethyl)phenyl]-2,6-difluoro-phenyl]spiro[cyclopropane-1,5'-imidazo[1,2-a]imidazole]-6'-one (Example 6) and NIS (1 eq.) | 527.9 |
| C.3 | 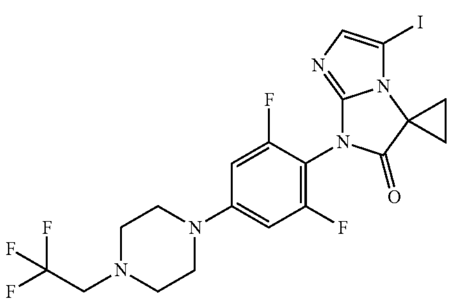 [SMILES: O=C1N(c2c(F)cc(N3CCN(CC(F)(F)F)CC3)cc2F)c2ncc(I)n2C12CC2] | 7'-[2,6-difluoro-4-[4-(2,2,2-trifluoroethyl)piperazin-1-yl]phenyl]-3'-iodo-spiro[cyclopropane-1,5'-imidazo[1,2-a]imidazole]-6'-one | 7'-[2,6-difluoro-4-[4-(2,2,2-trifluoroethyl)piperazin-1-yl]phenyl]spiro[cyclopropane-1,5'-imidazo[1,2-a]imidazole]-6'-one (Example B.5) and NIS (1 eq.) | 553.8 |
| C.4 | 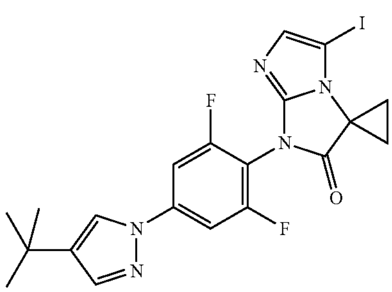 [SMILES: CC(C)(C)c1cnn(-c2cc(F)c(N3C(=O)C4(CC4)n4c(I)cnc43)c(F)c2)c1] | 7'-[4-(4-tert-butylpyrazol-1-yl)-2,6-difluoro-phenyl]-3'-iodo-spiro[cyclopropane-1,5'-imidazo[1,2-a]imidazole]-6'-one | 7'-[4-(4-tert-butylpyrazol-1-yl)-2,6-difluoro-phenyl]spiro[cyclopropane-1,5'-imidazo[1,2-a]imidazole]-6'-one (Example B.3) and NIS (1 eq.) | 510.0 |

-continued

| Example No. | Structure | Systematic Name | Starting materials | MW found (M + H) |
|---|---|---|---|---|
| C.5 | 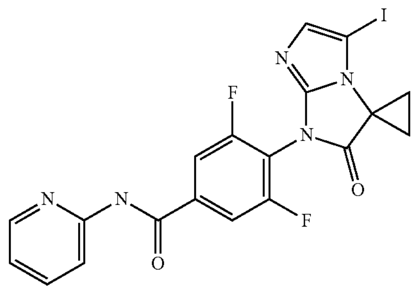 [SMILES: O=C(Nc1ccccn1)c1cc(F)c(N2C(=O)C3(CC3)n3c(I)cnc32)c(F)c1] | 3,5-difluoro-4-(3'-iodo-6'-oxo-spiro[cyclopropane-1,5'-imidazo[1,2-a]imidazole]-7'-yl)-N-(2-pyridyl)benzamide | 3,5-difluoro-4-(6'-oxospiro[cyclopropane-1,5'-imidazo[1,2-a]imidazole]-7'-yl)-N-(2-pyridyl)benzamide (Example B.4) and NIS (1 eq.) | 508.0 |
| C.6 | 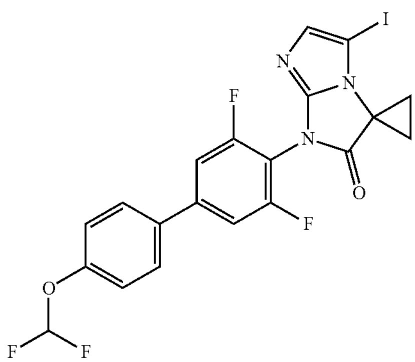 [SMILES: O=C1N(c2c(F)cc(-c3ccc(OC(F)F)cc3)cc2F)c2ncc(I)n2C12CC2] | 7'-[4-[4-(difluoromethoxy)phenyl]-2,6-difluoro-phenyl]-3'-iodo-spiro[cyclopropane-1,5'-imidazo[1,2-a]imidazole]-6'-one | 7'-[4-[4-(difluoromethoxy)phenyl]-2,6-difluoro-phenyl]spiro[cyclopropane-1,5'-imidazo[1,2-a]imidazole]-6'-one (Example B.2) and NIS (1 eq.) | 529.9 |
| C.7 | 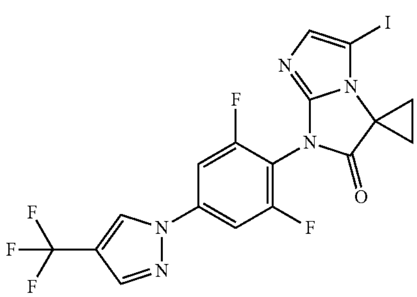 [SMILES: O=C1N(c2c(F)cc(-n3cc(C(F)(F)F)cn3)cc2F)c2ncc(I)n2C12CC2] | 7'-[2,6-difluoro-4-[4-(trifluoromethyl)pyrazol-1-yl]phenyl]-3'-iodo-spiro[cyclopropane-1,5'-imidazo[1,2-a]imidazole]-6'-one | 7'-[2,6-difluoro-4-[4-(trifluoromethyl)pyrazol-1-yl]phenyl]spiro[cyclopropane-1,5'-imidazo[1,2-a]imidazole]-6'-one (Example B.6) and NIS (1 eq.) | 522.3 |
| C.8 | 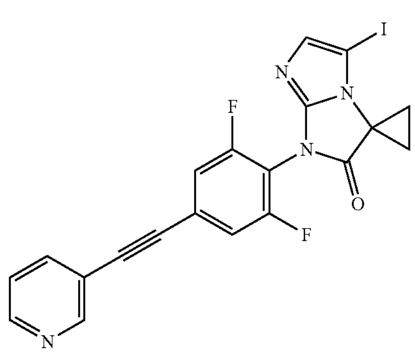 [SMILES: O=C1N(c2c(F)cc(C#Cc3cccnc3)cc2F)c2ncc(I)n2C12CC2] | 7'-[2,6-difluoro-4-[2-(3-pyridyl)ethynyl]phenyl]-3'-iodo-spiro[cyclopropane-1,5'-imidazo[1,2-a]imidazole]-6'-one | 7'-[2,6-difluoro-4-[2-(3-pyridyl)ethynyl]phenyl]spiro[cyclopropane-1,5'-imidazo[1,2-a]imidazole]-6'-one (Example B.1) and NIS (1.1 eq.) | 489.0 |

Example 11

Preparation of N-[3,5-difluoro-4-[6'-oxo-3'-(2-pyridyl)spiro[cyclopropane-1,5'-imidazo[1,2-a]imidazole]-7'-yl]phenyl]pyridine-2-carboxamide

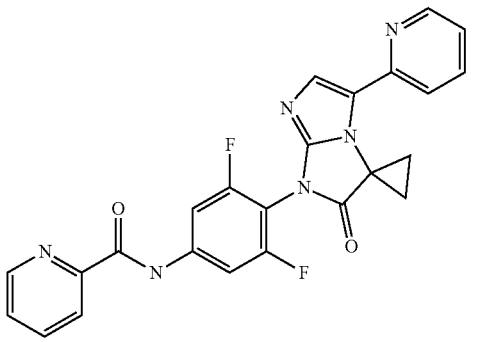

To a solution of N-[3,5-difluoro-4-(3'-iodo-6'-oxo-spiro[cyclopropane-1,5'-imidazo[1,2-a]imidazole]-7'-yl)phenyl]pyridine-2-carboxamide (Example C.1) (90 mg, 0.180 mmol, 1 eq.) in 1,4-dioxane (10 ml) was added 2-(tributylstannyl)pyridine (196 mg, 0.530 mmol, 3 eq.) and the reaction mixture was purged with nitrogen for 10 min. Then tetrakis(triphenylphosphine) palladium(0) (41 mg, 0.040 mmol, 0.20 eq), triethylamine (0.1 ml, 0.71 mmol, 4 eq.) and CuI (6.8 mg, 0.040 mmol, 0.2 eq) were added and the reaction was again degassed with nitrogen for 10 min. The reaction mixture stirred at 100° C. for 16 h, diluted with EtOAc and washed with water. The organic layer was dried over $Na_2SO_4$, concentrated in vacuo and the residue was purified by prep HPLC ($NH_4HCO_3/CH_3CN$) to yield N-[3,5-difluoro-4-[6'-oxo-3'-(2-pyridyl)spiro[cyclopropane-1,5'-imidazo[1,2-a]imidazole]-7'-yl]phenyl]pyridine-2-carboxamide (16.5 mg, 0.040 mmol, 20% yield) as an off-white solid. M+H+=459.0.

In analogy to Example 11, Examples 12-23, of the following table were prepared from the iodides 8-10 and C.1, C.4, C.5, C.7 and C.8 and the commercially available stannanes using a Stille cross-coupling.

| Example No. | Structure | Systematic Name | Starting materials | MW found (M + H) |
|---|---|---|---|---|
| 12 | 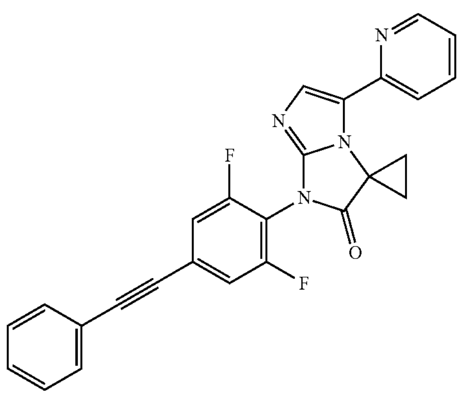 [SMILES: O=C1N(c2c(F)cc(C#Cc3ccccc3)cc2F)c2ncc(-c3ccccn3)n2C12CC2] | 3-[2,6-Difluoro-4-(2-phenylethynyl)phenyl]-6-(pyridin-2-yl)-2,3-dihydrospiro[[1,3]diazolo[1,2-a]imidazole-1,1'-cyclopropane]-2-one | 3-[2,6-difluoro-4-(2-phenylethynyl)phenyl]-6-iodo-2,3-dihydrospiro[[1,3]diazolo[1,2-a]imidazole-1,1'-cyclopropane]-2-one (Example 9) and 2-(tributylstannyl)pyridine (commercial) | 439.2 |
| 13 | 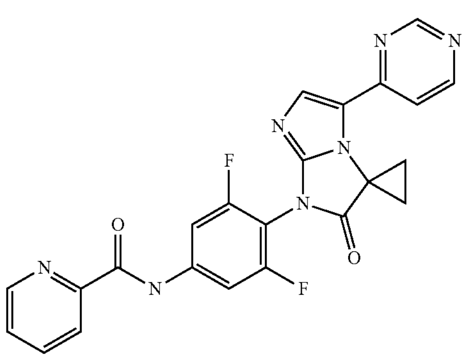 [SMILES: O=C(Nc1cc(F)c(N2C(=O)C3(CC3)n3c(-c4ccncn4)cnc32)c(F)c1)c1ccccn1] | N-[3,5-difluoro-4-(6'-oxo-3'-pyrimidin-4-yl-spiro[cyclopropane-1,5'-imidazo[1,2-a]imidazole]-7'-yl)phenyl]pyridine-2-carboxamide | N-[3,5-difluoro-4-(3'-iodo-6'-oxo-spiro[cyclopropane-1,5'-imidazo[1,2-a]imidazole]-7'-yl)phenyl]pyridine-2-carboxamide (Example C.1) and tributyl(pyrimidin-4-yl)stannane (commercial) | 460.2 |

-continued

| Example No. | Structure | Systematic Name | Starting materials | MW found (M + H) |
|---|---|---|---|---|
| 14 | 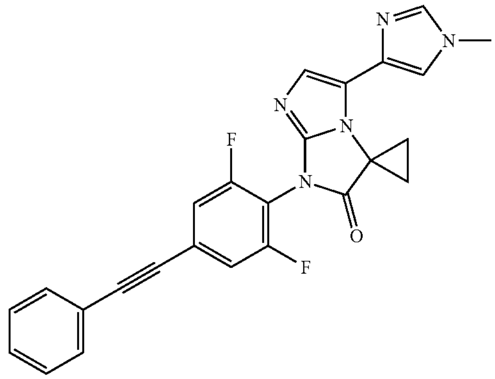 [SMILES: Cn1cnc(-c2cnc3n2C2(CC2)C(=O)N3c2c(F)cc(C#Cc3ccccc3)cc2F)c1] | 7'[2,6-difluoro-4-(2-phenylethynyl)phenyl]-3'-(1-methylimidazol-4-yl)spiro[cyclopropane-1,5'-imidazo[1,2-a]imidazole]-6'-one | 3-[2,6-difluoro-4-(2-phenylethynyl)phenyl]-6-iodo-2,3-dihydrospiro[[1,3]diazolo[1,2-a]imidazole-1,1'-cyclopropane]-2-one (Example 9) and tributyl-(1-methylimidazol-4-yl)stannane (commercial) | 442.1 |
| 15 | 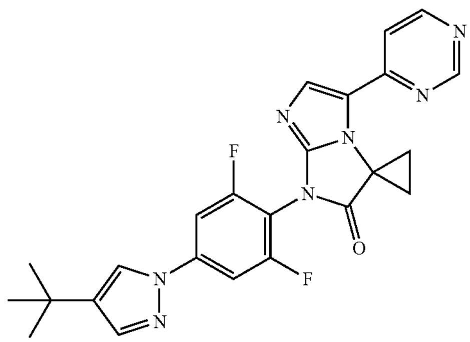 [SMILES: CC(C)(C)c1cnn(-c2cc(F)c(N3C(=O)C4(CC4)n4c(-c5ccncn5)cnc43)c(F)c2)c1] | 7'-[4-(4-tert-butylpyrazol-1-yl)-2,6-difluoro-phenyl]-3'-pyrimidin-4-yl-spiro[cyclopropane-1,5'-imidazo[1,2-a]imidazole]-6'-one | 7'-[4-(4-tert-butylpyrazol-1-yl)-2,6-difluoro-phenyl]-3'-iodo-spiro[cyclopropane-1,5'-imidazo[1,2-a]imidazole]-6'-one (Example C.4) and tributyl(pyrimidin-4-yl)stannane (commercial) | 462.3 |
| 16 | 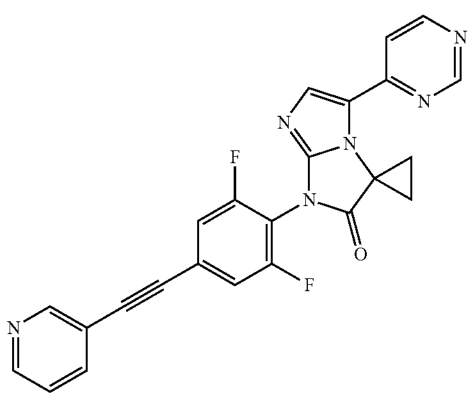 [SMILES: O=C1N(c2c(F)cc(C#Cc3cccnc3)cc2F)c2ncc(-c3ccncn3)n2C12CC2] | 7'-[2,6-difluoro-4-[2-(3-pyridypethynyl]phenyl]-3'-pyrimidin-4-yl-spiro[cyclopropane-1,5'-imidazo[1,2-a]imidazole]-6'-one | 7'-[2,6-difluoro-4-[2-(3-pyridyl)ethynyl]phenyl]-3'-iodo-spiro[cyclopropane-1,5'-imidazo[1,2-a]imidazole]-6'-one (Example C.8) and tributyl(pyrimidin-4-yl)stannane (commercial) | 441.0 |
| 17 | 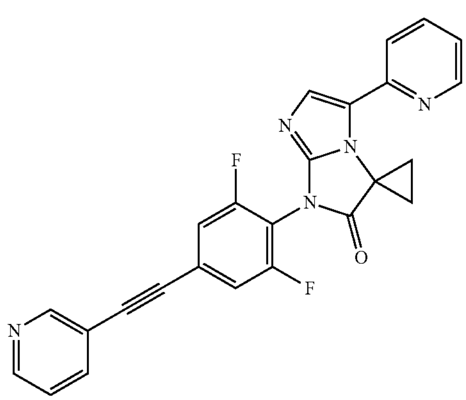 [SMILES: O=C1N(c2c(F)cc(C#Cc3cccnc3)cc2F)c2ncc(-c3ccccn3)n2C12CC2] | 7'-[2,6-difluoro-4-[2-(3-pyridypethynyl]phenyl]-3'-(2-pyridyl)spiro[cyclopropane-1,5'-imidazo[1,2-a]imidazole]-6'-one | 7'-[2,6-difluoro-4-[2-(3-pyridyl)ethynyl]phenyl]-3'-iodo-spiro[cyclopropane-1,5'-imidazo[1,2-a]imidazole]-6'-one (Example C.8) and 2-(tributylstannyl)pyridine (commercial) | 440.1 |

-continued

| Example No. | Structure | Systematic Name | Starting materials | MW found (M + H) |
|---|---|---|---|---|
| 18 | 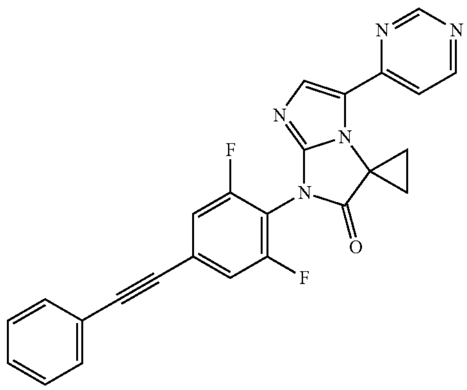 [SMILES: O=C1N(c2c(F)cc(C#Cc3ccccc3)cc2F)c2ncc(-c3ccncn3)n2C12CC2] | 3'[2,6-Difluoro-4-(2-phenylethynyl)phenyl]-6'-(pyrimidin-4-yl)-2',3'-dihydrospiro[cyclopropane-1,1'-imidazo-[1,2-a][1,3]diazole]-2'-one | 3-[2,6-difluoro-4-(2-phenylethynyl)phenyl]-6-iodo-2,3-dihydrospiro[[1,3]diazolo[1,2-a]imidazole-1,1'-cyclopropane]-2-one (Example 9) and tributyl(pyrimidin-4-yl)stannane (commercial) | 440.2 |
| 19 | 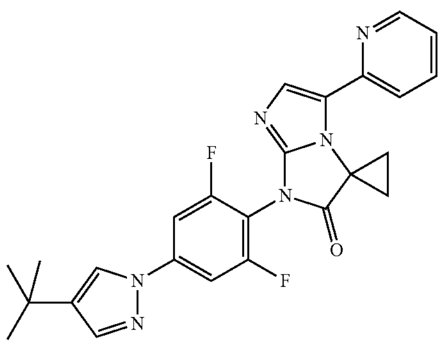 [SMILES: CC(C)(C)c1cnn(-c2cc(F)c(N3C(=O)C4(CC4)n4c(-c5ccccn5)cnc43)c(F)c2)c1] | 7'-[4-(4-tert-butylpyrazol-1-yl)-2,6-difluoro-phenyl]-3'-(2-pyridyl)spiro[cyclopropane-1,5'-imidazo[1,2-a]imidazole]-6'-one | 7'-[4-(4-tert-butylpyrazol-1-yl)-2,6-difluoro-phenyl]-3'-iodo-spiro[cyclopropane-1,5'-imidazo[1,2-a]imidazole]-6'-one (Example C.4) and 2-(tributylstannyl)pyridine (commercial) | 461.1 |
| 20 | 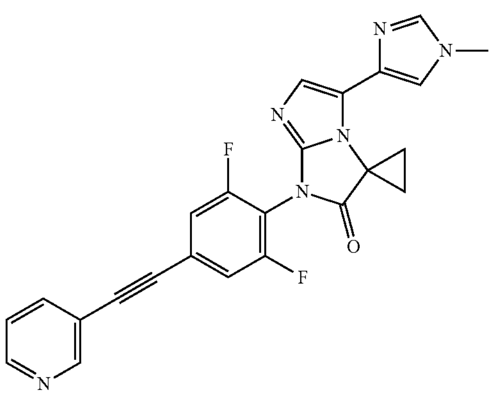 [SMILES: Cn1cnc(-c2cnc3n2C2(CC2)C(=O)N3c2c(F)cc(C#Cc3cccnc3)cc2F)c1] | 7'-[2,6-difluoro-4-[2-(3-pyridypethynyl]phenyl]-3'-(1-methylimidazol-4-yl)spiro[cyclopropane-1,5'-imidazo[1,2-a]imidazole]-6'-one | 7'-[2,6-difluoro-4-[2-(3-pyridyl)ethynyl]phenyl]-3'-iodo-spiro[cyclopropane-1,5'-imidazo[1,2-a]imidazole]-6'-one (Example C.8) and tributyl-(1-methylimidazol-4-yl)stannane (commercial) | 443.1 |
| 21 | 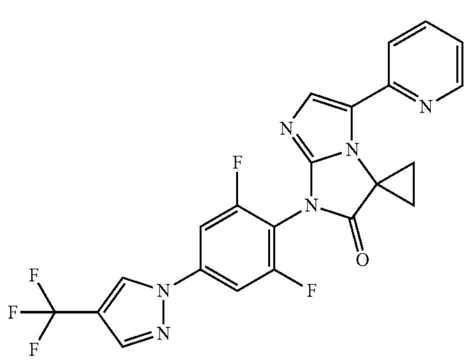 [SMILES: O=C1N(c2c(F)cc(-n3cc(C(F)(F)F)cn3)cc2F)c2ncc(-c3ccccn3)n2C12CC2] | 7'-[2,6-difluoro-4-[4-(trifluoromethyl)pyrazol-1-yl]phenyl]-3'-(2-pyridyl)spiro[cyclopropane-1,5'-imidazo[1,2-a]imidazole]-6'-one | 7'-[2,6-difluoro-4-[4-(trifluoromethyl)pyrazol-1-yl]phenyl]-3'-iodo-spiro[cyclopropane-1,5'-imidazo[1,2-a]imidazole]-6'-one (Example C.7) and 2-(tributylstannyl)pyridine (commercial) | 473.2 |

-continued

| Example No. | Structure | Systematic Name | Starting materials | MW found (M + H) |
|---|---|---|---|---|
| 22 | 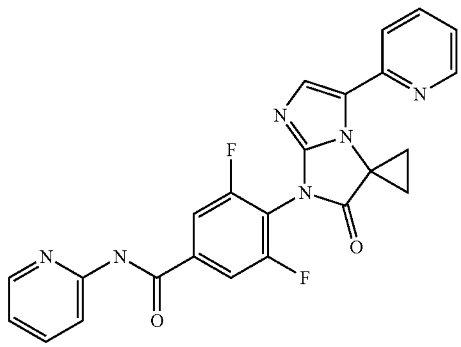 [SMILES: O=C(Nc1ccccn1)c1cc(F)c(N2C(=O)C3(CC3)n3c(-c4ccccn4)cnc32)c(F)c1] | 3,5-difluoro-4-[6'-oxo-3'-(2-pyridyl)spiro[cyclopropane-1,5'-imidazo[1,2-a]imidazole]-7'-yl]-N-(2-pyridyl)benzamide | 3,5-difluoro-4-(3'-iodo-6'-oxo-spiro[cyclopropane-1,5'-imidazo[1,2-a]imidazole]-7'-yl)-N-(2-pyridyl)benzamide (Example C.5) and 2-(tributylstannyl)pyridine (commercial) | 459.1 |
| 23 | 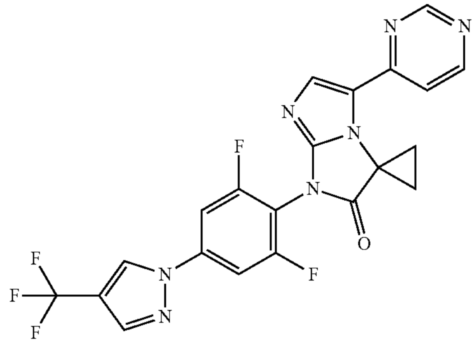 [SMILES: O=C1N(c2c(F)cc(-n3cc(C(F)(F)F)cn3)cc2F)c2ncc(-c3ccncn3)n2C12CC2] | 7'-[2,6-difluoro-4-[4-(trifluoromethyl)pyrazol-1-yl]phenyl]-3'-pyrimidin-4-yl-spiro[cyclopropane-1,5'-imidazo[1,2-a]imidazole]-6'-one | 7'-[2,6-difluoro-4-[4-(trifluoromethyl)pyrazol-1-yl]phenyl]-3'-iodo-spiro[cyclopropane-1,5'-imidazo[1,2-a]imidazole]-6'-one (Example C.7) and tributyl(pyrimidin-4-yl)stannane (commercial) | 474.2 |

Example 24

Preparation of 3-[2,6-Difluoro-4-(2-phenylethynyl)phenyl]-6-phenyl-2,3-dihydrospiro[[1,3]diazolo[1,2-a]imidazole-1,1'-cyclopropane]-2-one

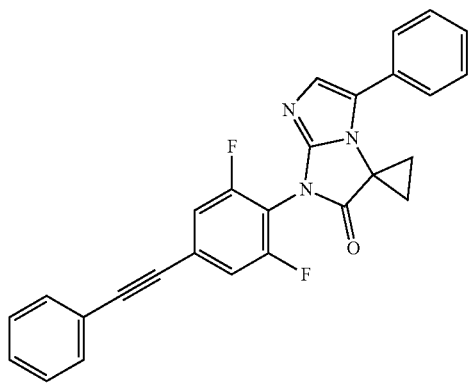 [SMILES: O=C1N(c2c(F)cc(C#Cc3ccccc3)cc2F)c2ncc(-c3ccccc3)n2C12CC2]

To a solution of 3'-[2,6-difluoro-4-(2-phenylethynyl)phenyl]-6'-iodo-2',3'-dihydrospiro[cyclopropane-1,1'-imidazo[1,2-a][1,3]diazole]-2'-one (Example 9) (50 mg, 0.103 mmol, 1 eq.) and phenyl boronic acid (18.8 mg, 0.154 mmol, 1.5 eq.) in DMF (2 ml) and H$_2$O (0.5 ml) were added Na$_2$CO$_3$ (53.9 mg, 0.513 mmol, 5 eq.) and PPh$_3$ (10.8 mg, 0.041 mmol, 0.4 eq.) at 25° C. and the reaction mixture was purged with argon for 10 min. Then Pd(OAc)$_2$ (4.6 mg, 0.021 mmol, 0.2 eq.) was added and the reaction mixture again purged with argon for 10 min. The reaction mixture was stirred at 80° C. for 3 h, then cooled to 25° C., diluted with EtOAc and filtered through celite. The organic layer was washed with water and brine, dried over Na$_2$SO$_4$ and concentrated in vacuo. The resulting crude was purified by prep-HPLC (NH$_4$OAc/CH$_3$CN) to yield 3-[2,6-difluoro-4-(2-phenylethynyl)phenyl]-6-phenyl-2,3-dihydrospiro[[1,3]diazolo-[1,2-a imidazole-1,1'-cyclopropane]-2-one (4 mg, 9%) as an off-white solid. M+H+=438.0.

In analogy to Example 24, Examples 25-39 and D.1, of the following table were prepared from the iodides 8-10 and C.1-C.8 and the commercially available boronic acid or boronic ester derivatives using a Suzuki cross-coupling:

| Example No. | Structure | Systematic Name | Starting materials | MW found (M + H) |
|---|---|---|---|---|
| 25 | 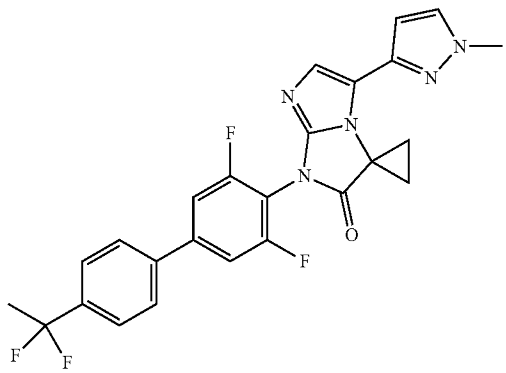 [SMILES: Cn1ccc(-c2cnc3n2C2(CC2)C(=O)N3c2c(F)cc(-c3ccc(C(C)(F)F)cc3)cc2F)n1] | 7'-[4-[4-(1,1-difluoroethyl)phenyl]-2,6-difluoro-phenyl]-3'-(1-methylpyrazol-3-yl)spiro[cyclopropane-1,5'-imidazo[1,2-a]imidazole]-6'-one | 7'-[4-[4-(1,1-difluoroethyl)phenyl]-2,6-difluoro-phenyl]-3'-iodo-spiro[cyclopropane-1,5'-imidazo[1,2-a]imidazole]-6'-one (Example C.2) and 1-methyl-3-(4,4,5,5-tetramethyl-1,3,2-dioxaborolan-2-yl)-1H-pyrazole (commercial) | 481.9 |
| 26 | 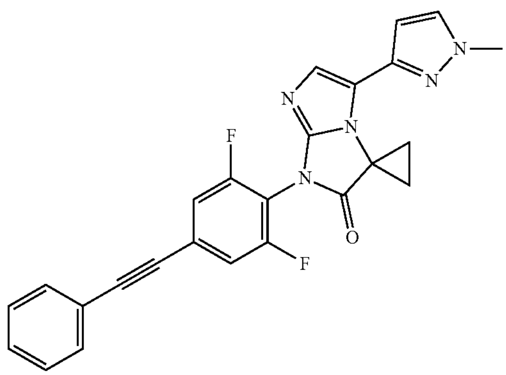 [SMILES: Cn1ccc(-c2cnc3n2C2(CC2)C(=O)N3c2c(F)cc(C#Cc3ccccc3)cc2F)n1] | 1'-(2,6-difluoro-4-(phenylethynyl)phenyl)-5'-(1-methyl-1H-pyrazol-3-yl)spiro[cyclopropane-1,3'-imidazo[1,2-a]imidazol]-2'(1'H)-one | 3'-[2,6-difluoro-4-(2-phenylethynyl)phenyl]-6'-iodo-2',3'-dihydrospiro[cyclopropane-1,1'-imidazo[1,2-a][1,3]diazole]-2'-one (Example 9) and 1-methyl-3-(4,4,5,5-tetramethyl-1,3,2-dioxaborolan-2-yl)-1H-pyrazole (commercial) (DME used in place of DMF) | 442.3 |
| 27 | 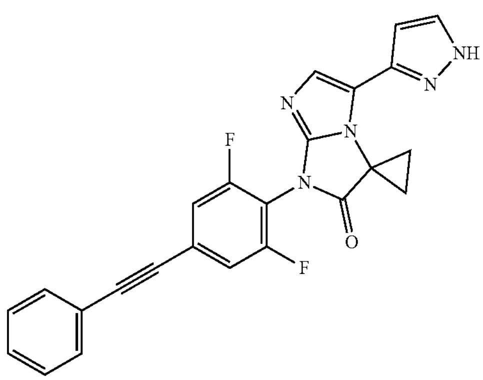 [SMILES: O=C1N(c2c(F)cc(C#Cc3ccccc3)cc2F)c2ncc(-c3cc[nH]n3)n2C12CC2] | 3-[2,6-Difluoro-4-(2-phenylethynyl)phenyl]-6-(1H-pyrazol-3-yl)-2,3-dihydrospiro[[1,3]diazolo[1,2-a]-imidazole-1,1'-cyclopropane]-2-one | 3'-[2,6-difluoro-4-(2-phenylethynyl)phenyl]-6'-iodo-2',3'-dihydrospiro[cyclopropane-1,1'-imidazo[1,2-a][1,3]diazole]-2'-one (Example 9) and pyrazole-3-boronic acid pinacol ester (commercial) | 428.2 |
| 28 | 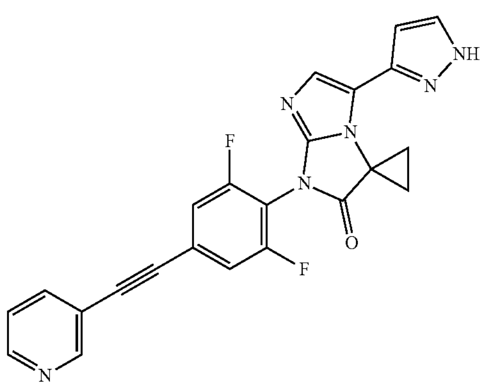 [SMILES: O=C1N(c2c(F)cc(C#Cc3cccnc3)cc2F)c2ncc(-c3cc[nH]n3)n2C12CC2] | 7'-[2,6-difluoro-4-[2-(3-pyridyl)ethynyl]phenyl]-3'-(1H-pyrazol-3-yl)spiro[cyclopropane-1,5'-imidazo[1,2-a]imidazole]-6'-one | 7'-[2,6-difluoro-4-[2-(3-pyridyl)ethynyl]phenyl]-3'-iodo-spiro[cyclopropane-1,5'-imidazo[1,2-a]imidazole]-6'-one (Example C.8) and pyrazole-3-boronic acid pinacol ester (commercial) | 429.1 |

-continued

| Example No. | Structure | Systematic Name | Starting materials | MW found (M + H) |
|---|---|---|---|---|
| 29 | 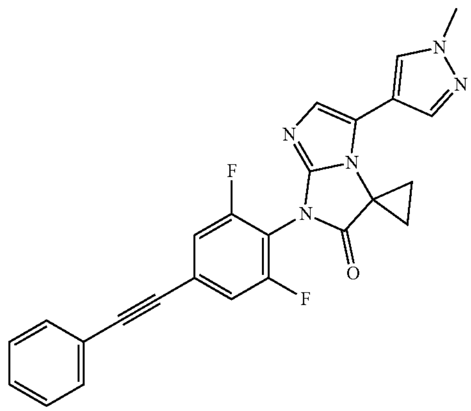 [SMILES: Cn1cc(-c2cnc3n2C2(CC2)C(=O)N3c2c(F)cc(C#Cc3ccccc3)cc2F)cn1] | 3-[2,6-Difluoro-4-(2-phenylethynyl)phenyl]-6-(1-methyl-1H-pyrazol-4-yl)-2,3-dihydrospiro[[1,3]diazolo[1,2-a]imidazole-1,1'-cyclopropane]-2-one | 3'-[2,6-difluoro-4-(2-phenylethynyl)phenyl]-6'-iodo-2',3'-dihydrospiro[cyclopropane-1,1'-imidazo[1,2-a][1,3]diazole]-2'-one (Example 9) and 1-methyl-1H-pyrazole-4-boronic acid pinacol ester (commercial) | 442.1 |
| 30 | 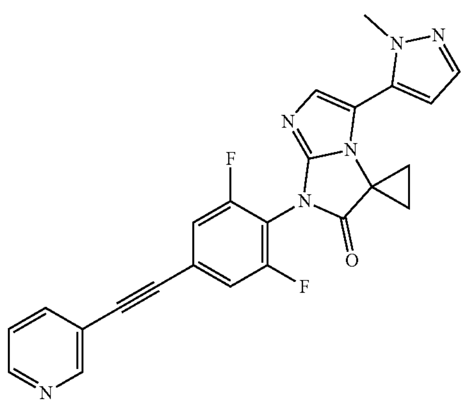 [SMILES: Cn1nccc1-c1cnc2n1C1(CC1)C(=O)N2c1c(F)cc(C#Cc2cccnc2)cc1F] | 7'-[2,6-difluoro-4-[2-(3-pyridyl)ethynyl]phenyl]-3'-(2-methylpyrazol-3-yl)spiro[cyclopropane-1,5'-imidazo[1,2-a]imidazole]-6'-one | 7'-[2,6-difluoro-4-[2-(3-pyridyl)ethynyl]phenyl]-3'-iodo-spiro[cyclopropane-1,5'-imidazo[1,2-a]imidazole]-6'-one (Example C.8) and 1-methyl-1H-pyrazole-5-boronic acid pinacol ester (commercial) | 443.0 |
| 31 | 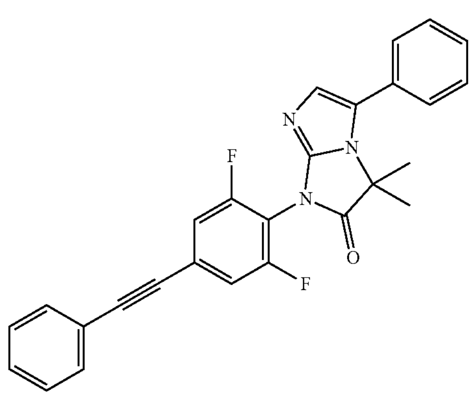 [SMILES: CC1(C)C(=O)N(c2c(F)cc(C#Cc3ccccc3)cc2F)c2ncc(-c3ccccc3)n21] | 1-(2,6-difluoro-4-(phenylethynyl)phenyl)-3,3-dimethyl-5-phenyl-1H-imidazo[1,2-a]imidazol-2(3H)-one | 1-(2,6-difluoro-4-(phenylethynyl)phenyl)-5-iodo-3,3-dimethyl-1H-imidazo[1,2-a]imidazol-2(3H)-one (Example 8) and phenyl boronic acid pinacol ester (commercial) (DME used in place of DMF) | 440.3 |

-continued

| Example No. | Structure | Systematic Name | Starting materials | MW found (M + H) |
|---|---|---|---|---|
| 32 | 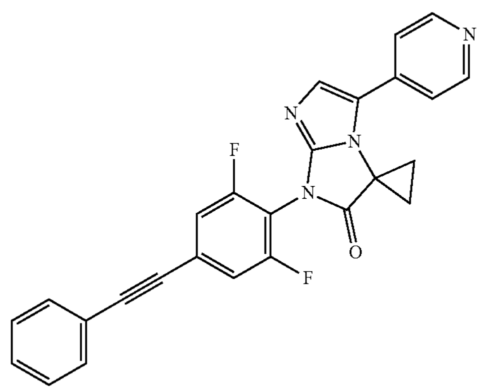 [SMILES: O=C1N(c2c(F)cc(C#Cc3ccccc3)cc2F)c2ncc(-c3ccncc3)n2C12CC2] | 3-[2,6-Difluoro-4-(2-phenylethynyl)phenyl]-6-(pyridin-4-yl)-2,3-dihydrospiro[[1,3]diazolo[1,2-a]imidazole-1,1'-cyclopropane]-2-one | 3'-[2,6-difluoro-4-(2-phenylethynyl)phenyl]-6'-iodo-2',3'-dihydrospiro[cyclopropane-1,1'-imidazo[1,2-a][1,3]diazole]-2'-one (Example 9) and pyridine-4-boronic acid (commercial) | 439.2 |
| 33 | 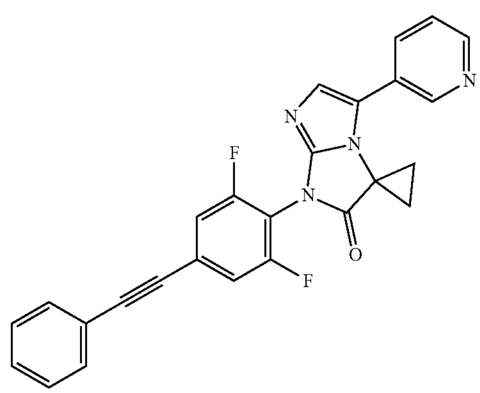 [SMILES: O=C1N(c2c(F)cc(C#Cc3ccccc3)cc2F)c2ncc(-c3cccnc3)n2C12CC2] | 3-[2,6-Difluoro-4-(2-phenylethynyl)phenyl]-6-(pyridin-3-yl)-2,3-dihydrospiro[[1,3]diazolo[1,2-a]imidazole-1,1'-cyclopropane]-2-one | 3'-[2,6-difluoro-4-(2-phenylethynyl)phenyl]-6'-iodo-2',3'-dihydrospiro[cyclopropane-1,1'-imidazo[1,2-a][1,3]diazole]-2'-one (Example 9) and pyridine-3-boronic acid (commercial) | 439.1 |
| 34 | 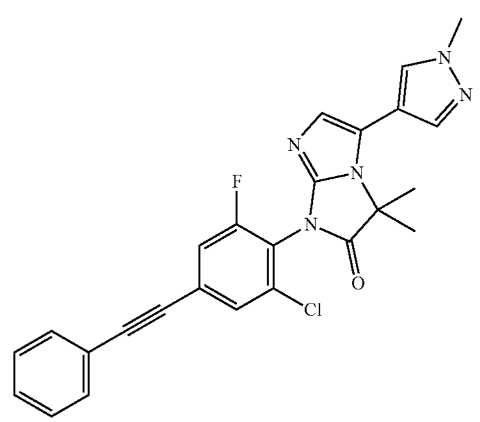 [SMILES: Cn1cc(-c2cnc3n2C(C)(C)C(=O)N3c2c(F)cc(C#Cc3ccccc3)cc2Cl)cn1] | 1-(2-chloro-6-fluoro-4-(phenylethynyl)phenyl)-3,3-dimethyl-5-(1-methyl-1H-pyrazol-4-yl)-1H-imidazo[1,2-a]imidazol-2(3H)-one | 1-(2-chloro-6-fluoro-4-(phenylethynyl)phenyl)-5-iodo-3,3-dimethyl-1H-imidazo[1,2-a]imidazol-2(3H)-one (Example 10) and 1-methyl-1H-pyrazole-4-boronic acid pinacol ester) (commercial) (DME used in place of DMF) | 460.2 |

-continued

| Example No. | Structure | Systematic Name | Starting materials | MW found (M + H) |
|---|---|---|---|---|
| 35 | 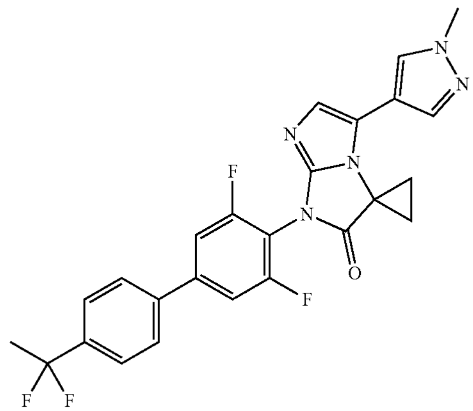 [SMILES: Cn1cc(-c2cnc3n2C2(CC2)C(=O)N3c2c(F)cc(-c3ccc(C(C)(F)F)cc3)cc2F)cn1] | 1'-(4'-(1,1-difluoroethyl)-3,5-difluoro-[1,1'-biphenyl]-4-yl)-5'-(1-methyl-1H-pyrazol-4-yl)spiro[cyclopropane-1,3'-imidazo[1,2-a]imidazol]-2'(1'H)-one | 7'-[4-[4-(1,1-difluoroethyl)phenyl]-2,6-difluoro-phenyl]-3'-iodo-spiro[cyclopropane-1,5'-imidazo[1,2-a]imidazole]-6'-one (Example C.2) and 1-methyl-1H-pyrazole-4-boronic acid pinacol ester (commercial) (DME used in place of DMF) | 482.2 |
| 36 | 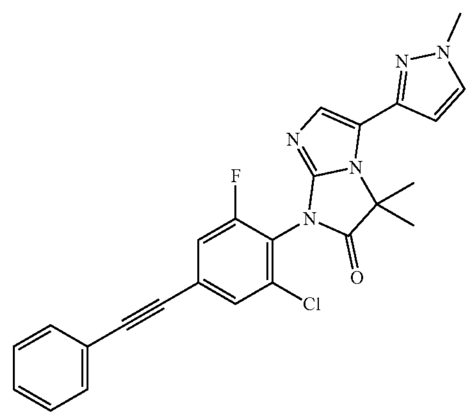 [SMILES: Cn1ccc(-c2cnc3n2C(C)(C)C(=O)N3c2c(F)cc(C#Cc3ccccc3)cc2Cl)n1] | 1-(2-chloro-6-fluoro-4-(phenylethynyl)phenyl)-3,3-dimethyl-5-(1-methyl-1H-pyrazol-3-yl)-1H-imidazo[1,2-a]imidazol-2(3H)-one | 1-(2-chloro-6-fluoro-4-(phenylethynyl)phenyl)-5-iodo-3,3-dimethyl-1H-imidazo[1,2-a]imidazol-2(3H)-one (Example 10) and tert-butyl 3-(4,4,5,5-tetramethyl-1,3,2-dioxaborolan-2-yl)-1H-pyrazole-1-carboxylate (commercial) (DME used in place of DMF) | 460.2 |
| 37 | 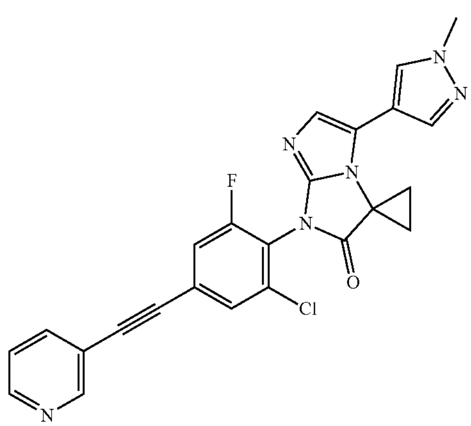 [SMILES: Cn1cc(-c2cnc3n2C2(CC2)C(=O)N3c2c(F)cc(C#Cc3cccnc3)cc2Cl)cn1] | 1'-(2,6-difluoro-4-(pyridin-3-ylethynyl)phenyl)-5'-(1-methyl-1H-pyrazol-4-yl)spiro[cyclopropane-1,3'-imidazo[1,2-a]imidazol]-2'(1'H)-one | 7'-[2,6-difluoro-4-[2-(3-pyridyl)ethynyl]phenyl]-3'-iodo-spiro[cyclopropane-1,5'-imidazo[1,2-a]imidazole]-6'-one (Example C.8) and 1-methyl-1H-pyrazole-4-boronic acid pinacol ester (commercial) (DME used in place of DMF) | 443.3 |

-continued

| Example No. | Structure | Systematic Name | Starting materials | MW found (M + H) |
|---|---|---|---|---|
| 38 | 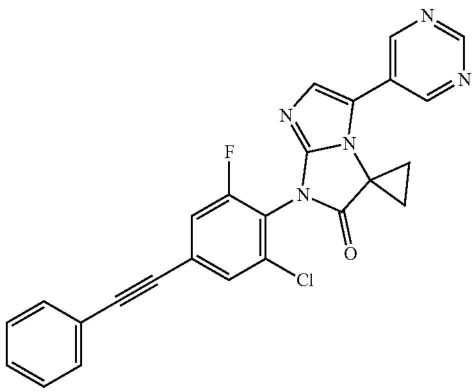 [SMILES: O=C1N(c2c(F)cc(C#Cc3ccccc3)cc2Cl)c2ncc(-c3cncnc3)n2C12CC2] | 3-[2,6-Difluoro-4-(2-phenylethynyl)phenyl]-6-(pyrimidin-5-yl)-2,3-dihydrospiro[[1,3]diazolo[1,2-a]imidazole-1,1'-cyclopropane]-2-one | 3'-[2,6-difluoro-4-(2-phenylethynyl)phenyl]-6'-iodo-2',3'-dihydrospiro[cyclopropane-1,1'-imidazo[1,2-a][1,3]diazole]-2'-one (Example 9) and 5-pyrimidine boronic acid pinacol ester (commercial) | 440.2 |
| 39 | 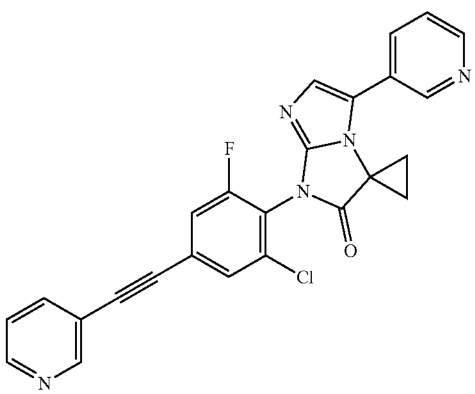 [SMILES: O=C1N(c2c(F)cc(C#Cc3cccnc3)cc2Cl)c2ncc(-c3cccnc3)n2C12CC2] | 1'-(2,6-difluoro-4-(pyridin-3-ylethynyl)phenyl)-5'-(pyridin-3-yl)spiro[cyclopropane-1,3'-imidazo[1,2-a]imidazol]-2'(1'H)-one | 7'-[2,6-difluoro-4-[2-(3-pyridyl)ethynyl]phenyl]-3'-iodo-spiro[cyclopropane-1,5'-imidazo[1,2-a]imidazole]-6'-one (Example C.8) and pyridine-3-boronic acid (commercial) (DME used in place of DMF) | 440.3 |
| D.1 | 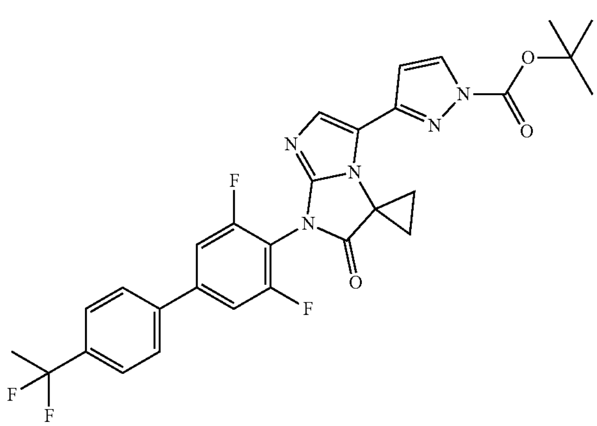 [SMILES: CC(C)(C)OC(=O)n1ccc(-c2cnc3n2C2(CC2)C(=O)N3c2c(F)cc(-c3ccc(C(C)(F)F)cc3)cc2F)n1] | tert-butyl 3-(1'-(4'-(1,1-difluoroethyl)-3,5-difluoro-[1,1'-biphenyl]-4-yl)-2'-oxo-1',2'-dihydrospiro[cyclopropane-1,3'-imidazo[1,2-a]imidazol]-5'-yl)-1H-pyrazole-1-carboxylate | 7'-[4-[4-(1,1-difluoroethyl)phenyl]-2,6-difluoro-phenyl]-3'-iodo-spiro[cyclopropane-1,5'-imidazo[1,2-a]imidazole]-6'-one (Example C.2) and tert-butyl 3-(4,4,5,5-tetramethyl-1,3,2-dioxaborolan-2-yl)-1H-pyrazole-1-carboxylate (commercial) (DME used in place of DMF) | 568.3 |

Example 40

Preparation of 1'-(4'-(1,1-difluoroethyl)-3,5-difluoro-[1,1'-biphenyl]-4-yl)-5'-(1H-pyrazol-3-yl)spiro[cyclopropane-1,3'-imidazo[1,2-a]imidazol]-2'(1'H)-one

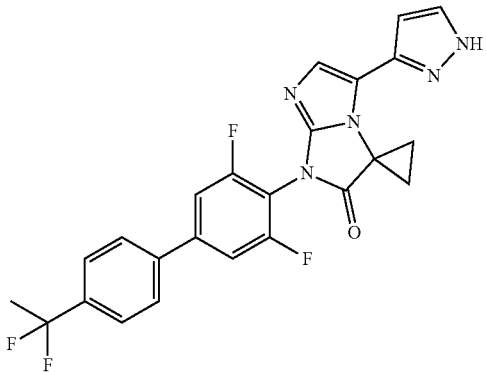 [SMILES: CC(F)(F)c1ccc(-c2cc(F)c(N3C(=O)C4(CC4)n4c(-c5cc[nH]n5)cnc43)c(F)c2)cc1]

To a solution of tert-butyl 3-(1'-(4'-(1,1-difluoroethyl)-3,5-difluoro-[1,1'-biphenyl]-4-yl)-2'-oxo-1',2'-dihydrospiro[cyclopropane-1,3'-imidazo[1,2-a]imidazol]-5'-yl)-1H-pyrazole-1-carboxylate (20 mg, 35.2 µmol, 1 eq.) (Example D.1) in 1,4-dioxane (350 µl) was added HCl (4M in dioxane) (8.81 µl, 35.2 µmol, 1 eq.) at 25° C. under argon. The mixture was stirred for 16 hr while increasing temperature from 40° C. to 80° C. until full Boc deprotection was observed on TLC and LCMS. The reaction mixture was concentrated in vacuo. The crude material was purified by flash chromatography on silica gel (20% to 100% EtOAc in heptane) to yield 1'-(4'-(1,1-difluoroethyl)-3,5-difluoro-[1,1'-biphenyl]-4-yl)-5'-(1H-pyrazol-3-yl)spiro[cyclopropane-1,3'-imidazo[1,2-a]imidazol]-2'(1'H)-one (11.7 mg, 25 µmol, 71% yield) as an off-white solid. M+H+=468.3.

Example 41

Preparation of 3-[2,6-Difluoro-4-(2-phenylethynyl)phenyl]-6-(1H-pyrazol-4-yl)-2,3-dihydrospiro[[1,3]diazolo[1,2-a]imidazole-1,1'-cyclopropane]-2-one

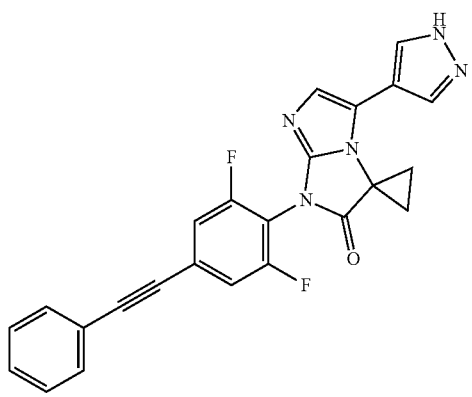 [SMILES: O=C1N(c2c(F)cc(C#Cc3ccccc3)cc2F)c2ncc(-c3cn[nH]c3)n2C12CC2]

To a stirred solution of 3'-[2,6-difluoro-4-(2-phenylethynyl)phenyl]-6'-iodo-2',3'-dihydrospiro[cyclopropane-1,1'-imidazo[1,2-a][1,3]diazole]-2'-one (Example 9) (100 mg, 0.205 mmol) in dioxane (10 ml) and water (1.25 ml) at 25° C. were added 1-Boc-pyrazole-4-boronic acid pinacol ester (181 mg, 0.616 mmol) and K$_2$CO$_3$ (85 mg, 0.616 mmol) and reaction mixture was purged with argon for 10 min. Then PdCl$_2$(dppf).CH$_2$Cl$_2$ (8 mg, 0.01 mmol) was added and the reaction mixture was stirred at 80° C. for 1 h. The reaction mixture was diluted with EtOAc (30 ml) and washed with water (30 ml) and brine (20 ml). The organic layer was dried over anhydrous Na$_2$SO$_4$ and concentrated under reduced pressure. The resulting crude was purified by column chromatography over silica gel (30-40% EtOAc in hexane) to get the Boc protected compound along with some impurities as a sticky solid (115 mg) that was dissolved in anhydrous CH$_2$C$_2$ (5 ml) and 4M HCl in dioxane (1 ml) was added at 0° C. The reaction mixture was stirred at 25° C. for 16 h. The solvent was evaporated under reduced pressure and the resulting crude material was purified by prep HPLC (NH$_4$OAc/CH$_3$CN) to get 3-[2,6-difluoro-4-(2 phenylethynyl)phenyl]-6-(1H-pyrazol-4-yl)-2,3-dihydrospiro[[1,3]diazolo[1,2-a]imidazole-1,1'-cyclopropane]-2-one (20 mg, 23%) as a white solid. M+H+=428.2.

Example 42

Preparation of 7'-[2,6-difluoro-4-[4-(2,2,2-trifluoroethyl)piperazin-1-yl]phenyl]-3'-(1H-pyrazol-3-yl)spiro[cyclopropane-1,5'-imidazo[1,2-a]imidazole]-6'-one

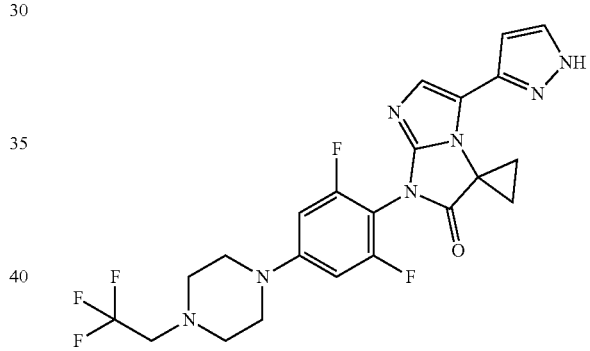

To a solution of compound 7'-[2,6-difluoro-4-[4-(2,2,2-trifluoroethyl)piperazin-1-yl]phenyl]-3'-iodo-spiro[cyclopropane-1,5'-imidazo[1,2-a]imidazole]-6'-one (Example C.3) (100 mg, 0.180 mmol, 1 eq.) and 3-(4,4,5,5-tetramethyl-1,3,2-dioxaborolan-2-yl)-1H-pyrazole (70 mg, 0.360 mmol, 2 eq.) in DMF (3 ml) and water (0.03 ml) was added Na$_2$CO$_3$ (38 mg, 0.360 mmol, 2 eq.) at 25° C. and the reaction mixture was purged with argon for 10 min. Then Pd(PPh$_3$)$_4$ (21 mg, 0.020 mmol, 0.1 eq.) was added and the reaction mixture was again purged with argon for 10 min. Then the reaction mixture was stirred at 80° C. for 2 h. The reaction was taken up in EtOAc (100 ml) and the organics were washed with water (2×30 ml) and brine (30 ml). The organics were dried over Na$_2$SO$_4$ and concentrated in vacuo. The crude was then purified by preparative HPLC (NH$_4$OAc/CH$_3$CN) followed by concentration and lyophilization to afford 7'-[2,6-difluoro-4-[4-(2,2,2-trifluoroethyl)piperazin-1-yl]phenyl]-3'-(1H-pyrazol-3-yl)spiro[cyclopropane-1,5'-imidazo[1,2-a]imidazole]-6'-one (38.6 mg, 0.080 mmol, 43% yield) as a white solid. M+H+=494.1.

In analogy to Example 42, Examples 43-46, of the following table were prepared from the iodides Examples 9, C.1, C.6 and C.8 and the commercially available boronic acid or boronic ester derivatives using a Suzuki cross-coupling:

| Example No. | Structure | Systematic Name | Starting materials | MW found (M + H) |
|---|---|---|---|---|
| 43 | 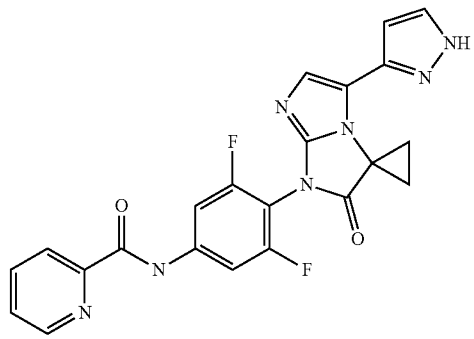 [SMILES: O=C(Nc1cc(F)c(N2C(=O)C3(CC3)n3c(-c4cc[nH]n4)cnc32)c(F)c1)c1ccccn1] | N-[3,5-difluoro-4-[6'-oxo-3'-(1H-pyrazol-3-yl)spiro[cyclopropane-1,5'-imidazo[1,2-a]imidazole]-7'-yl]phenyl]pyridine-2-carboxamide | N-[3,5-difluoro-4-(3'-iodo-6'-oxo-spiro[cyclopropane-1,5'-imidazo[1,2-a]imidazole]-7'-yl)phenyl]pyridine-2-carboxamide (Example C.1) and 3-(4,4,5,5-tetramethyl-1,3,2-dioxaborolan-2-yl)-1H-pyrazole (commercial) (3 eq.) | 447.9 |
| 44 | 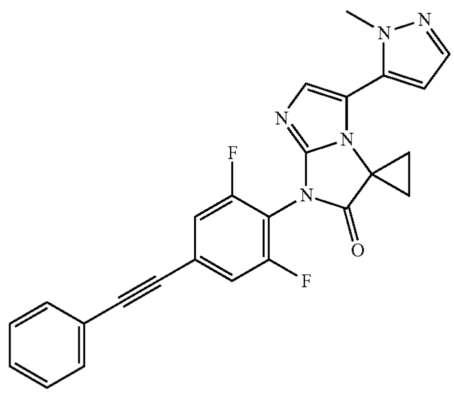 [SMILES: Cn1nccc1-c1cnc2n1C1(CC1)C(=O)N2c1c(F)cc(C#Cc2ccccc2)cc1F] | 7'[2,6-difluoro-4-(2-phenylethynyl)phenyl]-3'-(2-methylpyrazol-3-yl)spiro[cyclopropane-1,5'-imidazo[1,2-a]imidazole]-6'-one | 3'-[2,6-difluoro-4-(2-phenylethynyl)phenyl]-6'-iodo-2',3'-dihydrospiro[cyclopropane-1,1'-imidazo[1,2-a][1,3]diazole]-2'-one (Example 9) and 1-methyl-1H-pyrazole-5-boronic acid pinacol ester (commercial) (5 eq.) | 442.1 |
| 45 | 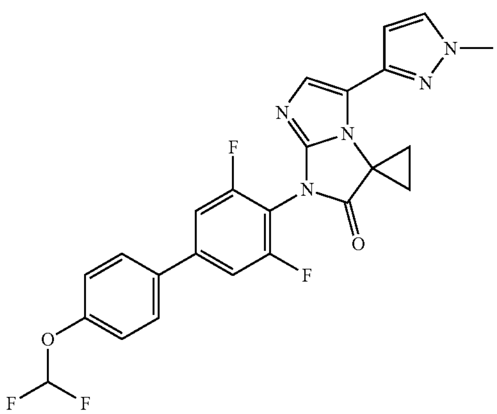 [SMILES: Cn1ccc(-c2cnc3n2C2(CC2)C(=O)N3c2c(F)cc(-c3ccc(OC(F)F)cc3)cc2F)n1] | 7'-[4-[4-(difluoromethoxy)phenyl]-2,6-difluoro-phenyl]-3'-(1-methylpyrazol-3-yl)spiro[cyclopropane-1,5'-imidazo[1,2-a]imidazole]-6'-one | 7'-[4-[4-(difluoromethoxy)phenyl]-2,6-difluoro-phenyl]-3'-iodo-spiro[cyclopropane-1,5'-imidazo[1,2-a]imidazole]-6'-one (Example C.6) and tert-butyl 3-(4,4,5,5-tetramethyl-1,3,2-dioxaborolan-2-yl)-1H-pyrazole-1-carboxylate (commercial) | 484.0 |
| 46 | 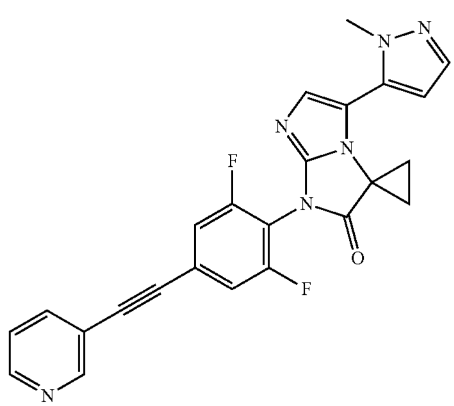 [SMILES: Cn1nccc1-c1cnc2n1C1(CC1)C(=O)N2c1c(F)cc(C#Cc2cccnc2)cc1F] | 7'-[2,6-difluoro-4-[2-(3-pyridypethynyl]phenyl]-3'-(2-methylpyrazol-3-yl)spiro[cyclopropane-1,5'-imidazo[1,2-a]imidazole]-6'-one | 7'-[2,6-difluoro-4-[2-(3-pyridyl)ethynyl]phenyl]-3'-iodo-spiro[cyclopropane-1,5'-imidazo[1,2-a]imidazole]-6'-one (Example C.8) and 1-methyl-1H-pyrazole-5-boronic acid pinacol ester (commercial) (5 eq.) | 443.0 |

Example 47

Preparation of 3-[2,6-Difluoro-4-(2-phenylethynyl)phenyl]-6-methyl-2,3-dihydrospiro[[1,3]diazolo[1,2-a]imidazole-1,1'-cyclopropane]-2-one

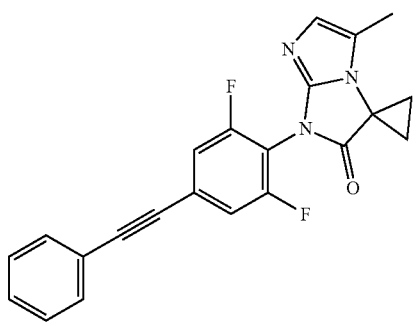 [SMILES: Cc1cnc2n1C1(CC1)C(=O)N2c1c(F)cc(C#Cc2ccccc2)cc1F]

To a solution of 3-[2,6-difluoro-4-(2-phenylethynyl)phenyl]-6-iodo-2,3-dihydrospiro[[1,3]diazolo[1,2-a]imidazole-1,1'-cyclopropane]-2-one (Example 9) (80 mg, 0.164 mmol, 1 eq.) and trimethyl boroxine (0.088 ml, 0.624 mmol, 3.8 eq.) in 1,4-dioxane was added $K_2CO_3$ (45.3 mg, 0.329 mmol, 2 eq.) at 25° C. and the reaction mixture was purged with argon for 10 min. Then Pd(dppf)$Cl_2$·$CH_2Cl_2$ (5.4 mg, 0.007 mmol, 0.04 eq.) was added to reaction mixture and the reaction mixture was again purged with argon for 10 min. The reaction mixture was stirred at 100° C. for 5 h. The solvent was evaporated under reduced pressure and the crude product was purified by prep-HPLC ($NH_4$OAc/$CH_3CN$) to yield 3-[2,6-difluoro-4-(2-phenylethynyl)phenyl]-6-methyl-2,3-dihydrospiro[[1,3]diazolo[1,2-a]imidazole-1,1'-cyclopropane]-2-one (9 mg, 15%) as an off-white solid. M+H+=376.2.

In analogy to Example 47, Examples 48-49, of the following table were prepared from the iodides C.1 and C.8 and trimethyl boroxine using a Suzuki cross-coupling:

| Example No. | Structure | Systematic Name | Starting materials | MW found (M + H) |
|---|---|---|---|---|
| 48 | 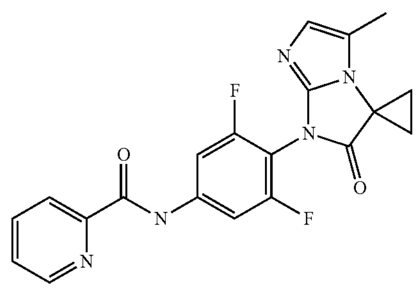 [SMILES: Cc1cnc2n1C1(CC1)C(=O)N2c1c(F)cc(NC(=O)c2ccccn2)cc1F] | N-[3,5-difluoro-4-(3'-methyl-6'-oxo-spiro[cyclopropane-1,5'-imidazo[1,2-a]imidazole]-7'-yl)phenyl]pyridine-2-carboxamide | N-[3,5-difluoro-4-(3'-iodo-6'-oxo-spiro[cyclopropane-1,5'-imidazo[1,2-a]imidazole]-7'-yl)phenyl]pyridine-2-carboxamide (Example C.1) and trimethyl boroxine (4 eq.), $K_2CO_3$ (3 eq.) and Pd(dppf)$Cl_2$·$CH_2Cl_2$ (0.1 eq.) | 396.1 |
| 49 | 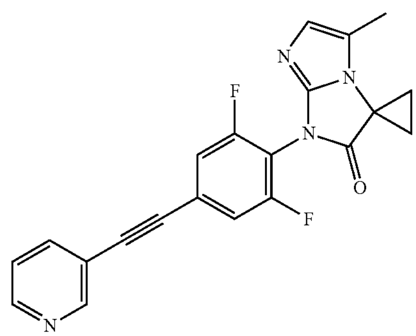 [SMILES: Cc1cnc2n1C1(CC1)C(=O)N2c1c(F)cc(C#Cc2cccnc2)cc1F] | 7'-[2,6-difluoro-4-[2-(3-pyridyl)ethynyl]phenyl]-3'-methyl-spiro[cyclopropane-1,5'-imidazo[1,2-a]imidazole]-6'-one | 7'-[2,6-difluoro-4-[2-(3-pyridyl)ethynyl]phenyl]-3'-iodo-spiro[cyclopropane-1,5'-imidazo[1,2-a]imidazole]-6'-one (Example C.8) and trimethyl boroxine (4 eq.), $K_2CO_3$ (3 eq.) and Pd(dppf)$Cl_2$·$CH_2Cl_2$ (0.1 eq.) | 377.0 |

Example 50

Preparation of 7'-[2,6-difluoro-4-(2-phenylethynyl)phenyl]-3'-(3-hydroxyoxetan-3-yl)spiro[cyclopropane-1,5'-imidazo[1,2-a]imidazole]-6'-one

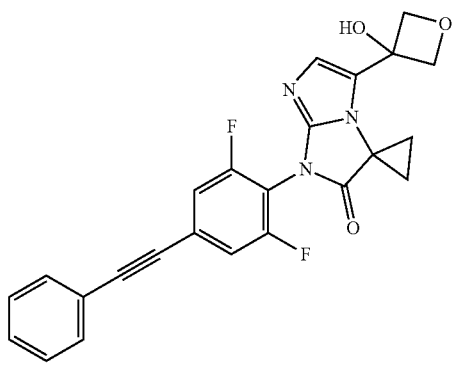 [SMILES: O=C1N(c2c(F)cc(C#Cc3ccccc3)cc2F)c2ncc(C3(O)COC3)n2C12CC2]

To a cold (0° C.) solution of 7'-[2,6-difluoro-4-(2-phenylethynyl)phenyl]-3'-iodo-spiro[cyclopropane-1,5'-imidazo[1,2-a]imidazole]-6'-one (Example 9) (200 mg, 0.410 mmol, 1 eq.) in THF (10 ml) was added iPrMgCl (2 M in THF) (0.31 ml, 0.620 mmol, 1.5 eq.) and the reaction mixture was stirred at 25° C. for for 1 h. The reaction mixture was cooled to 0° C. and 3-oxetanone (59 mg, 0.82 mmol, 2 eq.) was added. The reaction mixture was stirred at 25° C. for 12 h, then quenched with sat. aq. NH$_4$Cl solution and the reaction mixture extracted with EtOAc (3×30 ml). The combined organics were washed with water (20 ml) and brine (20 ml), dried over Na$_2$SO$_4$ and concentrated in vacuo. The crude product was purified by flash chromatography (80% EtOAc in hexane) and the evaporated solid was triturated with ether/pentane to afford 7'-[2,6-difluoro-4-(2-phenylethynyl)phenyl]-3'-(3-hydroxyoxetan-3-yl)spiro[cyclopropane-1,5'-imidazo[1,2-a]imidazole]-6'-one (35 mg, 0.080 mmol, 19% yield) as light yellow solid. M+H+=434.1.

Example 51

Preparation of N-[3,5-difluoro-4-[3'-(3-hydroxyoxetan-3-yl)-6'-oxo-spiro[cyclopropane-1,5'-imidazo[1,2-a]imidazole]-7'-yl]phenyl]pyridine-2-carboxamide

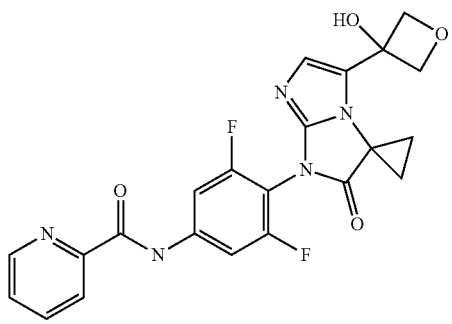 [SMILES: O=C(Nc1cc(F)c(N2C(=O)C3(CC3)n3c(C4(O)COC4)cnc32)c(F)c1)c1ccccn1]

To a solution of N-[3,5-difluoro-4-(3'-iodo-6'-oxo-spiro[cyclopropane-1,5'-imidazo[1,2-a]imidazole]-7'-yl)phenyl]pyridine-2-carboxamide (Example C.1) (200 mg, 0.390 mmol, 1 eq.) and 3-oxetanone (142 mg, 1.97 mmol, 5 eq.) in THF (6 ml) at −78° C. was added iPrMgCl (2 M in THF) (0.59 mL, 1.18 mmol, 3 eq.) and the reaction was stirred at same temperature for 3 h. The reaction mixture was allowed to warm to 25° C. and stirred for another 3 h. Reaction mixture was quenched with saturated aqueous NH$_4$Cl and extracted with ethyl acetate. The organic layers were dried over Na$_2$SO$_4$ and concentrated in vacuo. Resulting crude was purified by prep HPLC (NH$_4$OAc/CH$_3$CN) to yield N-[3,5-difluoro-4-[3'-(3-hydroxyoxetan-3-yl)-6'-oxo-spiro[cyclopropane-1,5'-imidazo[1,2-a]imidazole]-7'-yl]phenyl]pyridine-2-carboxamide (11 mg, 0.020 mmol, 6% yield). M+H+=454.2.

In analogy to Example 51, Example 52 of the following table were prepared from the iodide C.1 and trimethyl boroxine using a Suzuki cross-coupling:

| Example No. | Structure | Systematic Name | Starting materials | MW found (M + H) |
|---|---|---|---|---|
| 52 | 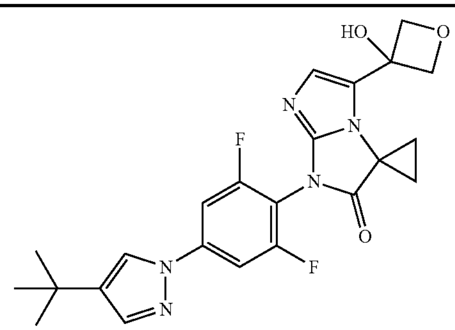 | 7'-[4-(4-tert-butylpyrazol-1-yl)-2,6-difluoro-phenyl]-3'-(3-hydroxyoxetan-3-yl)spiro[cyclopropane-1,5'-imidazo[1,2-a]imidazole]-6'-one | N-[3,5-difluoro-4-(3'-iodo-6'-oxo-spiro[cyclopropane-1,5'-imidazo[1,2-a]imidazole]-7'-yl)phenyl]pyridine-2-carboxamide (Example C.1) and 3-oxetanone (commercial) | 455.9 |

Example 53

Preparation of 3'-[2,6-Difluoro-4-(2-phenylethynyl)phenyl]-6'-methanesulfonyl-2',3'-dihydrospiro[cyclopropane-1,1'-imidazo[1,2-a][1,3]diazole]-2'-one

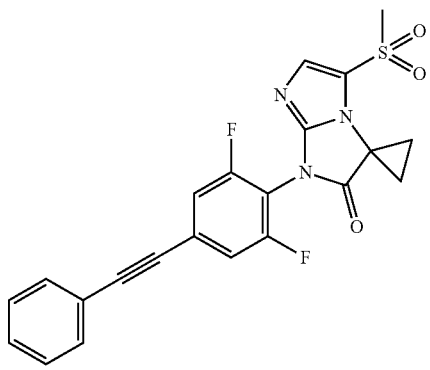 [SMILES: CS(=O)(=O)c1cnc2n1C1(CC1)C(=O)N2c1c(F)cc(C#Cc2ccccc2)cc1F]

To a solution of 3'-[2,6-difluoro-4-(2-phenylethynyl)phenyl]-6'-iodo-2',3'-dihydrospiro[cyclopropane-1,1'-imidazo[1,2-a][1,3]diazole]-2'-one (Example 9) (30 mg, 0.06 mmol) in THF (5 ml) at −40° C. was added cyclopentyl magnesium bromide (2M solution in diethyl ether) (0.09 ml, 0.09 mmol) and reaction mixture was stirred at 0° C. for 1 h. The reaction mixture was again cooled to −40° C. and mesyl chloride (0.019 ml, 0.25 mmol) was added, and the reaction mixture was stirred at 25° C. for 1 h. The reaction mixture was quenched with saturated aqueous $NH_4Cl$ solution and extracted with EtOAc (3×10 ml). The combined organic layers were washed with brine, dried over $Na_2SO_4$ and concentrated in vacuo. The crude product was purified by prep HPLC to afford 3'-[2,6-difluoro-4-(2-phenylethynyl)phenyl]-6'-methanesulfonyl-2',3'-dihydrospiro[cyclopropane-1,1'-imidazo[1,2-a][1,3]diazole]-2'-one (6 mg, 22%) as white solid. M+H+=440.0.

Example 54

Preparation of 7'-[2,6-difluoro-4-[2-(3-pyridyl)ethynyl]phenyl]-3'-(2-oxoazetidin-1-yl)spiro[cyclopropane-1,5'-imidazo[1,2-a]imidazole]-6'-one

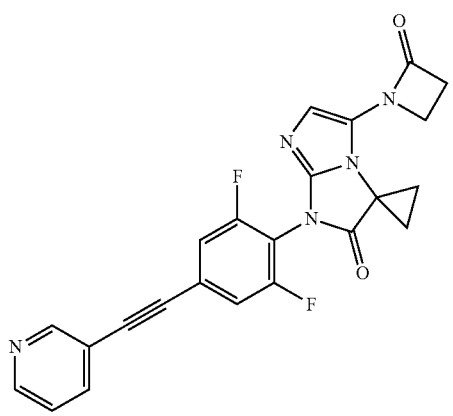 [SMILES: O=C1CCN1c1cnc2n1C1(CC1)C(=O)N2c1c(F)cc(C#Cc2cccnc2)cc1F]

To a solution of 7'-[2,6-difluoro-4-[2-(3-pyridyl)ethynyl]phenyl]-3'-iodo-spiro[cyclopropane-1,5'-imidazo[1,2-a]imidazole]-6'-one (Example 9) (50 mg, 0.130 mmol, 1 eq.) and 2-azetidinone (13.8 mg, 0.190 mmol, 1.5 eq.) in toluene (4 ml) were added phosphoric acid, potassium salt (54.8 mg, 0.260 mmol, 2 eq.), CuI (4.92 mg, 0.030 mmol, 0.2 eq.) and trans-N,N-dimethyl cyclohexane-1,2-diamine (3.7 mg, 0.030 mmol, 0.2 eq.) and reaction mixture was heated at 100° C. under an argon atmosphere for 16 h. The reaction mixture was diluted with ethyl acetate and washed with water. The organic layer was dried over $Na_2SO_4$ and concentrated in vacuo to get crude 7'-[2,6-difluoro-4-[2-(3-pyridyl)ethynyl]phenyl]-3'-(2-oxoazetidin-1-yl)spiro[cyclopropane-1,5'-imidazo[1,2-a]imidazole]-6'-one (55 mg, 0.130 mmol, 15% yield) as brown solid. This crude product was combined with a crude product (55 mg, 0.130 mmol, 12% yield) from an equivalent reaction that had had a 14 h reaction time. The combined crude products were purified by prep HPLC ($NH_4OAc/CH_3CN$) to yield 7'-[2,6-difluoro-4-[2-(3-pyridyl)ethynyl]phenyl]-3'-(2-oxoazetidin-1-yl)spiro[cyclopropane-1,5'-imidazo[1,2-a]imidazole]-6'-one (8 mg, 0.020 mmol, 8% yield) as off white solid. M+H+=432.1.

Example E.1

Preparation of 7'-[2,6-difluoro-4-(2-phenylethynyl)phenyl]-6'-oxo-spiro[cyclopropane-1,5'-imidazo[1,2-a]imidazole]-3'-carbaldehyde

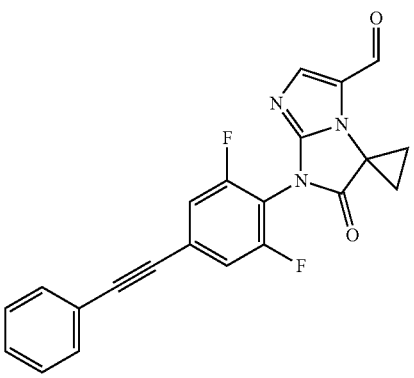 [SMILES: O=Cc1cnc2n1C1(CC1)C(=O)N2c1c(F)cc(C#Cc2ccccc2)cc1F]

To a solution of 7'-[2,6-difluoro-4-(2-phenylethynyl)phenyl]spiro[cyclopropane-1,5'-imidazo[1,2-a]imidazole]-6'-one (Example 1) (30.0 mg, 0.080 mmol, 1 eq.) in THF (3 ml) was added Vilsmeier reagent ((chloromethylene)dimethyliminium chloride) (32 mg, 0.250 mmol, 3 eq.) and the reaction mixture was stirred at 80° C. for for 2 h. The reaction was concentrated in vacuo, then diluted with ice water. The aqueous mixture was extracted with EtOAc (3×20 ml). The combined organics were washed with water, dried over $Na_2SO_4$, and concentrated in vacuo.

The crude material was triturated with hexane to afford 7'-[2,6-difluoro-4-(2-phenylethynyl)phenyl]-6'-oxo-spiro[cyclopropane-1,5'-imidazo[1,2-a]imidazole]-3'-carbaldehyde (35 mg, 0.090 mmol, 79% yield) which was used in subsequent steps without further purification. M+H+=390.1.

Example E.2

Preparation of N-[3,5-difluoro-4-(3'-formyl-6'-oxo-spiro[cyclopropane-1,5'-imidazo[1,2-a]imidazole]-7'-yl)phenyl]pyridine-2-carboxamide

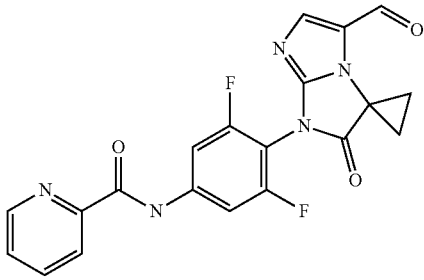 [SMILES: O=Cc1cnc2n1C1(CC1)C(=O)N2c1c(F)cc(NC(=O)c2ccccn2)cc1F]

To a solution of N-[3,5-difluoro-4-(6'-oxospiro[cyclopropane-1,5'-imidazo[1,2-a]imidazole]-7'-yl)phenyl]pyridine-2-carboxamide (Example 7) (100 mg, 0.260 mmol, 1 eq.) in DMF (7 ml) at 25° C. was added Vilsmeier reagent (chloromethylene)dimethyliminium chloride (168 mg, 1.31 mmol, 5 eq.) and the reaction mixture was stirred at 70° C. for 3 h. The solvent was evaporated and the resulting crude was taken in ethyl acetate and washed with water. The organic layer was dried over Na₂SO₄ and evaporated to get N-[3,5-difluoro-4-(3'-formyl-6'-oxo-spiro[cyclopropane-1,5'-imidazo[1,2-a]imidazole]-7'-yl)phenyl]pyridine-2-carboxamide (60 mg, 0.150 mmol, 36.9% yield) along with some impurities as brown liquid that was used in next step without further purification. M+H+=410.2.

Example E.3

Preparation of 7'-[4-(4-tert-butylpyrazol-1-yl)-2,6-difluoro-phenyl]-6'-oxo-spiro[cyclopropane-1,5'-imidazo[1,2-a]imidazole]-3'-carbaldehyde

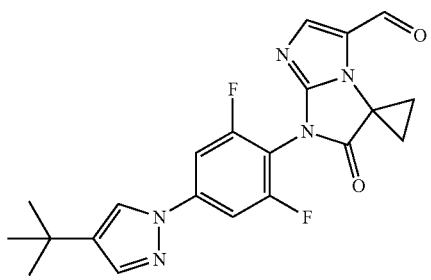 [SMILES: CC(C)(C)c1cnn(-c2cc(F)c(N3C(=O)C4(CC4)n4c(C=O)cnc43)c(F)c2)c1]

To a solution of 7'-[4-(4-tert-butylpyrazol-1-yl)-2,6-difluoro-phenyl]spiro[cyclopropane-1,5'-imidazo[1,2-a]imidazole]-6'-one (Example B.3) (200 mg, 0.520 mmol, 1 eq.) in DMF (5 ml) at 25° C. was added Vilsmeier reagent (chloromethylene)dimethyliminium chloride (200 mg, 1.56 mmol, 3 eq.) and the reaction mixture was stirred at 70° C. for 1 h. The solvent was evaporated and resulting crude was taken in ethyl acetate and washed with water. The organic layer was dried over Na₂SO₄ and evaporated to get 7'-[4-(4-tert-butylpyrazol-1-yl)-2,6-difluoro-phenyl]-6'-oxo-spiro[cyclopropane-1,5'-imidazo[1,2-a]imidazole]-3'-carbaldehyde (150 mg, 0.360 mmol, 48.2% yield) along with some impurities as brown semi-solid that was used in next step without further purification. M+H+=412.0.

Example 55

Preparation of 7'-[2,6-difluoro-4-(2-phenylethynyl)phenyl]-3'-(hydroxymethyl)spiro[cyclopropane-1,5'-imidazo[1,2-a]imidazole]-6'-one

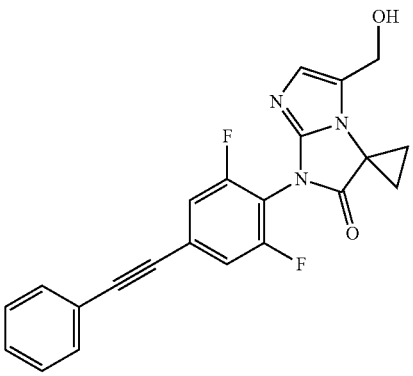 [SMILES: O=C1N(c2c(F)cc(C#Cc3ccccc3)cc2F)c2ncc(CO)n2C12CC2]

To a cold (−10° C.) solution of 7'-[2,6-difluoro-4-(2-phenylethynyl)phenyl]-6'-oxo-spiro[cyclopropane-1,5'-imidazo[1,2-a]imidazole]-3'-carbaldehyde (Example E.1) (20 mg, 0.050 mmol, 1 eq.) in methanol (1 ml) was added sodium borohydride (0.97 mg, 0.030 mmol, 0.5 eq.) and the reaction was stirred at same temperature for 15 min. The reaction was quenched with water at same temperature, concentrated in vacuo to evaporate the methanol and the aqueous residue was extracted with EtOAc (3×10 ml). The combined organics were washed with water and brine, dried over Na₂SO₄, and concentrated in vacuo. This crude product was combined with the crude product from an equivalent reaction (0.080 mmol aldehyde starting material) for purification by preparative TLC (50% EtOAc in hexane) to afford 7'-[2,6-difluoro-4-(2-phenylethynyl)phenyl]-3'-(hydroxymethyl)spiro[cyclopropane-1,5'-imidazo[1,2-a]imidazole]-6'-one (16 mg, 0.040 mmol, 30% yield) as light yellow solid. M+H+=392.2.

In analogy to Example 55, Example 56 of the following table was prepared from the aldehyde E.2 by reduction with sodium borohydride:

| Example No. | Structure | Systematic Name | Starting materials | MW found (M + H) |
|---|---|---|---|---|
| 56 | 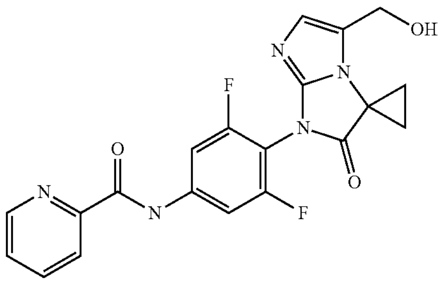 [SMILES: O=C(Nc1cc(F)c(N2C(=O)C3(CC3)n3c(CO)cnc32)c(F)c1)c1ccccn1] | N-[3,5-difluoro-4-[3'-(hydroxymethyl)-6'-oxo-spiro[cyclopropane-1,5'-imidazo[1,2-a]imidazole]-7'-yl]phenyl]pyridine-2-carboxamide | N-[3,5-difluoro-4-(3'-formyl-6'-oxo-spiro[cyclopropane-1,5'-imidazo[1,2-a]imidazole]-7'-yl)phenyl]pyridine-2-carboxamide (Example E.2) and sodium borohydride | 412.2 |

Example 57

Preparation of N-[3,5-difluoro-4-[3'-(1-hydroxyethyl)-6'-oxo-spiro[cyclopropane-1,5'-imidazo[1,2-a]imidazole]-7'-yl]phenyl]pyridine-2-carboxamide To a solution of N-[3,5-difluoro-4-(3'-formyl-6'-oxo-spiro[cyclopropane-1,5'-imidazo[1,2-a]imidazole]-7'-yl)phenyl]pyridine-2-carboxamide (Example E.2) (70 mg, 0.170 mmol, 1 eq.) in THF (5 ml) at 0° C. was added methyl magnesium bromide in ether (0.09 ml, 0.260 mmol, 1.5 eq.) and the reaction mixture was stirred at 0° C. for 1 h. The reaction mixture was quenched with saturated aqueous NH₄Cl solution and extracted with ethyl acetate. The organic layer was dried over Na₂SO₄, concentrated in vacuo, and the resulting crude product was purified by prep HPLC (NH₄OAc/CH₃CN) to yield N-[3,5-difluoro-4-[3'-(1-hydroxyethyl)-6'-oxo-spiro[cyclopropane-1,5'-imidazo[1,2-a]imidazole]-7'-yl]phenyl]pyridine-2-carboxamide (6.5 mg, 0.020 mmol, 8% yield) as white solid. M+H+=426.1.

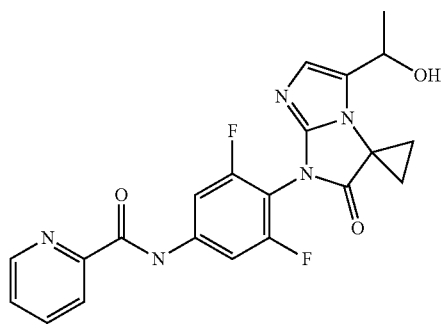 [SMILES: CC(O)c1cnc2n1C1(CC1)C(=O)N2c1c(F)cc(NC(=O)c2ccccn2)cc1F]

In analogy to Example 57, Example 58 of the following table was prepared from the aldehyde E.3 by reaction with methyl magnesium bromide:

| Example No. | Structure | Systematic Name | Starting materials | MW found (M + H) |
|---|---|---|---|---|
| 58 | 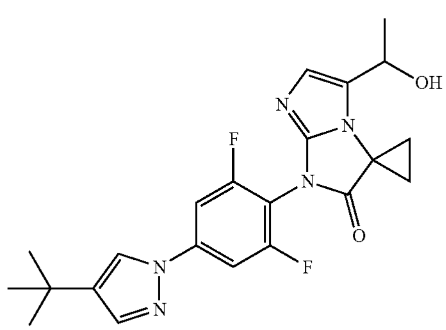 [SMILES: CC(O)c1cnc2n1C1(CC1)C(=O)N2c1c(F)cc(-n2cc(C(C)(C)C)cn2)cc1F] | 7'-[4-(4-tert-butylpyrazol-1-yl)-2,6-difluoro-phenyl]-3'-(1-hydroxyethyl)spiro[cyclopropane-1,5'-imidazo[1,2-a]imidazole]-6'-one | 7'-[4-(4-tert-butylpyrazol-1-yl)-2,6-difluoro-phenyl]-6'-oxo-spiro[cyclopropane-1,5'-imidazo[1,2-a]imidazole]-3'-carbaldehyde (Example E.3) and methyl magnesium bromide | 428.2 |

Example 59

Preparation of 7'-[2,6-difluoro-4-(2-phenylethynyl)phenyl]-3'-(1-hydroxyethyl)spiro[cyclopropane-1,5'-imidazo[1,2-a]imidazole]-6'-one

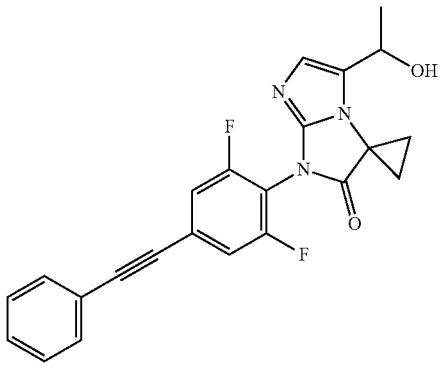 [SMILES: CC(O)c1cnc2n1C1(CC1)C(=O)N2c1c(F)cc(C#Cc2ccccc2)cc1F]

To a solution of 7'-[2,6-difluoro-4-(2-phenylethynyl)phenyl]-6'-oxo-spiro[cyclopropane-1,5'-imidazo[1,2-a]imidazole]-3'-carbaldehyde (Example E.1) (35.0 mg, 0.090 mmol, 1 eq.) in THF (5 ml) at 0° C. was added methyl magnesium bromide in ether (0.04 mL, 0.130 mmol, 1.5 eq) and reaction mixture was stirred at 25° C. for 1.5 h. The reaction mixture was quenched with saturated aqueous NH₄Cl solution and extracted with ethyl acetate. The organic layer was dried over Na₂SO₄, concentrated in vacuo, and the resulting crude product was purified by prep TLC (60% EtOAc in hexane) to get 7'-[2,6-difluoro-4-(2-phenylethynyl)phenyl]-3'-(1-hydroxyethyl)spiro[cyclopropane-1,5'-imidazo[1,2-a]imidazole]-6'-one (8.2 mg, 0.020 mmol, 20% yield) as off white solid. M+H+=406.2.

The invention claimed is:

1. A compound of formula I:

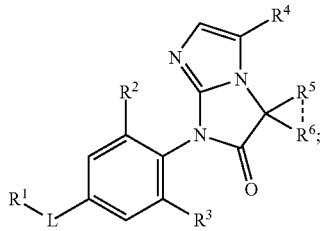

or a pharmaceutically acceptable salt or stereoisomer thereof,
wherein:
L is a bond, —C(O)NH—, or —NHC(O)—;
$R^1$ is phenyl or a 5- or 6-membered heteroaryl, wherein the phenyl or 5- or 6-membered heteroaryl is optionally substituted by 1 or more substituents independently selected from the group consisting of lower alkyl and lower alkoxy, and further wherein the lower alkyl is optionally substituted by 1 or more independently selected halogen substituents and the lower alkoxy is optionally substituted by 1 or more independently selected halogen substituents;
$R^2$ is F;
$R^3$ is F or Cl;
$R^4$ is H, halogen, lower alkyl, S(O)₂CH₃, heterocycloalkyl, or a 5- or 6-membered heteroaryl, wherein the lower alkyl is optionally substituted by OH, and further wherein the heterocycloalkyl or 5- or 6-membered heteroaryl is optionally substituted by 1 or more substituents independently selected from the group consisting of lower alkyl, OH, and =O; and
(i) $R^5$ is H or CH₃;
$R^6$ is CH₃; and
the dotted line is absent; or
(ii) $R^5$ and $R^6$, together with the carbon atom to which they are attached, form a cyclopropyl ring.

2. The compound or claim 1, wherein the compound is of formula IA:

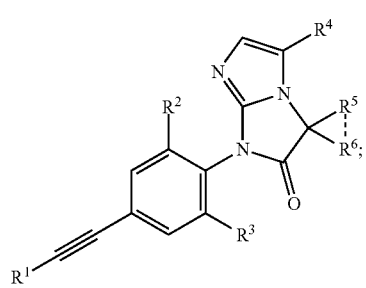

or a pharmaceutically acceptable salt or stereoisomer thereof.

3. The compound or claim 1, wherein the compound is of formula IB:

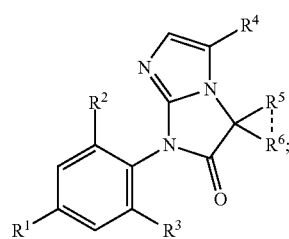

or a pharmaceutically acceptable salt or stereoisomer thereof.

4. The compound or claim 1, wherein the compound is of formula IC:

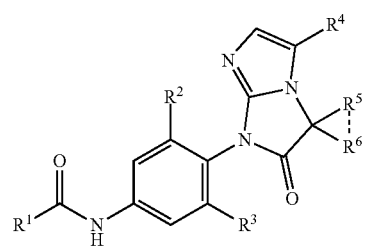

or a pharmaceutically acceptable salt or stereoisomer thereof.

5. The compound or claim 1, wherein the compound is of formula ID:
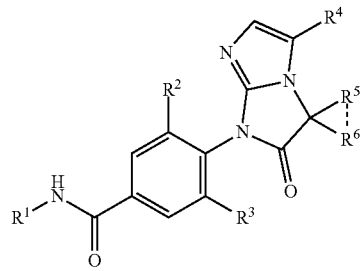
ID
or a pharmaceutically acceptable salt or stereoisomer thereof.
6. The compound of claim 2, or a stereoisomer thereof, wherein the compound, or stereoisomer thereof, is selected from the group consisting of:
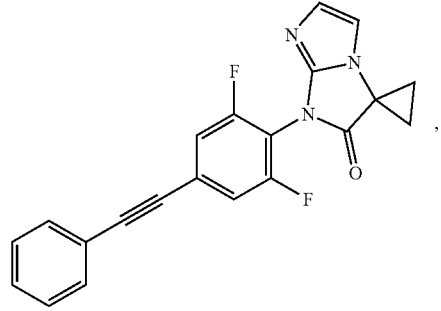
1
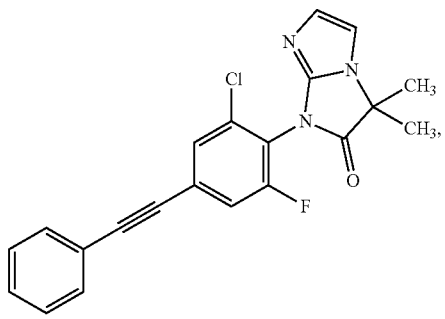
2
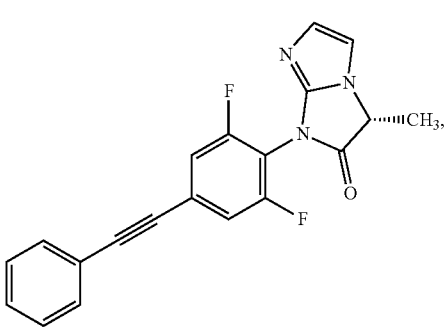
3
-continued
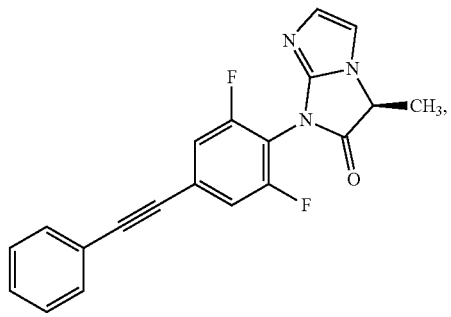
4
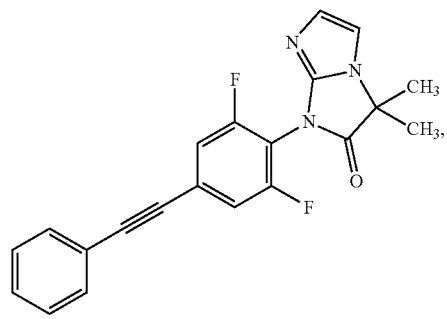
5
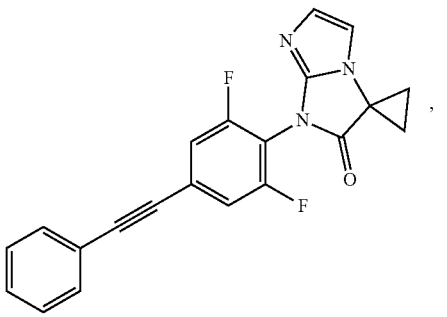
B.1
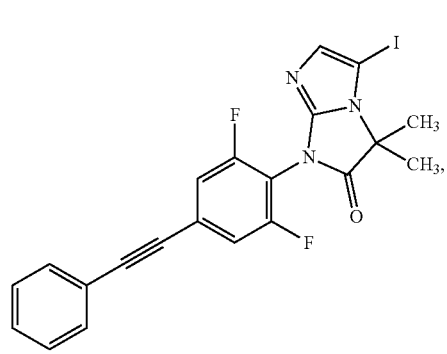
8
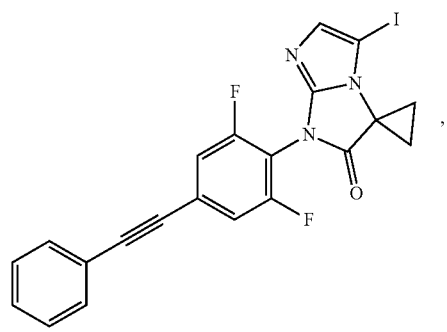
9

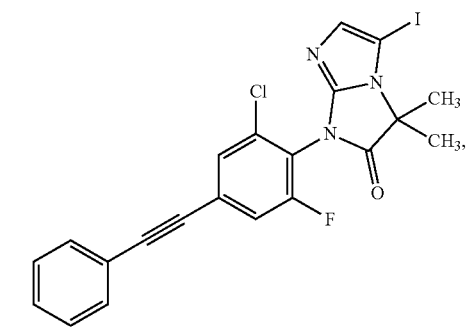
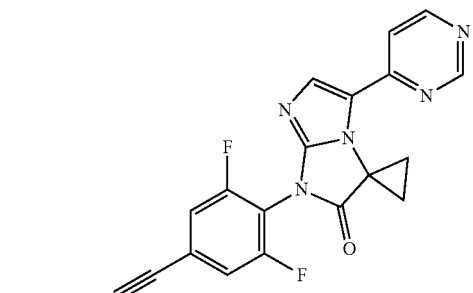
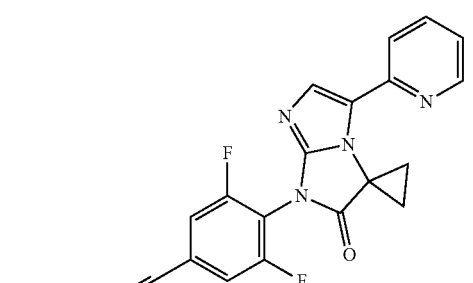
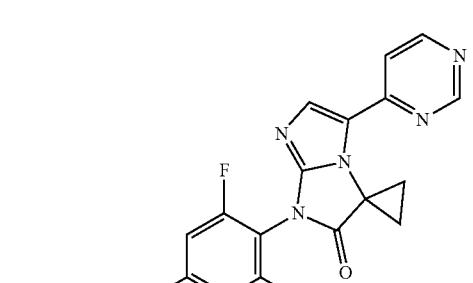
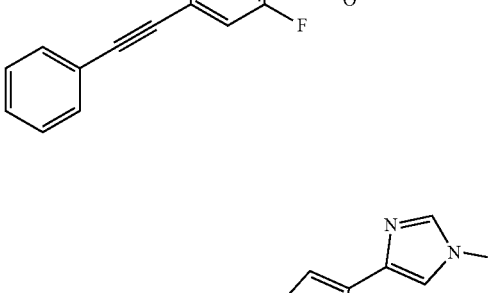
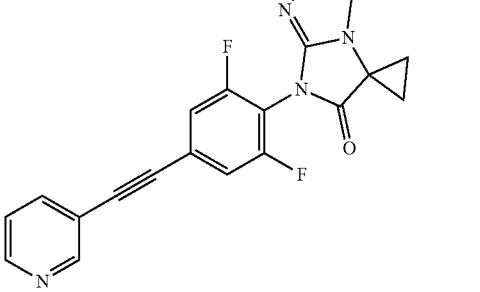

24
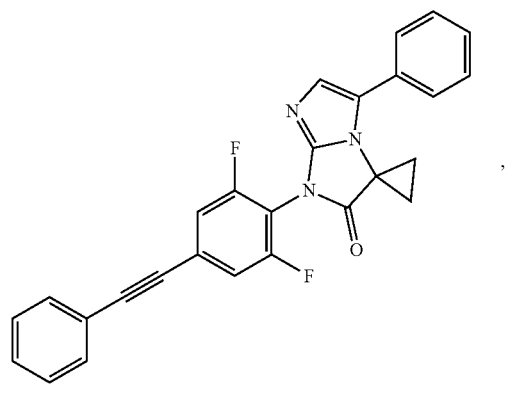
26
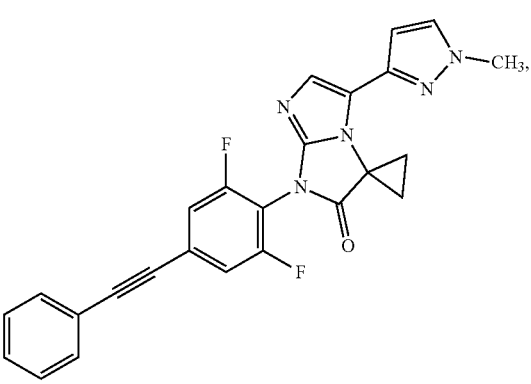
27
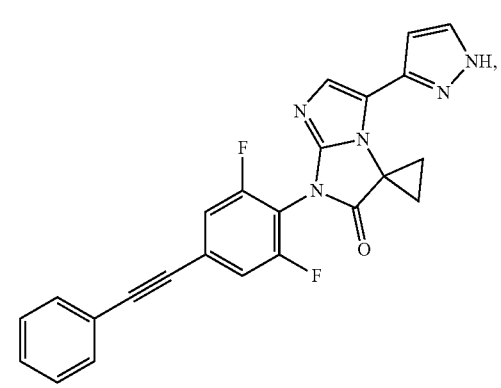
28
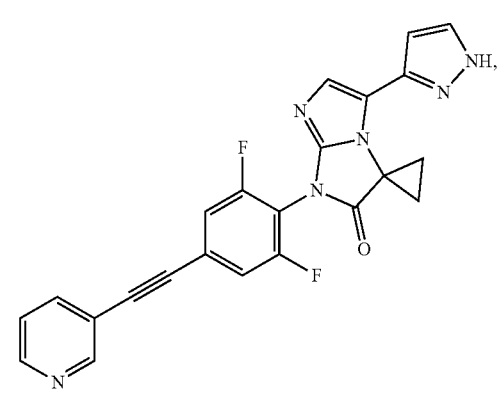
29
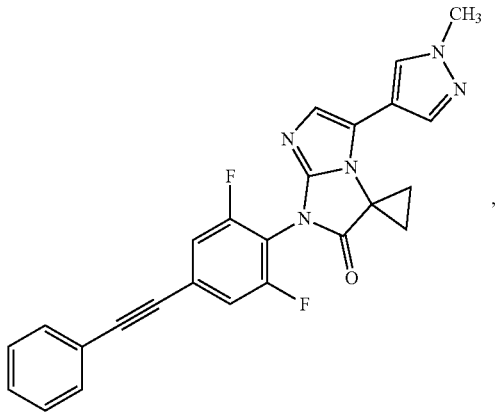
30
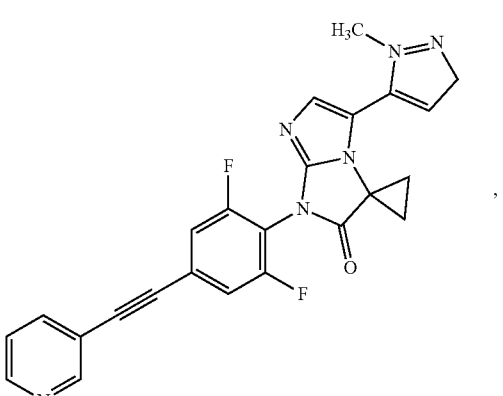
31
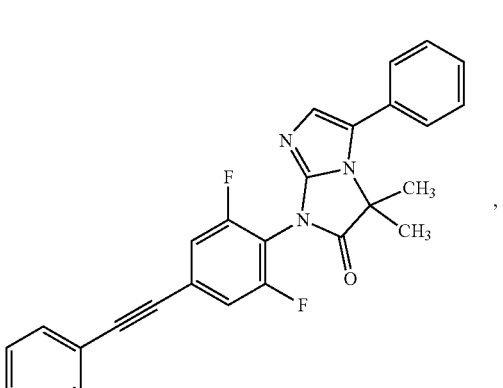
32
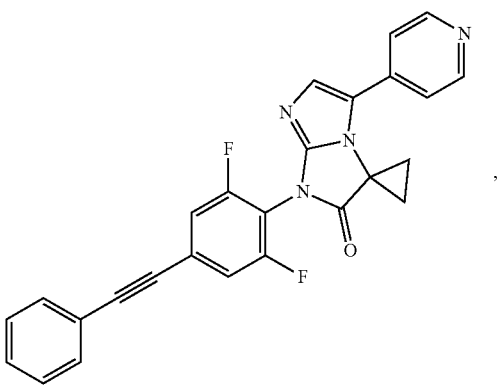

33
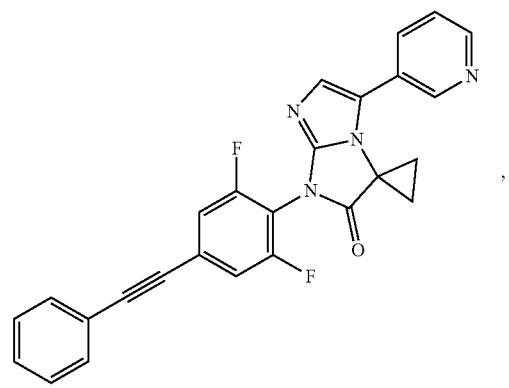
34
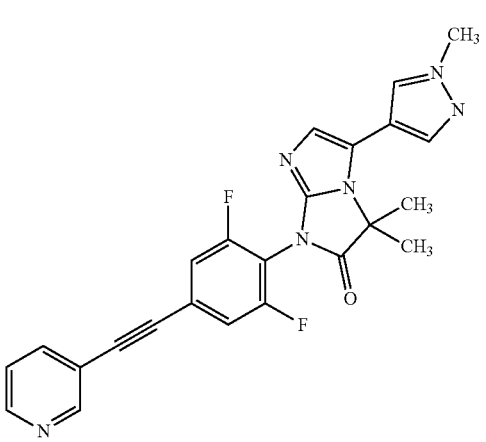
36
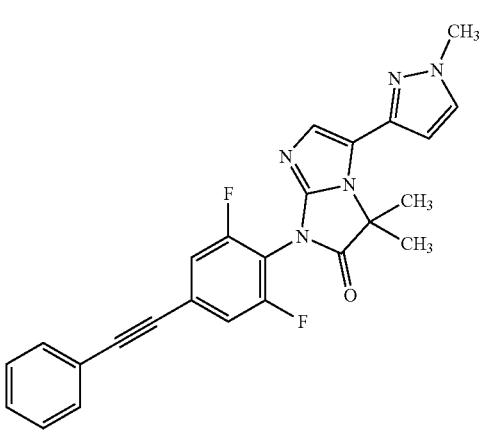
37
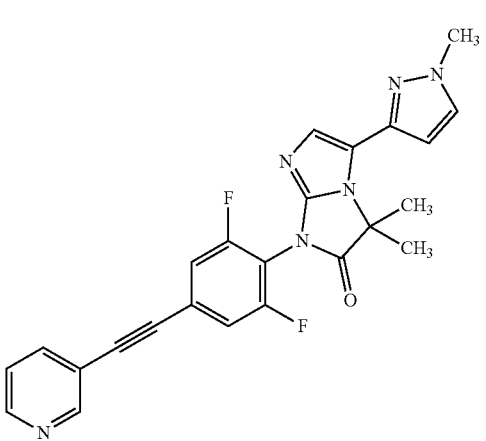
38
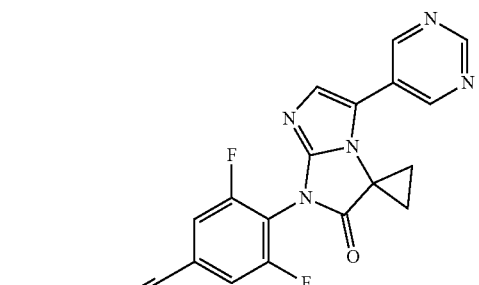
39
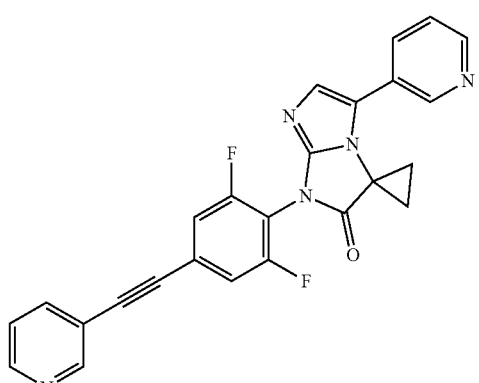
41
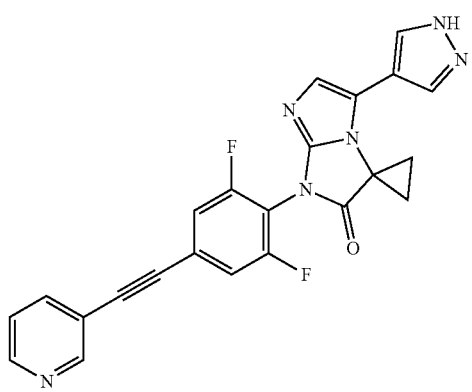
44
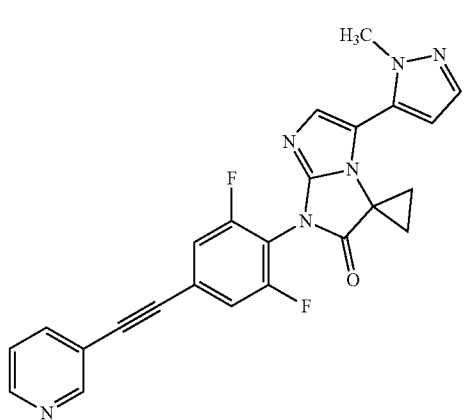

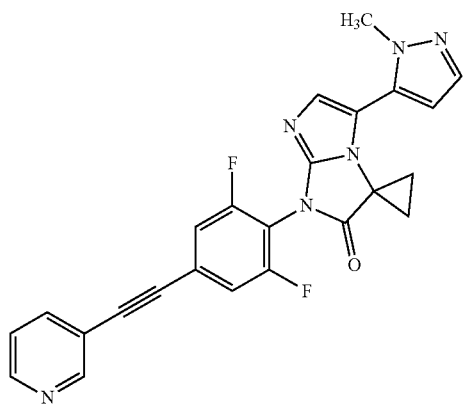
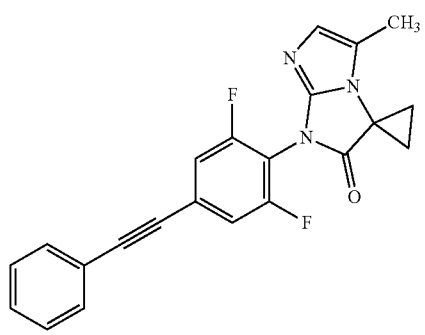
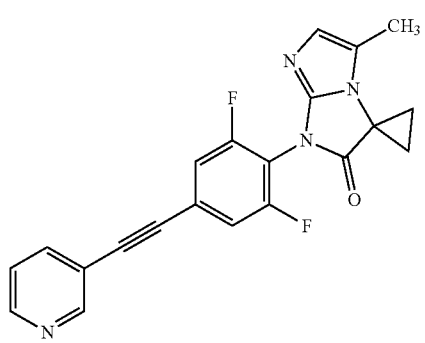
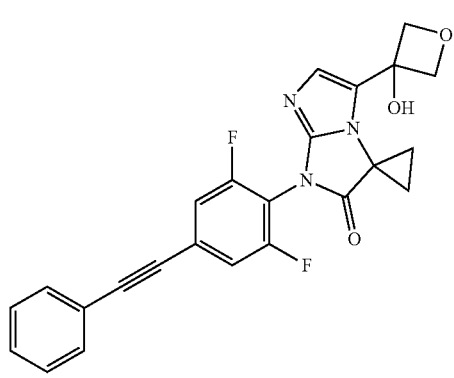
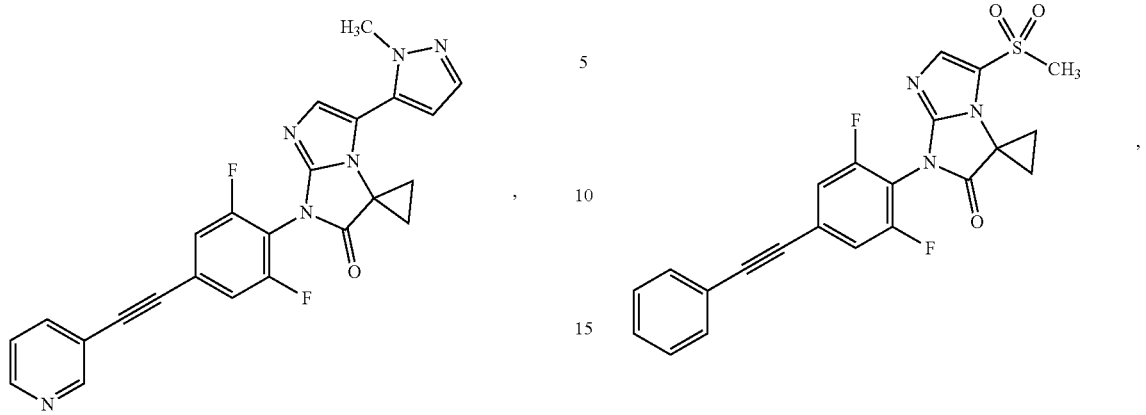
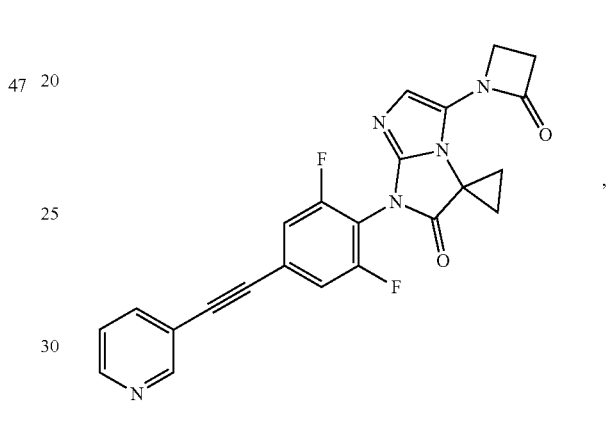
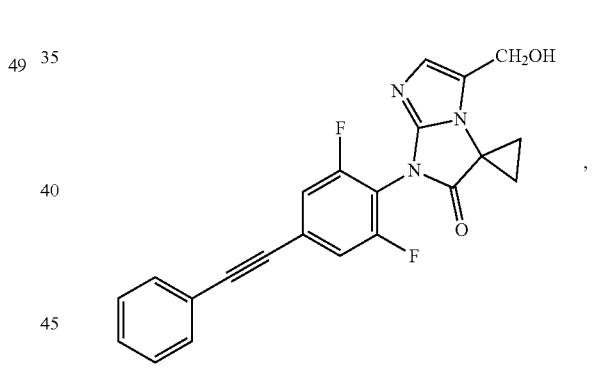
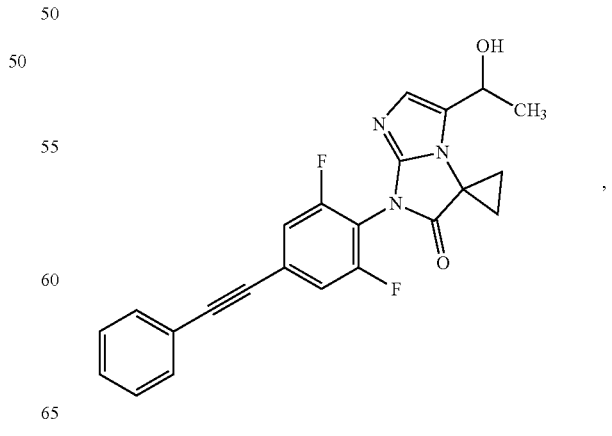
and
or a pharmaceutically acceptable salt thereof.

7. The compound of claim 3, wherein the compound is selected from the group consisting of:
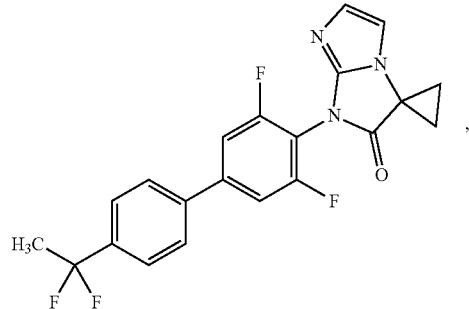
6
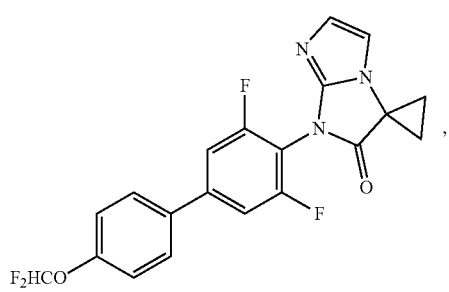
B.2
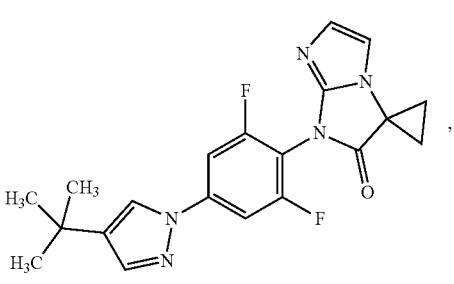
B.3
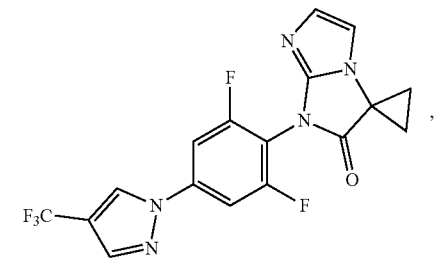
B.6
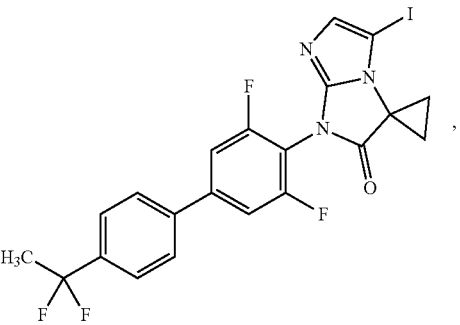
C.2
-continued
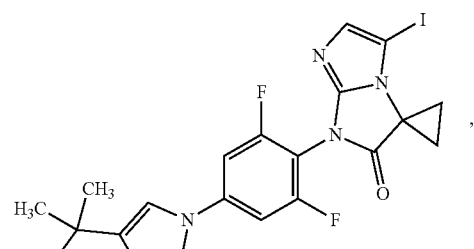
C.4
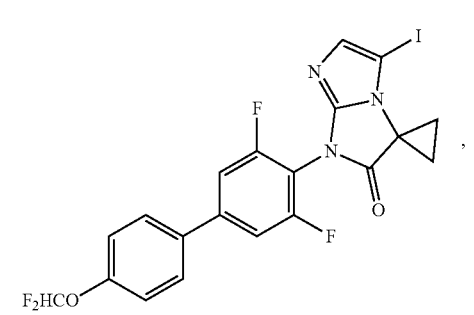
C.6
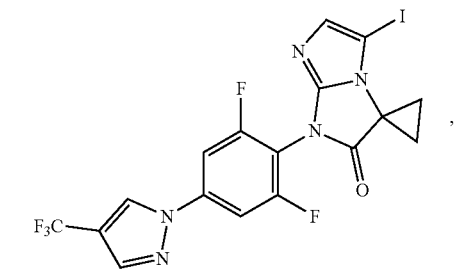
C.7
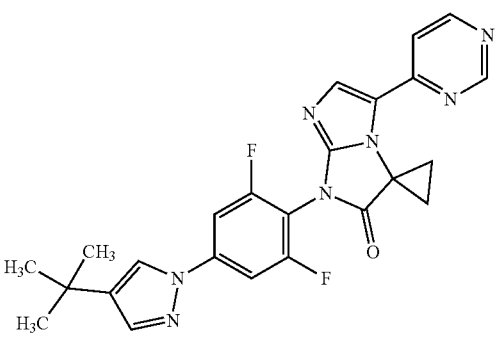
15
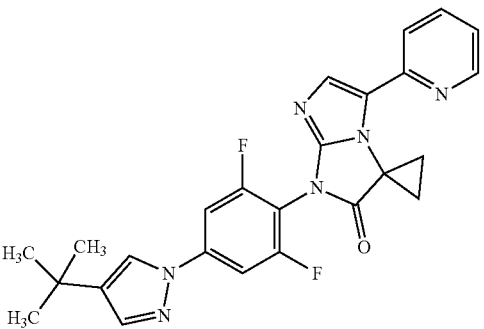
19

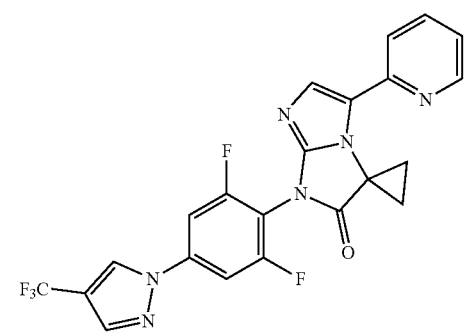
21
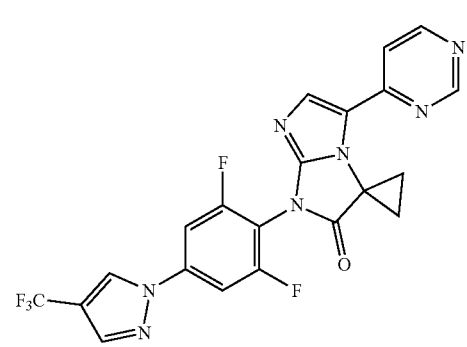
23
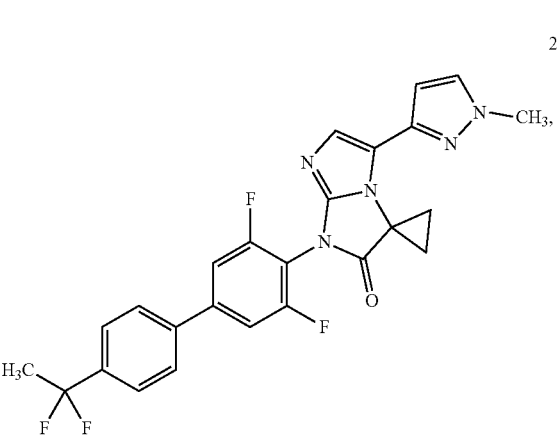
25
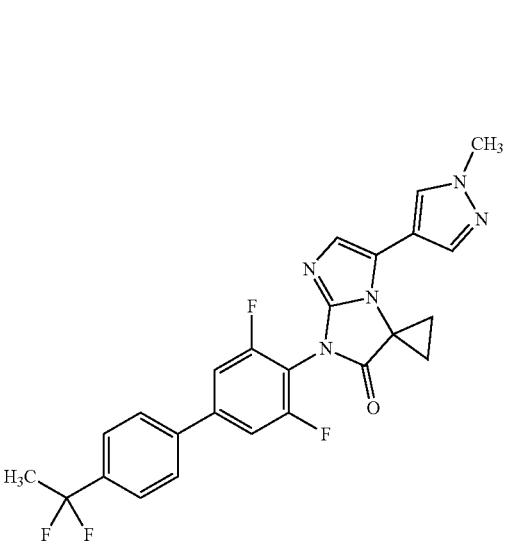
35
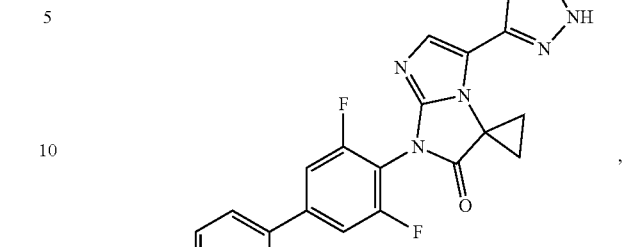
40
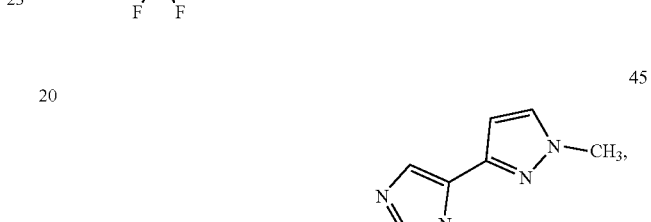
45
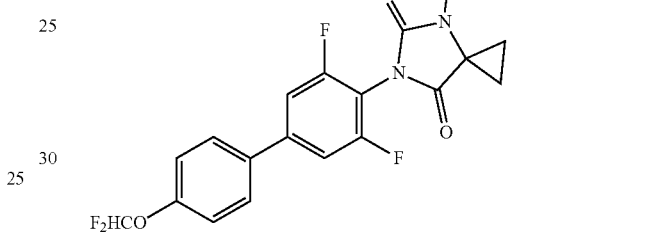
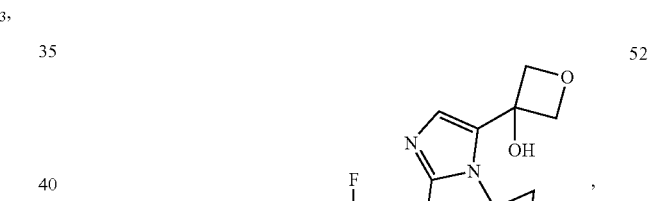
52
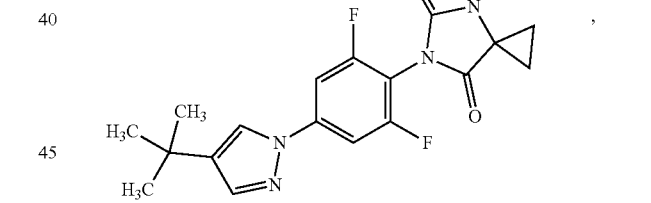
and
58
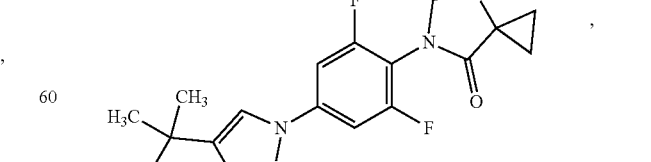
or a pharmaceutically acceptable salt or stereoisomer thereof.

8. The compound of claim 4, wherein the compound is selected from the group consisting of:
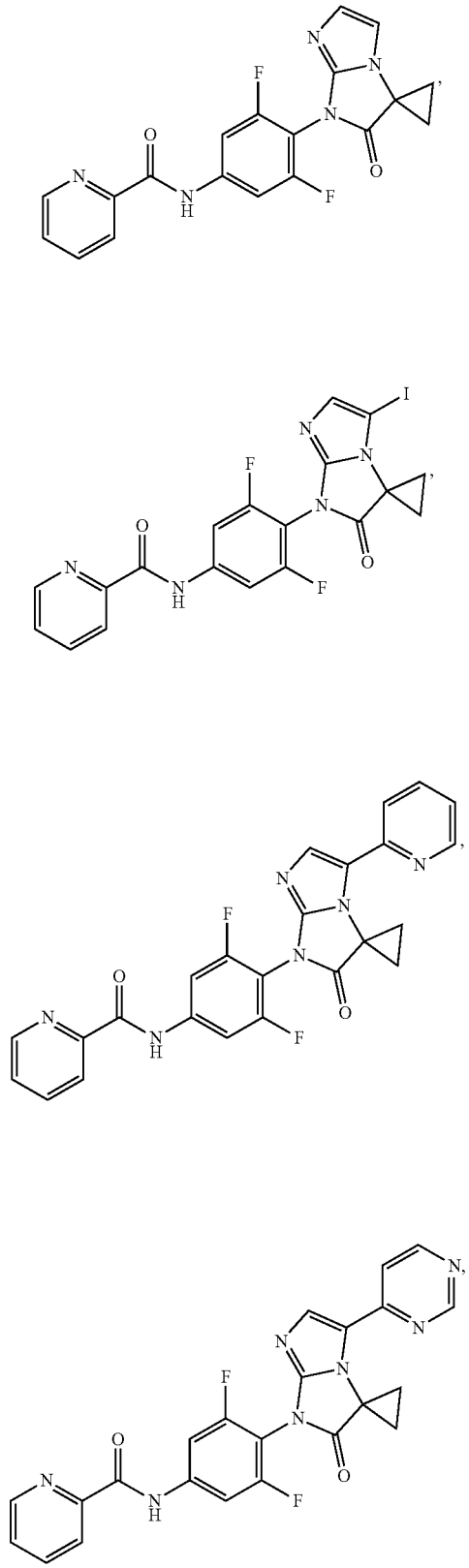
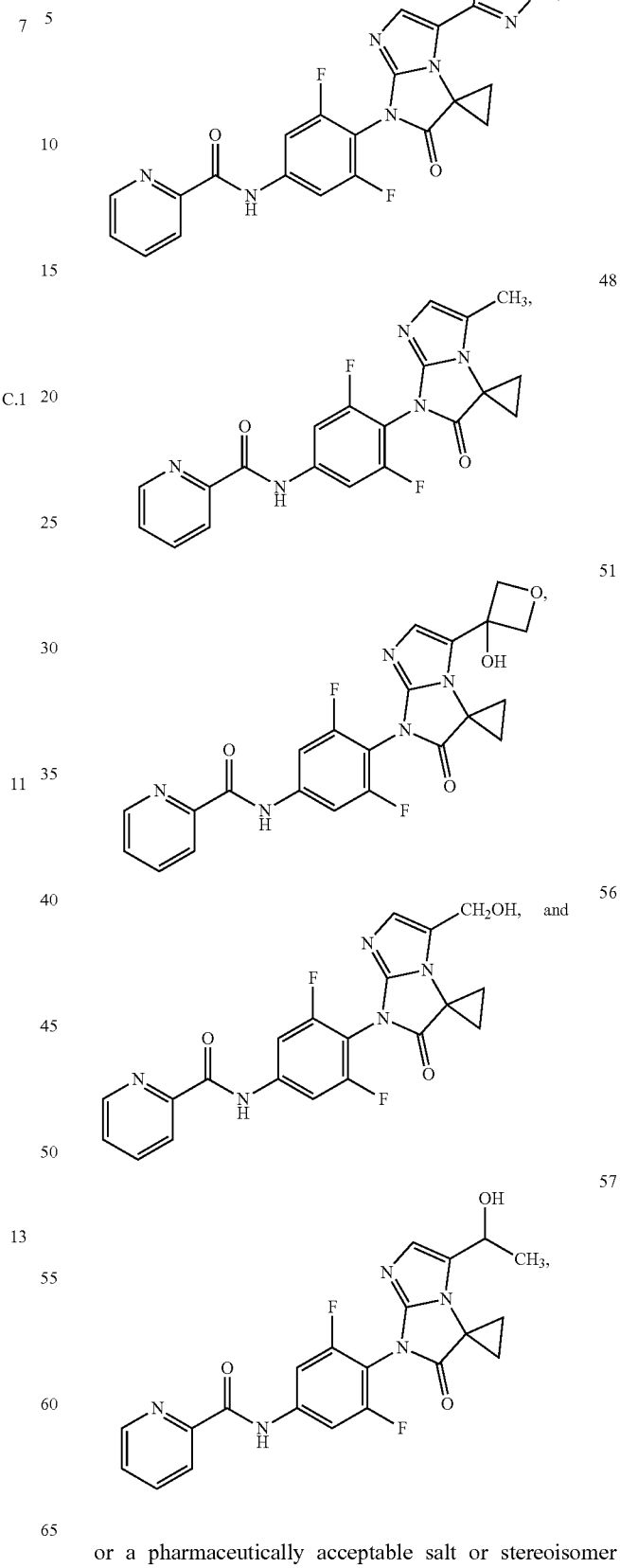
or a pharmaceutically acceptable salt or stereoisomer thereof.

9. The compound of claim 5, wherein the compound is selected from the group consisting of:

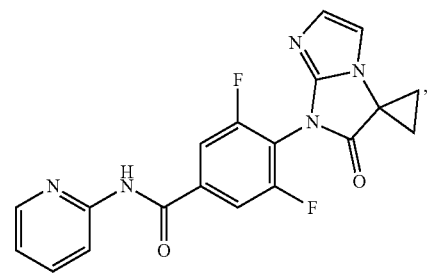

B.4

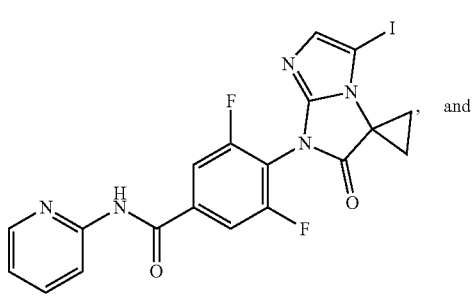

C.5

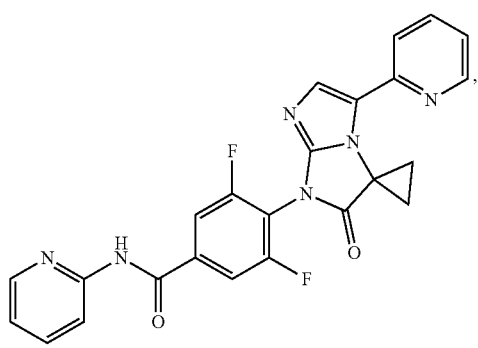

22 or a pharmaceutically acceptable salt thereof.

10. A pharmaceutical composition comprising a compound of claim 1, or a pharmaceutically acceptable salt or stereoisomer thereof, and a pharmaceutically acceptable excipient.

11. A method for modulating metabotropic glutamate receptor 4 activity in a patient, wherein the method comprises administering to the patient in need thereof an effective amount of a compound of claim 1, or a pharmaceutically acceptable salt or stereoisomer thereof.

12. The method of claim 11, wherein the patient has a disease or disorder selected from the group consisting of anxiety, autism, cancer, depression, emesis, neuroprotection, obsessive compulsive disorder, Parkinson's disease, and type 2 diabetes.

13. A process for the manufacture of a compound of claim 1 of formula I:

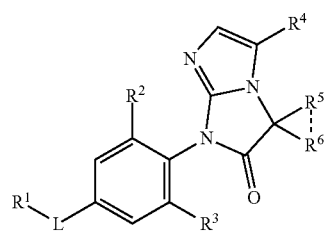

I wherein:
L is a bond, —C(O)NH—, or —NHC(O)—;
$R^1$ is phenyl or a 5- or 6-membered heteroaryl, wherein the phenyl or 5- or 6-membered heteroaryl is optionally substituted by 1 or more substituents independently selected from the group consisting of lower alkyl and lower alkoxy, and further wherein the lower alkyl is optionally substituted by 1 or more independently selected halogen substituents and the lower alkoxy is optionally substituted by 1 or more independently selected halogen substituents;
$R^2$ is F;
$R^3$ is F or Cl;
$R^4$ is H, halogen, lower alkyl, $S(O)_2CH_3$, heterocycloalkyl, or a 5- or 6-membered heteroaryl, wherein the lower alkyl is optionally substituted by OH, and further wherein the heterocycloalkyl or 5- or 6-membered heteroaryl is optionally substituted by 1 or more substituents independently selected from the group consisting of lower alkyl, OH, and =O; and
(i) $R^5$ is H or $CH_3$;
$R^6$ is $CH_3$; and
the dotted line is absent; or
(ii) $R^5$ and $R^6$, together with the carbon atom to which they are attached, form a cyclopropyl ring;
wherein the process comprises a step selected from the group consisting of:
a) reacting a compound of formula Ib:

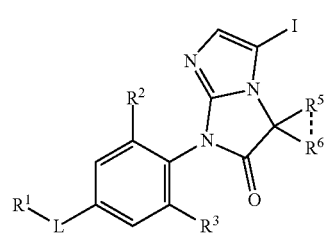

Ib wherein:
L is a bond, —C(O)NH—, or —NHC(O)—;
$R^1$ is phenyl or a 5- or 6-membered heteroaryl, wherein the phenyl or 5- or 6-membered heteroaryl is optionally substituted by 1 or more substituents independently selected from the group consisting of lower alkyl and lower alkoxy, and further wherein the lower alkyl is optionally substituted by 1 or more independently selected halogen substituents and the lower alkoxy is optionally substituted by 1 or more independently selected halogen substituents;

R² is F;
R³ is F or Cl; and
(i) R⁵ is H or CH₃;
R⁶ is CH₃; and
the dotted line is absent; or
(ii) R⁵ and R⁶, together with the carbon atom to which they are attached, form a cyclopropyl ring;
with an organometallic reagent of the following formula:

R⁴-M, wherein:
R⁴ is CH₃ or a 5- or 6-membered heteroaryl; and
M is a boronic acid or a stannane;
to form a compound of formula Ic:

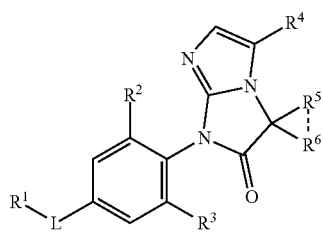

Ic or a pharmaceutically acceptable salt thereof,
wherein:
L is a bond, —C(O)NH—, or —NHC(O)—;
R¹ is phenyl or a 5- or 6-membered heteroaryl, wherein the phenyl or 5- or 6-membered heteroaryl is optionally substituted by 1 or more substituents independently selected from the group consisting of lower alkyl and lower alkoxy, and further wherein the lower alkyl is optionally substituted by 1 or more independently selected halogen substituents and the lower alkoxy is optionally substituted by 1 or more independently selected halogen substituents;
R² is F;
R³ is F or Cl;
R⁴ is CH₃ or a 5- or 6-membered heteroaryl; and
(i) R⁵ is H or CH₃;
R⁶ is CH₃; and
the dotted line is absent; or
(ii) R⁵ and R⁶, together with the carbon atom to which they are attached, form a cyclopropyl ring;
b) reacting a compound of formula Ib:

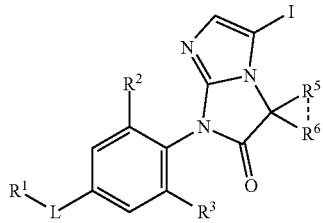

Ib wherein:
L is a bond, —C(O)NH—, or —NHC(O)—;
R¹ is phenyl or a 5- or 6-membered heteroaryl, wherein the phenyl or 5- or 6-membered heteroaryl is optionally substituted by 1 or more substituents independently selected from the group consisting of lower alkyl and lower alkoxy, and further wherein the lower alkyl is optionally substituted by 1 or more independently selected halogen substituents and the lower alkoxy is optionally substituted by 1 or more independently selected halogen substituents;
R² is F;
R³ is F or Cl; and
(i) R⁵ is H or CH₃;
R⁶ is CH₃; and
the dotted line is absent; or
(ii) R⁵ and R⁶, together with the carbon atom to which they are attached, form a cyclopropyl ring;
with an alkylmagnesium bromide, followed by methanesulfonyl chloride or a reagent of the following formula:

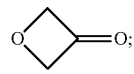

to form a compound of formula Je:

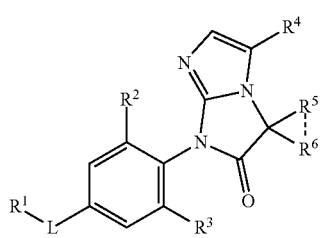

Ie or a pharmaceutically acceptable salt thereof,
wherein:
L is a bond, —C(O)NH—, or —NHC(O)—;
R¹ is phenyl or a 5- or 6-membered heteroaryl, wherein the phenyl or 5- or 6-membered heteroaryl is optionally substituted by 1 or more substituents independently selected from the group consisting of lower alkyl and lower alkoxy, and further wherein the lower alkyl is optionally substituted by 1 or more independently selected halogen substituents and the lower alkoxy is optionally substituted by 1 or more independently selected halogen substituents
R² is F;
R³ is F or Cl;
R⁴ is S(O)₂CH₃ or

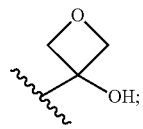 [SMILES: *C1(O)COC1]

and
(i) R⁵ is H or CH₃;
R⁶ is CH₃; and
the dotted line is absent; or
(ii) R⁵ and R⁶, together with the carbon atom to which they are attached, form a cyclopropyl ring;

c) reacting a compound of formula XIV:

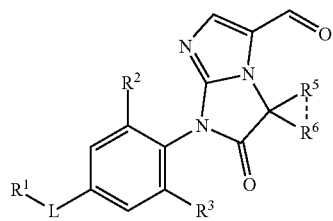

XIV wherein:
L is a bond, —C(O)NH—, or —NHC(O)—;
R¹ is phenyl or a 5- or 6-membered heteroaryl, wherein the phenyl or 5- or 6-membered heteroaryl is optionally substituted by 1 or more substituents independently selected from the group consisting of lower alkyl and lower alkoxy, and further wherein the lower alkyl is optionally substituted by 1 or more independently selected halogen substituents and the lower alkoxy is optionally substituted by 1 or more independently selected halogen substituents;
R² is F;
R³ is F or Cl; and
(i) R⁵ is H or CH₃;
R⁶ is CH₃; and
the dotted line is absent; or
(ii) R⁵ and R⁶, together with the carbon atom to which they are attached, form a cyclopropyl ring;
with sodium borohydride or an alkylmagnesium bromide of the following formula:

R—MgBr, wherein:
R is lower alkyl;
to form a compound of formula Id:

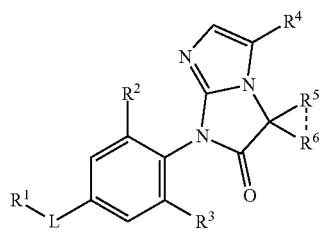

Id or a pharmaceutically acceptable salt thereof, wherein:
L is a bond, —C(O)NH—, or —NHC(O)—;
R¹ is phenyl or a 5- or 6-membered heteroaryl, wherein the phenyl or 5- or 6-membered heteroaryl is optionally substituted by 1 or more substituents independently selected from the group consisting of lower alkyl and lower alkoxy, and further wherein the lower alkyl is optionally substituted by 1 or more independently selected halogen substituents and the lower alkoxy is optionally substituted by 1 or more independently selected halogen substituents;

R² is F;
R³ is F or Cl;
R⁴ is CH₂OH or lower alkyl substituted by OH; and
(i) R⁵ is H or CH₃;
R⁶ is CH₃; and
the dotted line is absent; or
(ii) R⁵ and R⁶, together with the carbon atom to which they are attached, form a cyclopropyl ring;
d) reacting a compound of formula Ia:

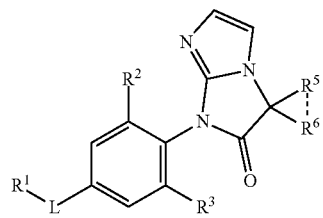

Ia wherein:
L is a bond, —C(O)NH—, or —NHC(O)—;
R¹ is phenyl or a 5- or 6-membered heteroaryl, wherein the phenyl or 5- or 6-membered heteroaryl is optionally substituted by 1 or more substituents independently selected from the group consisting of lower alkyl and lower alkoxy, and further wherein the lower alkyl is optionally substituted by 1 or more independently selected halogen substituents and the lower alkoxy is optionally substituted by 1 or more independently selected halogen substituents;
R² is F;
R³ is F or Cl; and
(i) R⁵ is H or CH₃;
R⁶ is CH₃; and
the dotted line is absent; or
(ii) R⁵ and R⁶, together with the carbon atom to which they are attached, form a cyclopropyl ring;
with N-iodosuccinimide, to form a compound of formula Ib:

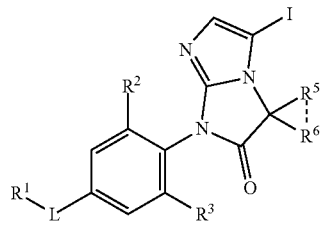

Ib or a pharmaceutically acceptable salt thereof, wherein:
L is a bond, —C(O)NH—, or —NHC(O)—;
R¹ is phenyl or a 5- or 6-membered heteroaryl, wherein the phenyl or 5- or 6-membered heteroaryl is optionally substituted by 1 or more substituents independently selected from the group consisting of lower alkyl and lower alkoxy, and further wherein the lower alkyl is optionally substituted by 1 or more independently selected halogen substituents and the lower alkoxy is optionally substituted by 1 or more independently selected halogen substituents;

R² is F;
R³ is F or Cl; and
(i) R⁵ is H or CH₃;
R⁶ is CH₃; and
the dotted line is absent; or
(ii) R⁵ and R⁶, together with the carbon atom to which they are attached, form a cyclopropyl ring;
e) reacting a compound of formula Ib:

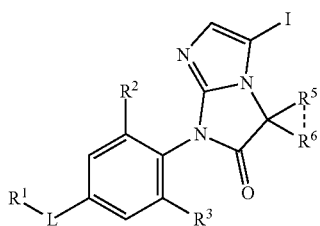

Ib wherein:
L is a bond, —C(O)NH—, or —NHC(O)—;
R¹ is phenyl or a 5- or 6-membered heteroaryl, wherein the phenyl or 5- or 6-membered heteroaryl is optionally substituted by 1 or more substituents independently selected from the group consisting of lower alkyl and lower alkoxy, and further wherein the lower alkyl is optionally substituted by 1 or more independently selected halogen substituents and the lower alkoxy is optionally substituted by 1 or more independently selected halogen substituents;
R² is F;
R³ is F or Cl; and
(i) R⁵ is H or CH₃;
R⁶ is CH₃; and
the dotted line is absent; or
(ii) R⁵ and R⁶, together with the carbon atom to which they are attached, form a cyclopropyl ring;
with a lactam of the following formula:

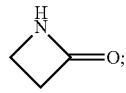

to form a compound of formula Ig:

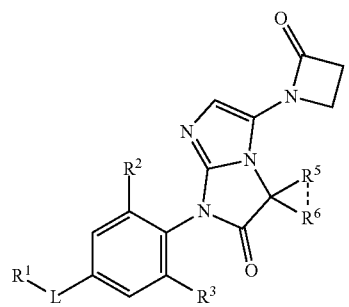

Ig or a pharmaceutically acceptable salt thereof, wherein:
L is a bond, —C(O)NH—, or —NHC(O)—;
R¹ is phenyl or a 5- or 6-membered heteroaryl, wherein the phenyl or 5- or 6-membered heteroaryl is optionally substituted by 1 or more substituents independently selected from the group consisting of lower alkyl and lower alkoxy, and further wherein the lower alkyl is optionally substituted by 1 or more independently selected halogen substituents and the lower alkoxy is optionally substituted by 1 or more independently selected halogen substituents;
R² is F;
R³ is F or Cl; and
(i) R⁵ is H or CH₃;
R⁶ is CH₃; and
the dotted line is absent; or
(ii) R⁵ and R⁶, together with the carbon atom to which they are attached, form a cyclopropyl ring;
f) reacting a compound of formula II:

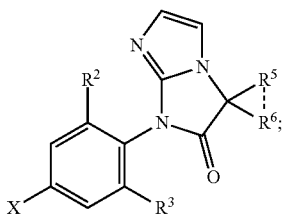

II wherein:
X is Cl or I;
R² is F;
R³ is F or Cl; and
(i) R⁵ is H or CH₃;
R⁶ is CH₃; and
the dotted line is absent; or
(ii) R⁵ and R⁶, together with the carbon atom to which they are attached, form a cyclopropyl ring;
with a compound of the following formula:
R¹-L-H
wherein:
L is a bond, —C(O)NH—, or —NHC(O)—; and
R¹ is phenyl or a 5- or 6-membered heteroaryl, wherein the phenyl or 5- or 6-membered heteroaryl is optionally substituted by 1 or more substituents independently selected from the group consisting of lower alkyl and lower alkoxy, and further wherein the lower alkyl is optionally substituted by 1 or more independently selected halogen substituents and the lower alkoxy is optionally substituted by 1 or more independently selected halogen substituents;
to form a compound of formula Ia:

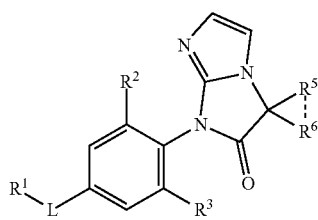

Ia or a pharmaceutically acceptable salt thereof, wherein:
L is a bond, —C(O)NH—, or —NHC(O)—;
$R^1$ is phenyl or a 5- or 6-membered heteroaryl, wherein the phenyl or 5- or 6-membered heteroaryl is optionally substituted by 1 or more substituents independently selected from the group consisting of lower alkyl and lower alkoxy, and further wherein the lower alkyl is optionally substituted by 1 or more independently selected halogen substituents and the lower alkoxy is optionally substituted by 1 or more independently selected halogen substituents;
$R^2$ is F;
$R^3$ is F or Cl; and
(i) $R^5$ is H or $CH_3$;
$R^6$ is $CH_3$; and
the dotted line is absent; or
(ii) $R^5$ and $R^6$, together with the carbon atom to which they are attached, form a cyclopropyl ring; and
g) reacting a compound of formula Ib:

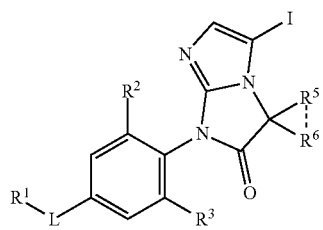

Ib wherein:
L is a bond, —C(O)NH—, or —NHC(O)—;
$R^1$ is phenyl or a 5- or 6-membered heteroaryl, wherein the phenyl or 5- or 6-membered heteroaryl is optionally substituted by 1 or more substituents independently selected from the group consisting of lower alkyl and lower alkoxy, and further wherein the lower alkyl is optionally substituted by 1 or more independently selected halogen substituents and the lower alkoxy is optionally substituted by 1 or more independently selected halogen substituents;

$R^2$ is F;
$R^3$ is F or Cl; and
(i) $R^5$ is H or $CH_3$;
$R^6$ is $CH_3$; and
the dotted line is absent; or
(ii) $R^5$ and $R^6$, together with the carbon atom to which they are attached, form a cyclopropyl ring;
with isopropylmagnesium chloride, followed by methanesulfonyl chloride, to form a compound of formula If:

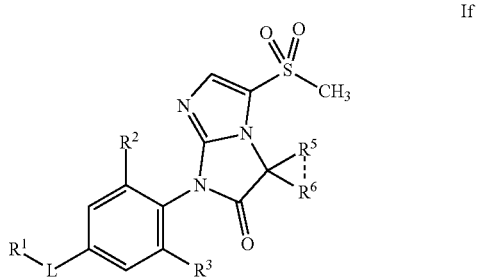

If or a pharmaceutically acceptable salt thereof,
wherein:
L is a bond, —C(O)NH—, or —NHC(O)—;
$R^1$ is phenyl or a 5- or 6-membered heteroaryl, wherein the phenyl or 5- or 6-membered heteroaryl is optionally substituted by 1 or more substituents independently selected from the group consisting of lower alkyl and lower alkoxy, and further wherein the lower alkyl is optionally substituted by 1 or more independently selected halogen substituents and the lower alkoxy is optionally substituted by 1 or more independently selected halogen substituents;
$R^2$ is F;
$R^3$ is F or Cl; and
(i) $R^5$ is H or $CH_3$;
$R^6$ is $CH_3$; and
the dotted line is absent; or
(ii) $R^5$ and $R^6$, together with the carbon atom to which they are attached, form a cyclopropyl ring.

* * * * *